US011213004B2

(12) United States Patent
Bovet et al.

(10) Patent No.: US 11,213,004 B2
(45) Date of Patent: Jan. 4, 2022

(54) REDUCING CADMIUM ACCUMULATION IN FIELD GROWN TOBACCO PLANTS

(71) Applicant: PHILIP MORRIS PRODUCTS S.A., Neuchatel (CH)

(72) Inventors: Lucien Bovet, La Chaux-de-Fonds (CH); Verena Liedschulte, Valangin (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 16/072,391

(22) PCT Filed: Jan. 27, 2017

(86) PCT No.: PCT/EP2017/051761
§ 371 (c)(1),
(2) Date: Jul. 24, 2018

(87) PCT Pub. No.: WO2017/129739
PCT Pub. Date: Aug. 3, 2017

(65) Prior Publication Data
US 2019/0387702 A1 Dec. 26, 2019

(30) Foreign Application Priority Data

Jan. 29, 2016 (EP) ..................................... 16153529

(51) Int. Cl.
*C12N 15/82* (2006.01)
*A01H 6/82* (2018.01)
*A24B 15/10* (2006.01)
*A24B 15/24* (2006.01)

(52) U.S. Cl.
CPC ............ *A01H 6/823* (2018.05); *A24B 15/10* (2013.01); *A24B 15/248* (2013.01); *C12N 15/8218* (2013.01); *C12N 15/8242* (2013.01)

(58) Field of Classification Search
None
See application file for complete search history.

(56) References Cited

FOREIGN PATENT DOCUMENTS

| WO | 2006/091194 | 8/2006 | | |
|---|---|---|---|---|
| WO | 2008/070274 | 6/2008 | | |
| WO | 2009/064771 | 5/2009 | | |
| WO | 2009/074325 | 6/2009 | | |
| WO | WO 2009/074843 | 6/2009 | | |
| WO | 2011/088180 | 7/2011 | | |
| WO | 2012/028309 | 3/2012 | | |
| WO | 2012/041913 | 4/2012 | | |
| WO | WO-2012041913 A1 * | 4/2012 | ............... | C12N 9/14 |
| WO | 2013/119541 | 8/2013 | | |
| WO | WO-2013119541 A1 * | 8/2013 | ............... | A01H 5/12 |

OTHER PUBLICATIONS

Hermand, Victor, "Analyse Fonctionnelle de deux Heavy Metal ATPases de Nicotiana Tabacum", Jun. 25, 2012; PHD thesis).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Smith et al. (Nature Biotechnology, 15:1222-1223, 1997).*
Bork et al. (TIG, 12:425-427, 1996).*
Doerks et al., (TIG, 14:248-250, 1998).*
Nishimura et al. (Plant Cell Physiol., 41 (5):583-590, 2000).*
Yang et al. (PNAS, 98:11438-11443, 2001).*
McConnell et al. (Nature, 411:709-713, 2001).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Arziman et al. (Nucleic Acids Research, 33:582-588, 2005).*
Bonawitz et al.,(Annu. Rev. Genet. 44: 337-363, 2010).*
Paul et al., (Plant Cell Reports; 35:1417-1427; 2016).*
Hermand et al. (Metallomics, 6:1427-1440, 2014).*
Victor Hermand ("Analyse fonctionnelle de deux Heavy Metal ATPases de Nicotiana tabacum", PhD Thesis, Published Jun. 25, 2012; English translation, pp. 1-208.*
GenBank Accession No. CCQ77798. National Center for Biotechnology Information, National Library of Medicine, National Institutes of Health, GenBank Locus CCQ77798, Accession No. CC177798, "Heavy Metal ATPase [Nicotiana tabacum]," [online], Bethesda, MD [retrieved on Mar. 12, 2019], Retrieved from the Internet: <URL:https://www.ncbi.nlm.nih.gov/protein/CCQ77798, 2 pages.
GenBank Accession No. CCW03243.1. National Center for Biotechnology Information, National Library of Medicine, National Institutes of Health, GenBank Locus CCW03243, Accession No. CCW03243, "Heavy Metal ATPase [Nicotiana tabacum]," [online], Bethesda, MD [retrieved on Mar. 12, 2019], Retrieved from the Internet: <URL:https://www.ncbi.nlm.nih.gov/protein/CCW03243.1, 2 pages.

(Continued)

Primary Examiner — Vinod Kumar
(74) Attorney, Agent, or Firm — Mueting Raasch Group

(57) ABSTRACT

There is described herein a mutant plant or part thereof having at least partially reduced expression or activity of at least two heavy metal ATPases (HMAs), said two HMAs comprising, consisting or consisting essentially of: (i) polypeptides having at least 65% sequence identity to SEQ ID NO:1 and SEQ ID NO:2; (ii) polynucleotides encoding the polypeptides set forth in (i); or (iii) polynucleotides having at least 65% sequence identity to SEQ ID NO:3 and SEQ ID NO:4 encoding HMAs; wherein the expression or activity of one of the HMAs set forth in (i) or (ii) or (iii) is partially reduced or lost and the expression or activity of one of the HMAs set forth in (i) or (ii) or (iii) is lost as compared to a control plant; and wherein the mutant plant or part thereof exhibits at least a 27% reduction, as compared to the control plant, in the accumulation of cadmium in leaf when the mutant plant is grown in the field in the presence of naturally or non-naturally occurring cadmium.

13 Claims, 9 Drawing Sheets

Specification includes a Sequence Listing.

(56) References Cited

OTHER PUBLICATIONS

GenBank Accession No. HF675181.1 National Center for Biotechnology Information, National Library of Medicine, National Institutes of Health, GenBank Locus HF675181, Accession No. HF675181, "Nicotiana Tabacum mRNA for Heavy Metal ATPase (HM-A gene), strain BB16NN," [online], Bethesda, MD [retrieved on Mar. 12, 2019], Retrieved from the Internet: <URL:https://www.ncbi.nlm.nih.gov/nuccore, HF675181.1, 3 pages.
GenBank Accession No. HF937054.1 National Center for Biotechnology Information, National Library of Medicine, National Institutes of Health, GenBank Locus HF937054, Accession No. HF937054, "Nicotiana Tabacum mRNA for Heavy Metal ATPase (HM-A gene), strain BB16NN," [online], Bethesda, MD [retrieved on Mar. 12, 2019], Retrieved from the Internet: <URL:https://www.ncbi.nlm.nih.gov/nuccore, HF937054.1, 3 pages.
Arnould et al., "The I-CreI meganuclease and its engineered derivatives: applications from cell modification to gene therapy", *Protein Eng Des Sel.* 24(1-2):27-31, 2011.
Banci et al., "Solution structures of the actuator domain of ATP7A and ATP7B, the Menkes and Wilson disease proteins", Biochemistry 48(33): 7849-7855, 2009.
Bortesi et al., "The CRISPR/Cas9 system for plant genome editing and beyond", *Biotechnol Adv.* 33(1):41-52, 2015.
Chen et al., "Targeted genome modification technologies and their applications in crop improvements", *Plant Cell Rep.* 33(4):575-583, 2014.
Chen et al., "Progress in TILLING as a tool for functional genomics and improvement of crops", *J Integr Plant Biol.* 56(5):425-443, 2014.
Dey et al., "Structure and promoter/leader deletion analysis of mirabilis mosaic virus (MMV) full-length transcript promoter in transgenic plants" *Plant Mol Biol.* 40(5):771-82, 1999.
Fricano et al. "Molecular diversity, population structure, and linkage disequilibrium in a worldwide collection of tobacco (*Nicotiana tabacum* L.) germplasm", *BMC Genet.* 13:18. doi: 10.1186/1471-2156-13-18, 2012.
Gravot et al., "AtHMA3, a plant P1B-ATPase, functions as a Cd/Pb transporter in yeast", *FEBS Lett.* 561(1-3):22-28, 2014.
Hermand et al. ,"Inactivation of two newly identified tobacco heavy metal ATPases leads to reduced Zn and Cd accumulation in shoots and reduced pollen germination", *Metallomics*, 6(8), 1427-1440, 2014.
Horsch et al., A Simple and General Method for Transferring Genes into Plants. Science, 227, 1229-1231, 1985.
Hussain et al., "P-type ATPase heavy metal transporters with roles in essential zinc homeostasis in Arabidopsis", *Plant Cell*, 16(5), 1327-1339, 2004.
Kim et al., "TopHat2: accurate alignment of transcriptomes in the presence of insertions, deletions and gene fusions", *Genome Biology* 14:R36, 2013.
Korenkov et al., "Root-selective expression of AtCAX4 and AtCAX2 results in reduced lamina cadmium in field-grown *Nicotiana tabacum* L.", *Plant Biotechnol J* 7(3):219-226, 2009.
Lewis et al., "Impact of alleles at the Yellow Burley (Yb) loci and nitrogen fertilization rate on nitrogen utilization efficiency and tobacco-specific nitrosamine (TSNA) formation in air-cured tobacco", *J Agric Food Chem.* 60, 6454-6461, 2012.
Liedschulte et al., "Impairing Both HMA4 Homeologs in Required for Cadmium Reduction in Tobacco", *Plant Cell and Environment*, vol. 40, No. 3, Jan. 27, 2017 (pp. 364-377).
Liedschulte et al., "Missense or nonsense mutations in either HMA4.1 or HMA4.2 do not significantly reduce cadmium content in the leaves of tobacco plants grown under field conditions", Poster session presented at: The 12th Solanaceae conference; Oct. 25-29, 2015; Bordeaux, France.
Lugon-Moulin et al., "Cd concentration in tobacco (*Nicotiana tabacum* L.) from different countries and its relationship with other elements", *Chemosphere* 63, 1074-1086, 2006.
Morel et la., "AtHMA3, a PIB-ATPase allowing Cd/Zn/Co/Pb vacuolar storage in *Arabidopsis*", *Plant Physiol.*, 149(2),894-904, 2009.
Ng, P.C et al., "SIFT: Predicting amino acid changes that affect protein function", *Nucleic Acids Res.* 31(13):3812-4, 2003.
Petolino et al., "Genome editing in plants via designed zinc finger nucleases", *In Vitro Cell Dev Biol Plant.* 51(1):1-8, 2015.
Puchta et al., "Gene targeting in plants: 25 years later", *Int J Dev Biol.* 57(6-8):629-37, 2013.
Qiwei, et al., "Research progress of genome editing and derivative technologies in plants", *Yi Chuan.* 37(10):953-973, 2015.
Schneider et al., "NIH Image to ImageJ: 25 years of image analysis", *Nature Methods*, 9, 671-675, 2012.
Sierro et al., "The tobacco genome sequence and its comparison with those of tomato and potato", *Nature Communications* 5, Article No. 3833, 2013.
Thompson et al., "ClustalW: Improving the Sensitivity of Progressive Multiple Sequence Alignment Through Sequence Weighting, Position-Specific Gap Penalties and Weight Matrix Choice", *Nucleic Acids Research* (1994) 22, 4673-4680.
Thompson et al., "The Clustal_X Windows Interface: Flexible Strategies for Multiple Sequence Alignment Aided by Quality Analysis Tools", *Nucleic Acids Research* (1997), 24, 4876-4882).
Trapnell et al., "Differential analysis of gene regulation at transcript resolution with RNA-seq", *Nature Biotechnology* 31: 46-53, 2013.
Wemsman et al., 1987. Chapter Seventeen. Tobacco. pp. 669-698 In: Cultivar Development. Crop Species. W. H. Fehr (ed.), MacMillan Publishing Co, Inc., New York, N.Y 761 pp.).
Wong, et al., "HMA P-type ATPases are the major mechanism for root-to-shoot Cd translocation in *Arabidopsis thaliana*", *New Phytol.*, 181(1), 71-78, 2009.
Wright et al., "TALEN-mediated genome editing: prospects and perspectives", *Biochem J.* 462(1): 15-24, 2014.

\* cited by examiner

SEQUENCE LISTING

```
<160> NUMBER OF SEQ ID NOS: 64

<210> SEQ ID NO 1
<211> LENGTH: 1403
<212> TYPE: PRT
<213> ORGANISM: Nicotiana tabacum

<400> SEQUENCE: 1

Met Val Glu Ser Glu Lys Met Asn Glu Thr Lys Lys Leu Ser Lys Ser
1               5                   10                  15

Tyr Phe Asp Val Leu Gly Ile Cys Cys Thr Ser Glu Val Val Leu Val
            20                  25                  30

Glu Lys Ile Leu Lys Asn Leu Glu Gly Val Lys Glu Val Ser Val Ile
        35                  40                  45
```

```
Val Thr Thr Lys Thr Val Ile Val Ile His Asp Ser Leu Leu Ile Ser
 50                  55                  60

Pro Gln Gln Ile Val Lys Ala Leu Asn Gln Ala Arg Leu Glu Ala Ser
 65                  70                  75                  80

Ile Arg Val Lys Gly Glu Lys Asn Tyr Gln Lys Lys Trp Pro Ser Pro
                 85                  90                  95

Phe Ala Ile Gly Ser Gly Ile Leu Leu Gly Leu Ser Phe Leu Lys Tyr
                100                 105                 110

Phe Phe Ala Pro Phe Gln Trp Leu Ala Leu Ala Ala Val Ala Val Gly
            115                 120                 125

Ile Pro Pro Ile Ile Phe Arg Gly Val Ala Ala Val Arg Asn Leu Thr
130                 135                 140

Leu Asp Ile Asn Ile Leu Val Leu Ile Ala Val Ala Gly Ser Ile Val
145                 150                 155                 160

Leu His Asp Tyr Trp Glu Ala Gly Thr Ile Val Phe Leu Phe Ala Ile
                165                 170                 175

Ala Glu Trp Leu Glu Ser Arg Ala Ser His Lys Ala Thr Ala Ala Met
            180                 185                 190

Ser Ser Leu Val Asn Ile Val Pro Pro Thr Ala Val Leu Ala Glu Ser
        195                 200                 205

Gly Glu Val Val Asn Val Asp Glu Val Lys Val Asn Ser Ile Leu Ala
210                 215                 220

Val Lys Ala Gly Glu Thr Ile Pro Ile Asp Gly Val Val Glu Gly
225                 230                 235                 240

Glu Cys Asp Val Asp Glu Lys Thr Leu Thr Gly Glu Ser Phe Pro Val
                245                 250                 255

Ser Lys Gln Arg Asp Ser Thr Val Trp Ala Gly Thr Thr Asn Leu Asn
            260                 265                 270

Gly Tyr Ile Ser Val Lys Thr Thr Ala Leu Ala Glu Asp Cys Ala Val
        275                 280                 285

Ala Arg Met Ala Gln Leu Val Glu Asp Ala Gln Asn Lys Lys Ser Lys
290                 295                 300

Thr Gln Arg Tyr Ile Asp Lys Cys Ala Lys Tyr Tyr Thr Pro Ala Ile
305                 310                 315                 320

Val Ala Ile Ser Ala Ser Leu Ala Ile Val Pro Thr Ala Leu Arg Val
                325                 330                 335

His Asn Arg Asn Glu Trp Tyr Arg Leu Ala Leu Val Thr Leu Val Ser
            340                 345                 350

Ala Cys Pro Cys Ala Leu Val Leu Ser Thr Pro Val Ala Met Cys Cys
        355                 360                 365

Ala Leu Ser Lys Ala Ala Thr Ser Gly Leu Leu Phe Lys Gly Ala Glu
370                 375                 380

Tyr Leu Glu Thr Leu Ala Lys Ile Lys Ile Met Ala Phe Asp Lys Thr
385                 390                 395                 400

Gly Thr Ile Thr Lys Gly Glu Phe Met Val Thr Glu Phe Lys Ser Leu
                405                 410                 415

Ile Asp Gly Phe Ser Leu Asn Thr Leu Leu Tyr Trp Val Ser Ser Ile
            420                 425                 430

Glu Ser Lys Ser Gly His Pro Met Ala Ala Ala Leu Val Asp Tyr Ala
        435                 440                 445

Gln Ser Asn Ser Val Glu Pro Lys Pro Asp Arg Val Glu Gln Phe Gln
450                 455                 460
```

```
Asn Phe Pro Gly Glu Gly Ile Phe Gly Arg Ile Asp Gly Met Glu Ile
465                 470                 475                 480

Tyr Val Gly Asn Arg Lys Ile Ser Ser Arg Ala Gly Cys Thr Thr Val
            485                 490                 495

Pro Glu Ile Glu Gly Asp Ser Phe Lys Gly Lys Ser Val Gly Tyr Ile
                500                 505                 510

Phe Leu Gly Ser Ser Pro Ala Gly Ile Phe Ser Leu Ser Asp Val Cys
            515                 520                 525

Arg Ile Gly Val Lys Glu Ala Met Arg Glu Leu Lys Gln Met Gly Ile
    530                 535                 540

Lys Thr Ala Met Leu Thr Gly Asp Cys Tyr Ala Ala Ala Asn His Val
545                 550                 555                 560

Gln Asp Gln Leu Gly Gly Ala Leu Asp Glu Phe Gln Ala Glu Leu Leu
                565                 570                 575

Pro Glu Asp Lys Ala Thr Ile Ile Lys Gly Phe Gln Lys Glu Ala Pro
            580                 585                 590

Thr Ala Met Ile Gly Asp Gly Leu Asn Asp Ala Pro Ala Leu Ala Thr
                595                 600                 605

Ala Asp Ile Gly Ile Ser Met Gly Ile Ser Gly Ser Ala Leu Ala Lys
    610                 615                 620

Glu Thr Gly His Val Ile Leu Met Thr Asn Asp Ile Gly Arg Ile Pro
625                 630                 635                 640

Lys Ala Ala Arg Leu Ala Arg Arg Val Arg Lys Ile Val Glu Asn
                645                 650                 655

Met Ile Ile Ser Val Val Thr Lys Ala Ala Ile Val Ala Leu Ala Ile
                660                 665                 670

Ala Gly Tyr Pro Leu Val Trp Ala Ala Val Leu Ala Asp Thr Gly Thr
                675                 680                 685

Cys Leu Leu Val Ile Leu Asn Ser Met Leu Leu Leu Arg Gly Gly Thr
            690                 695                 700

Arg Arg His Gly Lys Lys Cys Trp Arg Ser Ser Thr Pro Ser His Ala
705                 710                 715                 720

Pro His His Lys Asp Lys Ala Ser Cys Cys Lys Ser Glu Asn Ala Pro
                725                 730                 735

Gln Leu Cys Cys Ser Asp Ile Glu Ser Gln Lys Lys Cys Thr Ser Gln
            740                 745                 750

Ser Cys Ser Ser Glu Val Cys Val Pro Arg Cys Gln Pro Val Ser Ser
            755                 760                 765

Gly Ser Lys Ser Cys Gly Asn Asn Gln Cys Pro Asp Ser Ile Glu Asn
770                 775                 780

Ser Gly Phe His Ser His Arg Arg Pro Gln Cys Cys Ser Ser Lys Met
785                 790                 795                 800

Ala Ala Lys Ala Cys Gln Ser Ala Val Ser Glu Ser Lys Ser Cys Gly
                805                 810                 815

Asn Asn Gln Cys Pro Asp Ser Val Glu Asn Ser Gly Phe His Ser His
            820                 825                 830

Pro Arg Pro Glu Cys Cys Ser Ser Lys Met Ala Ala Lys Ala Cys Gln
            835                 840                 845

Ser Ala Val Ser Glu Ser Lys Ser Cys Gly Asn Asn Gln Cys Pro Asp
    850                 855                 860

Ser Val Glu Asn Ser Gly Phe His Ser His Pro Arg Pro Gln Cys Cys
865                 870                 875                 880
```

```
Ser Ser Lys Met Ala Ala Lys Ala Gly Gln Ser Ala Leu Ser Glu Ser
            885                 890                 895
Lys Ser Cys Gly Asn Asn Cys Ser Asp Ser Ile His Lys Ser Asn
        900                 905                 910
Cys His Ser Leu Thr Asn Ser Leu Val Cys Ser Ser Lys Met Ser Ala
            915                 920                 925
Pro Gln Cys His Ser Ala Thr Ser Ser Asn Lys Ser Cys Gly Ser Thr
    930                 935                 940
Lys Cys Ser Asp Phe Ser Asp Lys Lys Cys Cys Gln Ser Asp Lys Ile
945                 950                 955                 960
Pro Gln Thr Cys Ser Thr Lys Lys Ser Ala Pro Gly Cys Gln Ser Ala
                965                 970                 975
Val Ser Gly Ser Lys Ser Cys Gly Asn Ser Lys Cys Ser Asp Ser Lys
            980                 985                 990
Asp Asn Ser Ser His Pro Ser His  Pro Asp His Gln Thr  Cys Met Ser
            995                 1000                1005
Lys Leu  Cys Ala Pro Gln Ser  Gln Ser Ala Thr Ser  Ser Ser Arg
    1010                1015                1020
Thr Cys  Gly Asn Thr Lys Cys  Ser Asp Thr Asn Ser  Lys Asn Ser
    1025                1030                1035
Cys Tyr  Ser Gln Thr Asn Ser  Glu Ser Cys Ser Ser  Lys Met Ser
    1040                1045                1050
Gly Pro  Ser Cys Lys Thr Ala  Asn Ser Gly Ser Arg  Ser Cys Arg
    1055                1060                1065
Asn Lys  Lys Cys Gln Asp Ser  Ala Thr Glu Asn Ser  Phe His Ser
    1070                1075                1080
Pro Leu  Thr Asn Pro Leu Ser  Gly Glu Lys Leu Ser  Glu Gln Lys
    1085                1090                1095
Ser Leu  Asp Leu Val Arg Lys  Asp Lys Glu Ser Ser  His Asp Leu
    1100                1105                1110
Arg His  Gly Cys Ser Asp Glu  Glu His Asp His Thr  Asn Leu Asp
    1115                1120                1125
Lys Ala  Tyr Asp Ser Cys Ala  Leu Gln Glu Cys Cys  Tyr Ser Val
    1130                1135                1140
Gln Gly  Asn Lys Thr Asp Val  Ser Glu Thr Gly Ile  Gln Glu Thr
    1145                1150                1155
Ala His  Cys Asp Ser Thr Asn  Gln Thr Cys Gln Thr  Ala Ser Ser
    1160                1165                1170
Gly Ser  Met Thr Cys Gly Asn  Asp Lys Ile Leu Asp  Ser Leu Ser
    1175                1180                1185
Ile His  Gly Cys His Ser His  Asp Asn Pro Leu His  Glu Glu Asn
    1190                1195                1200
Asn Leu  Glu Gln Lys Ile Leu  Asp Val Val Gly Glu  Gly Ile Lys
    1205                1210                1215
Ser Pro  His Ala Val Gly His  Gly Cys Ser Asp Lys  Glu His Asp
    1220                1225                1230
His Ser  His Pro Glu Lys Ala  Tyr Asp Ser Cys Ala  Thr Asp Asp
    1235                1240                1245
Cys Cys  Phe Ser Val Gln Val  His Gly Ile Asp Asp  Val Ser Lys
    1250                1255                1260
Ser Glu  Ile Gln Glu Thr Ala  His Cys Asp Ser Thr  Lys Gln Ser
    1265                1270                1275
```

```
Met Val Ile Ser Ser Ser Cys Lys His Glu Pro Lys Asp Gln Val
    1280                1285                1290

Asn His Cys Gly Leu His Ser Lys Thr Thr Pro Thr Asp Glu Glu
    1295                1300                1305

Leu Ala Lys Leu Val Arg Arg Cys Cys Lys Tyr Lys Pro Cys His
    1310                1315                1320

Asp Val Arg Ser Gly Cys Arg Lys His Ala Ala Glu Cys Gly Pro
    1325                1330                1335

Thr Val Arg Ser Thr Ile Asn Ile Leu Arg Asp Asn His His His
    1340                1345                1350

Tyr Leu Asp Cys Ser Gly Arg Lys Val Cys Ser Leu Leu Glu Lys
    1355                1360                1365

Arg His Ile Gly Gly Cys Cys Asp Ser Phe Arg Lys Glu Cys Cys
    1370                1375                1380

Ala Lys Lys Lys His Leu Gly Ala Ser Phe Gly Gly Gly Leu Ser
    1385                1390                1395

Glu Ile Val Ile Glu
    1400

<210> SEQ ID NO 2
<211> LENGTH: 1444
<212> TYPE: PRT
<213> ORGANISM: Nicotiana tabacum

<400> SEQUENCE: 2

Met Val Glu Ser Glu Lys Met Asn Asp Thr Lys Asn Leu Ser Lys Ser
1               5                   10                  15

Tyr Phe Asp Val Leu Gly Ile Cys Cys Thr Ser Glu Val Val Leu Val
                20                  25                  30

Glu Lys Ile Leu Lys Asn Leu Glu Gly Val Lys Glu Val Ser Val Ile
            35                  40                  45

Val Thr Thr Lys Thr Val Ile Val Ile His Asp Ser Leu Leu Ile Ser
    50                  55                  60

Gln Gln Gln Ile Val Lys Ala Leu Asn Gln Ala Arg Leu Glu Ala Ser
65                  70                  75                  80

Ile Arg Val Lys Gly Glu Lys Asn Tyr Gln Lys Lys Trp Pro Ser Pro
                85                  90                  95

Phe Ala Ile Gly Ser Gly Ile Leu Leu Gly Leu Ser Phe Leu Lys Tyr
            100                 105                 110

Phe Phe Ala Pro Phe Gln Trp Leu Ala Leu Ala Ala Val Ala Val Gly
        115                 120                 125

Ile Pro Pro Ile Ile Phe Arg Gly Val Ala Ala Val Arg Asn Leu Thr
    130                 135                 140

Leu Asp Ile Asn Ile Leu Val Leu Ile Ala Val Thr Gly Ser Ile Val
145                 150                 155                 160

Leu His Asp Tyr Trp Glu Ala Gly Thr Ile Val Phe Leu Phe Thr Ile
                165                 170                 175

Ala Glu Trp Leu Glu Ser Arg Ala Ser His Lys Ala Thr Ala Ala Met
            180                 185                 190

Ser Ser Leu Val Asn Ile Val Pro Pro Thr Ala Val Leu Ala Glu Ser
        195                 200                 205

Gly Glu Val Val Asn Val Asp Glu Val Lys Leu Asn Ser Ile Leu Ala
    210                 215                 220

Val Lys Ala Gly Glu Thr Ile Pro Ile Asp Gly Val Val Met Glu Gly
225                 230                 235                 240
```

```
Glu Cys Asp Val Asp Glu Lys Thr Leu Thr Gly Ser Phe Pro Val
            245                 250                 255

Ser Lys Gln Ile Asp Ser Thr Val Trp Ala Gly Thr Asn Leu Asn
            260                 265                 270

Gly Tyr Ile Ser Val Lys Thr Thr Ala Leu Ala Glu Asp Cys Ala Val
            275                 280                 285

Ala Arg Met Ala Gln Leu Val Glu Asp Ala Gln Asn Lys Lys Ser Lys
            290                 295                 300

Thr Gln Arg Tyr Ile Asp Lys Cys Ala Lys Tyr Tyr Thr Pro Ala Ile
305                 310                 315                 320

Val Ala Ile Ser Ala Ser Leu Ala Ile Val Pro Thr Ala Leu Arg Val
            325                 330                 335

His Asn Arg Asn Glu Trp Tyr Arg Leu Ala Leu Val Thr Leu Val Ser
            340                 345                 350

Ala Cys Pro Cys Ala Leu Val Leu Ser Thr Pro Val Ala Met Cys Cys
            355                 360                 365

Ala Leu Ser Lys Ala Ala Thr Ser Gly Leu Leu Phe Lys Gly Ala Glu
            370                 375                 380

Tyr Leu Glu Thr Leu Ala Lys Ile Lys Ile Met Ala Phe Asp Lys Thr
385                 390                 395                 400

Gly Thr Ile Thr Arg Gly Glu Phe Met Val Thr Glu Phe Lys Ser Leu
            405                 410                 415

Val Asp Gly Leu Gly Leu Asn Thr Leu Leu Tyr Trp Val Ser Ser Ile
            420                 425                 430

Glu Ser Lys Ser Gly His Pro Met Ala Ala Ala Leu Val Asp Tyr Ala
            435                 440                 445

Gln Ser Asn Ser Val Glu Pro Lys Pro Asp Arg Val Glu Gln Phe Gln
            450                 455                 460

Asn Phe Pro Gly Glu Gly Ile Phe Gly Arg Ile Asp Gly Met Glu Ile
465                 470                 475                 480

Tyr Val Gly Asn Arg Lys Ile Ser Ser Arg Ala Gly Cys Thr Thr Val
            485                 490                 495

Pro Glu Ile Glu Gly Asp Ser Phe Gln Gly Lys Ser Val Gly Tyr Ile
            500                 505                 510

Phe Leu Gly Ser Ser Pro Ala Gly Ile Phe Gly Leu Ser Asp Val Cys
            515                 520                 525

Arg Ile Gly Val Lys Glu Ala Met Arg Glu Leu Lys Gln Met Gly Ile
530                 535                 540

Lys Thr Ala Met Leu Thr Gly Asp Cys Tyr Ala Ala Ala Asn His Val
545                 550                 555                 560

Gln Asp Gln Leu Gly Gly Ala Met Asp Glu Phe Gln Ala Glu Leu Leu
            565                 570                 575

Pro Glu Asp Lys Ala Thr Ile Ile Lys Gly Phe Gln Lys Glu Ala Pro
            580                 585                 590

Thr Ala Met Ile Gly Asp Gly Leu Asn Asp Ala Pro Ala Leu Ala Thr
            595                 600                 605

Ala Asp Ile Gly Ile Ser Met Gly Ile Ser Gly Ser Ala Leu Ala Lys
            610                 615                 620

Glu Thr Gly His Val Ile Leu Met Thr Asn Asp Ile Gly Arg Ile Pro
625                 630                 635                 640

Lys Ala Ala Arg Leu Ala Arg Arg Val Arg Arg Lys Ile Val Glu Asn
            645                 650                 655
```

```
Met Ile Ile Ser Val Val Thr Lys Ala Ala Ile Val Ala Leu Ala Ile
                660                 665                 670

Ala Gly Tyr Pro Leu Val Trp Ala Ala Val Leu Ala Asp Thr Gly Thr
            675                 680                 685

Cys Leu Leu Val Ile Leu Asn Ser Met Leu Leu Arg Val Gly Thr
690                 695                 700

His Arg His Gly Lys Lys Cys Cys Arg Ser Ala Thr Pro Ser His Ala
705                 710                 715                 720

Pro Asn His Lys Asp Lys Ala Ser Cys Cys Lys Ser Glu Asn Ala Pro
                725                 730                 735

Gln Leu Cys Cys Ser Asp Ile Glu Ser Gln Lys Lys Cys Thr Ser Gln
            740                 745                 750

Ser Cys Ser Ser Glu Val Cys Val Pro Arg Cys Gln Pro Val Ser Ser
        755                 760                 765

Gly Ser Lys Ser Cys Gly Asn Asn Gln Cys Pro Asp Ser Val Glu Asn
    770                 775                 780

Ser Gly Phe His Ser His Pro Arg Pro Gln Cys Cys Ser Ser Lys Met
785                 790                 795                 800

Ala Ser Lys Ala Cys Gln Ser Ala Val Ser Glu Ser Lys Ser Cys Gly
                805                 810                 815

Asn Asn Gln Cys Pro Asp Ser Val Glu Asn Ser Gly Phe His Ser His
            820                 825                 830

Pro Arg Pro Gln Cys Cys Ser Ser Lys Met Ala Ser Lys Ala Cys Gln
        835                 840                 845

Ser Ala Val Ser Glu Ser Lys Ser Cys Gly Asn Asn Gln Cys Pro Asp
    850                 855                 860

Ser Val Glu Asn Ser Gly Phe His Ser His Pro Arg Pro Gln Cys Cys
865                 870                 875                 880

Ser Leu Lys Met Ala Ser Lys Ala Cys Gln Ser Ala Val Ser Glu Ser
                885                 890                 895

Lys Ser Cys Gly Asn Asn Gln Cys Pro Asp Ser Val Glu Asn Ser Gly
            900                 905                 910

Phe His Ser His Pro Arg Pro Gln Cys Cys Ser Ser Lys Met Ala Ala
        915                 920                 925

Lys Ala Cys Gln Ser Ala Val Ser Glu Ser Lys Ser Cys Gly Asn Asn
    930                 935                 940

Asn Cys Ser Glu Ser Ile Tyr Lys Ser Ser Cys His Ser Leu Thr Ser
945                 950                 955                 960

Ser Leu Val Cys Ser Ser Lys Met Ser Ala Pro Gln Cys His Ser Ala
                965                 970                 975

Thr Ser Ser Ser Lys Ser Cys Gly Ser Thr Lys Cys Ser Asn Phe Ser
            980                 985                 990

Asp Lys Lys Cys Cys Gln Tyr Asp Lys Ile Pro Gln Thr Cys Ser Thr
        995                 1000                1005

Lys Lys Ser Ala Pro Gly Cys Gln Ser Ala Val Ser Gly Ser Lys
    1010                1015                1020

Ser Cys Gly Asp Ser Lys Cys Ser Asp Ser Lys Asp Asn Ser Ser
    1025                1030                1035

His Pro Ser His Pro Asp His Gln Ile Cys Thr Ser Lys Leu Cys
    1040                1045                1050

Ala Pro Gln Ser Gln Ser Ala Thr Ser Ser Ser Arg Thr Cys Gly
    1055                1060                1065
```

```
Asn Met Lys Cys Ser Asp Thr Asn Ser Lys Asn Ser Cys Tyr Ser
    1070            1075            1080

His Thr Asn Ser Glu Ser Cys Ser Ser Lys Met Ser Gly Pro Ala
    1085            1090            1095

Cys Lys Thr Ala Asn Ser Gly Ser Arg Leu Cys Gly Asn Lys Lys
    1100            1105            1110

Cys Leu Asp Ser Ala Asn Glu Asn Ser Phe His Ser Leu Thr Asn
    1115            1120            1125

Pro Leu Cys Glu Glu Lys Leu Leu Glu Lys Glu Ser Leu Asp Leu
    1130            1135            1140

Ala Arg Lys Asp Arg Glu Ser Asn His Asp Leu Ser His Gly Cys
    1145            1150            1155

Ser Asp Glu Glu His Asp His Leu Asn Leu Asp Lys Ala His Asp
    1160            1165            1170

Ser Cys Ala Leu Gln Glu Cys Cys Tyr Ser Val Gln Gly Asn Lys
    1175            1180            1185

Thr Asp Val Ser Glu Thr Gly Ile Gln Glu Ala Ala His Cys Asp
    1190            1195            1200

Ser Ile Asn Gln Thr Cys Gln Thr Ala Ile Ser Gly Ser Met Thr
    1205            1210            1215

Cys Gly Asn Asn Lys Ser Leu Asp Ser Leu Ser Ile His Gly Cys
    1220            1225            1230

His Ser His Asp Ser Pro Leu His Lys Glu Ser Asn Leu Glu Gln
    1235            1240            1245

Lys Ser Leu Asp Val Ala Gly Glu Gly Ile Lys Ser Pro His Ala
    1250            1255            1260

Val Gly Gln Gly Cys Ser Asp Lys Glu His Asn His Ser His Pro
    1265            1270            1275

Glu Lys Ala Tyr Asp Ser Cys Ala Thr Asp Asp Cys Cys Phe Ser
    1280            1285            1290

Val Gln Val His Gly Ile Asp Asp Val Ser Arg Ser Glu Ile Gln
    1295            1300            1305

Glu Thr Ala His Cys Asp Ser Thr Lys Gln Ser Thr Val Ile Pro
    1310            1315            1320

Ser Ser Cys Glu His Glu Pro Lys Asp Gln Val Asn His Cys Gly
    1325            1330            1335

Ser His Ser Lys Ser Ile Pro Thr Asp Glu Glu Leu Ala Lys Leu
    1340            1345            1350

Val Arg Arg Cys Cys Lys Tyr Lys Pro Cys His Asp Val Arg Ser
    1355            1360            1365

Gly Cys Arg Lys His Ala Ala Glu Cys Gly Pro Thr Val Arg Ser
    1370            1375            1380

Thr Ile Asn Ile Leu Arg Asp Asn His His His Leu Asp Cys
    1385            1390            1395

Ser Gly Arg Lys Val Cys Ser Leu Leu Glu Lys Arg His Ile Gly
    1400            1405            1410

Gly Cys Cys Asp Ser Phe Arg Lys Glu Cys Cys Ala Lys Asn Asn
    1415            1420            1425

His Leu Gly Ala Ser Phe Gly Gly Gly Leu Ser Glu Ile Val Ile
    1430            1435            1440

Glu
```

<210> SEQ ID NO 3
<211> LENGTH: 4246
<212> TYPE: DNA
<213> ORGANISM: Nicotiana tabacum

<400> SEQUENCE: 3

| | | | | | |
|---|---|---|---|---|---|
| agagaaggag | aaaaatggtg | gaaagtgaaa | aaatgaatga | aacaaagaag | ttgagcaaga | 60 |
| gctattttga | tgttttggga | atttgctgta | cttcagaagt | tgttctagtt | gaaaaaattc | 120 |
| tcaagaatct | tgaagggtt | aaagaggttt | cagtaattgt | cacaacaaag | actgtcattg | 180 |
| ttattcatga | ttctcttctc | atttctccgc | aacaaattgt | taaagcattg | aatcaagcaa | 240 |
| gattagaagc | aagcataaga | gtgaaaggag | agaaaaacta | ccaaagaaa | tggccaagtc | 300 |
| catttgcaat | tggcagtgga | atattgcttg | gactctcatt | tttgaagtac | ttttttgcac | 360 |
| ctttccaatg | gttagcactt | gcagctgttg | cagttgggat | tcctccaatt | attttagag | 420 |
| gtgtggctgc | cgtgcgaaac | ctcactcttg | acatcaacat | tcttgtttta | atagcagtgg | 480 |
| ctggatcaat | tgttttacac | gattattggg | aagctggtac | tattgtcttc | ttattcgcca | 540 |
| ttgcagaatg | gctagagtca | agggcaagtc | acaaggctac | cgctgctatg | tcatcactgg | 600 |
| tcaatatagt | ccctccaaca | gcagttttag | ctgaaagcgg | agaagtcgta | aatgttgatg | 660 |
| aagtcaaggt | gaatagcatt | cttgctgtga | aagctggtga | aactatacct | attgatggag | 720 |
| ttgtagtgga | agggaatgt | gacgtggacg | agaaaacact | gacaggcgag | tcgtttccag | 780 |
| tttctaagca | aagagattca | acggtctggg | ctggcactac | aaatctaaat | ggctatatca | 840 |
| gtgttaagac | tacggctttg | gctgaagatt | gtgcggtggc | taggatggca | cagcttgtcg | 900 |
| aagatgctca | gaacaagaaa | tcaaaaaccc | aaagatacat | cgacaagtgt | gctaaatatt | 960 |
| atacaccagc | aattgtggct | atatcagctt | ctttggcaat | tgttcctact | gcattaagag | 1020 |
| ttcacaatcg | aaatgaatgg | tatcgcttgg | cttttggtcac | attggtgagt | gcatgtccgt | 1080 |
| gtgcacttgt | tctatctaca | ccagttgcca | tgtgttgcgc | actttcaaaa | gcagcaacgt | 1140 |
| ccggtcttct | gtttaaagga | gcagagtacc | ttgagactct | agctaaaatc | aaaatcatgg | 1200 |
| cttttgacaa | aacagggact | ataactaaag | gagaatttat | ggtgaccgag | ttcaagtctc | 1260 |
| tgattgatgg | ttttagtctc | aatacactgc | tttactgggt | ttcaagcatt | gagagcaagt | 1320 |
| caggtcatcc | gatggcagcc | gctctggtgg | actatgcaca | atcaaattcc | gttgagccaa | 1380 |
| agcctgatag | agttgagcag | tttcaaaatt | ttcctggtga | agggatattt | ggaagaattg | 1440 |
| atggaatgga | aatctatgtc | gggaatagga | aaatttcttc | aagagctgga | tgtaccacag | 1500 |
| taccagaaat | agagggtgat | agtttcaaag | gaaagtctgt | tggatacata | tttttgggat | 1560 |
| catctccagc | tggaattttc | agtctttccg | atgtttgtcg | aattggtgta | aaagaagcaa | 1620 |
| tgagagaact | gaagcagatg | ggtatcaaaa | ccgcgatgct | tactggtgat | tgttatgcag | 1680 |
| ctgccaacca | tgtgcaggat | cagttaggtg | gagctttgga | tgaatttcaa | gcagaactcc | 1740 |
| taccagagga | caaggcaaca | atcatcaagg | ttttcagaa | ggaagctcca | acagcgatga | 1800 |
| taggcgacgg | ccttaatgat | gctcctgcat | tagcaacagc | tgacattggc | atctcaatgg | 1860 |
| gcatctctgg | gtcagctctc | gctaaagaaa | caggccatgt | tatactaatg | acaaatgaca | 1920 |
| tcggaagaat | accgaaagct | gcacgtcttg | ctagaagagt | tcgaaggaag | attgttgaga | 1980 |
| atatgattat | atcagtcgtt | acaaggctg | ccatagttgc | attggcaata | gcaggttatc | 2040 |
| cattggtttg | gctgctgtc | ctcgcagata | ctgggacatg | cttgctagtg | attttgaaca | 2100 |
| gcatgctact | tctacgagga | ggcacacgca | gacatgggaa | aaaatgttgg | agatcttcta | 2160 |

```
ctccttcgca tgctccccac cacaaagaca aagcttcatg ttgcaagtcg gaaaatgctc    2220
cccagctgtg ttgctctgat attgagtcac aaaagaaatg tacaagtcaa tcatgctcgt    2280
ccgaggtgtg tgttccaaga tgtcaacctg tctcctcagg atcaaagtca tgtggaaata    2340
atcagtgccc agactccatt gaaaatagtg gttttcattc tcatcgccgt cctcaatgct    2400
gctcgtcgaa gatggctgct aaagcatgcc aatctgcagt ttcagaatca agtcatgcg    2460 gaaataatca gtgcccagac tccgttgaaa atagtggttt tcattctcat ccccgtcctg    2520
aatgctgctc gtcgaagatg gctgctaaag cgtgccaatc tgcagtttca gaatcaaagt    2580
catgtggaaa taatcagtgc ccagactccg ttgaaaatag tggttttcat tctcatcccc    2640
gtcctcaatg ctgttcatcg aagatggctg ctaaagcagg ccaatctgca ctttcagaat    2700
caaagtcatg tggaaataac aattgctcag actccattca aagagtaat tgtcattctt    2760 taactaactc tctagtatgt tcttccaaga tgtctgctcc acaatgtcat tctgctactt    2820
caagcaacaa atcatgtgga agtaccaagt gctccgactt cagtgacaaa aatgttgtc    2880 aatccgacaa aattcctcaa acgtgctcta ccaagaagtc tgctccagga tgtcaatctg    2940
cagtttctgg gtctaaatca tgtggaaata gcaagtgttc agactcaaaa gacaatagta    3000
gccatccttc acatcccgat catcaaacat gcatgtctaa gttgtgtgct ccacaaagcc    3060
aatctgcaac ttcaagctcc aggacatgtg gaaatacaaa gtgctcggac accaatagca    3120
agaattcttg ttattcacaa accaactctg aatcatgctc ttcaaagatg tctggtccat    3180
catgcaaaac tgctaattca ggttcaaggt catgcagaaa taagaagtgc caggactctg    3240
caaccgagaa cagttttcat tcaccactta ctaatccact cagtggggaa aagctttcgg    3300
agcagaaaag cttggattta gtccgaaaag ataaggaatc aagtcatgat cttcgtcatg    3360
gctgctctga cgaggaacat gatcatacaa atttagacaa ggcatatgac agttgtgcct    3420
tacaagaatg ttgttattcg gttcaaggca ataaaactga tgtatcagaa actggaatcc    3480
aggaaactgc tcattgtgac agcaccaatc aaacatgcca aactgcaagt tcaggatcga    3540
tgacatgcgg aaatgataag atcctggact ctctaagcat ccatggttgt cattcgcatg    3600
ataatccact ccacgaggag aacaacttgg agcagaaaat cttggatgtt gttggagaag    3660
gtataaaatc acctcatgct gtcggtcatg gctgttcgga caaggaacac gatcactcac    3720
atccagaaaa ggcatatgac agttgtgcaa cagatgattg ttgtttttca gttcaagtcc    3780
atggcattga cgacgtatca aaagtgaaa ttcaagaaac tgctcattgt gacagcacaa    3840
agcagagcat ggtcatctcc agcagctgca acatgaacc aaaagatcag gtaaatcact    3900
gtggacttca ctctaaaact actccaactg atgaagaact agccaagctg gttagaagat    3960
gctgcaaata caaccatgc cacgacgtcc gttctggctg caggaagcat gctgcagaat    4020
gtggtccaac cgttcgatca accatcaata tcttacggga caaccatcat cattacctag    4080
actgcagtgg tcgtaaggtt tgttcgctgt tggagaagag acacatcggt ggatgctgtg    4140
acagcttcag aaaagaatgt tgtgccaaga aaaacaccct tggagcaagt tttggaggag    4200
gtttatcaga aattgtcata gagtagatgc aatccgaagt gtacat                   4246
```

<210> SEQ ID NO 4
<211> LENGTH: 4376
<212> TYPE: DNA
<213> ORGANISM: Nicotiana tabacum

<400> SEQUENCE: 4

```
atagaaagaa gagaatggtg gaaagtgaga aaatgaatga cacaaagaat ctgagcaaga      60
gctattttga tgttttggga atttgctgta cttcagaagt tgttcttgtt gaaaaaattc     120
tcaagaatct tgaaggggtt aaagaggttt cagtaattgt cacaacaaag actgtcattg     180
ttattcatga ttctctcctc atttctcagc aacaaattgt taaagcattg aatcaagcaa     240
gattagaagc aagtataaga gtgaaaggag agaaaaacta ccaaagaaa tggccaagtc      300
catttgcaat tggcagtgga atattgcttg gactctcatt tttgaagtac ttttttgcac     360
cttttccaatg gttagcactt gcagctgttg cagttgggat tcctccaatt attttaggg    420
gtgtggctgc cgtgcgaaac ctcactcttg acatcaacat tcttgtttta atagcagtga    480
cgggatcaat tgttttacac gattattggg aagctggtac tattgtcttc ttattcacca    540
ttgcagaatg gctagagtca agggcaagtc acaaggctac tgctgctatg tcatcactgg    600
tcaatatagt ccctccaaca gcagttttag ctgaaagtgg agaagtcgta atgttgatg     660
aagtcaagtt gaatagcatt cttgctgtta aagctggtga actatacct attgatggag     720
ttgtaatgga aggggaatgt gacgtggacg agaaaacact gacaggcgag tcgtttccag    780
tttctaagca aatagattca acggtctggg ctggcactac aaatctaaat ggctatatca    840
gtgttaagac tacggctttg gctgaagatt gtgcggtggc taggatggcg cagcttgtcg    900
aagatgctca gaacaagaaa tcaaaaaccc aaagatacat tgacaagtgt gctaaatatt    960
atacaccagc aattgtggct atatcagctt ctttggcaat agttcctact gcattaagag   1020
ttcacaatcg aaatgagtgg tatcgcttgg cttttggtcac gttggtgagt gcatgtccgt   1080
gtgcacttgt gctatctaca ccagttgcca tgtgttgtgc actttctaaa gcagcaacgt   1140
ccggtcttct gtttaaagga gcagagtacc ttgagactct tgctaaaatc aaaatcatgg   1200
cttttgacaa aacagggact ataactagag gagaatttat ggtgaccgag ttcaagtctc   1260
tggttgatgg tcttggtctc aatacactgc tttactgggt ttcaagtatt gagagcaagt   1320
caggtcatcc gatggcagcc gctctggttg actatgcaca atcaaattcc gttgagccaa   1380
agcctgatag agttgagcag tttcaaaatt ttcctggtga agggatattt ggaagaattg   1440
atggaatgga aatctatgtc gggaatagga aaatttcttc aagagctgga tgtactacag   1500
taccagaaat agagggtgat agtttccaag gaaagtctgt tggatacata ttttgggat    1560
catctcccgc tggaattttc ggtctttccg atgtttgtcg aattggtgta aagaagcaa     1620
tgagagagct gaagcagatg ggtatcaaaa ccgcgatgct tactggtgat tgttatgcag   1680
ctgccaacca tgtgcaggat cagttaggtg gagctatgga tgaatttcaa gcggaactct   1740
taccagagga caaggcaaca atcatcaagg gttttcagaa ggaagctcca acagcgatga   1800
taggcgacgg ccttaatgat gctcctgcat tagcaacagc tgacattggc atctcaatgg   1860
gcatctctgg gtcagctctc gcgaaagaaa caggccatgt tatactaatg acaaatgaca   1920
tcggaagaat accaaaagct gcacgtcttg ctagaagagt tcgaaggaag attgttgaga   1980
atatgattat atcagtcgtt acaaaggccg ccatagttgc attggcaata gcaggttatc   2040
cattggtttg ggctgctgtc ctcgcggata ctgggacatg cttgctagtg atcttgaaca   2100
gcatgctact tctacgagta ggcacacaca gacatgggaa aaaatgttgt agatctgcta   2160
ctccttcgca tgctcccaac cacaaagaca agcttcttg ttgcaagtcg gaaaatgctc     2220
cgcagctgtg ttgctctgat attgagtcac aaaagaaatg tacgagtcaa tcatgctcgt   2280
```

```
ccgaggtgtg tgttccaaga tgtcaacctg tctcctcggg atcaaagtca tgtggaaata    2340
atcagtgccc agactccgtt gaaaatagtg gttttcattc tcatcccgt cctcaatgct     2400 gctcgtcgaa gatggcttct aaagcatgcc aatctgcagt ttcagaatca agtcatgtg     2460 gaaataatca gtgcccagac tccgttgaaa atagtggttt tcattctcat ccccgccctc    2520
aatgctgctc gtctaagatg gcttctaaag catgccaatc tgcagtttca gaatcaaagt    2580
catgtggaaa taatcagtgc ccagactccg ttgaaaatag tggttttcat tctcatcccc    2640
gtcctcaatg ctgctcgttg aagatggctt ctaaagcatg ccaatctgca gtttcagaat    2700
caaagtcatg tggaaataat cagtgccag actccgttga aaatagtggt tttcattctc     2760
atccccgtcc tcaatgctgc tcgtcgaaga tggctgctaa agcatgccaa tctgcagttt    2820
cagaatcaaa gtcatgtgga ataacaatt gctcggagtc catttacaag agtagttgtc     2880
attctttaac aagttctcta gtatgttctt ccaagatgtc tgctccacaa tgtcattctg    2940
ccacttcaag ctccaaatca tgtggaagta ccaagtgctc aacttcagt gacaaaaaat     3000 gttgccaata tgacaaaatt cctcaaacgt gctctaccaa gaagtctgct ccaggatgtc    3060
aatctgcagt ttctgggtct aaatcatgtg gagatagcaa gtgttcagac tcgaaagaca    3120
atagtagcca tccttcacat cccgatcatc aaatatgcac gtctaagttg tgtgctccac    3180
aaagccaatc tgcaacttca agctccagga catgtggaaa tatgaagtgc tcggacacca    3240
atagcaagaa ttcttgttat tcacatacca actctgaatc atgctcttca agatgtctg     3300 gtccagcatg caaaactgct aattcaggtt caaggttatg cggaaataag aagtgcctag    3360
actctgcaaa cgagaacagt tttcattcac ttactaatcc actctgtgag gaaaagcttt    3420
tggagaagga aagcttggat ttagcccgaa aagataggga atcaaatcat gatcttagtc    3480
atggttgctc tgacgaggaa catgatcatc taaatttaga caaggacat gacagttgtg     3540 ccttacaaga atgttgttat tctgttcaag gcaataaaac tgatgtatca gaaactggaa    3600
tccaggaagc tgctcattgt gacagcatca atcaaacatg ccaaactgca atttcaggat    3660
caatgacatg cggaaataat aagagtctgg actctctaag catccatggt tgtcattcac    3720
atgatagtcc actccacaag gagagcaact tggagcagaa aagcttggat gttgctggag    3780
aaggtataaa atcacctcat gctgtcggtc aaggctgttc ggacaaggag cacaatcact    3840
cgcatccaga aaaggcgtat gacagttgtg caacagacga ttgttgtttt tcagttcaag    3900
tccatggcat tgacgacgta tcaagaagtg aaattcaaga aactgctcat tgtgacagca    3960
caaaacagag cacggtcatc cccagcagct gcgaacatga accaaaagat caggtaaatc    4020
actgtggatc tcactctaaa agtattccaa ctgatgaaga actagccaag ctggttagaa    4080
gatgctgcaa atacaaacca tgccacgatg tccgctctgg ctgcaggaag catgctgcag    4140
aatgtggtcc aaccgttcga tcaaccatca atatcttacg ggacaaccat catcatcatc    4200
tagactgcag tggtcgtaag gtttgttcgc tgttggagaa gagacacatt ggtggatgct    4260
gtgacagctt cagaaaagaa tgttgtgcca agaacaatca ccttggagca gttttggag    4320 gaggtttatc agaaattgtc atagagtaga tgcaatctga agtgtacata tgttgt         4376
```

<210> SEQ ID NO 5
<211> LENGTH: 191
<212> TYPE: DNA
<213> ORGANISM: Nicotiana tabacum

<400> SEQUENCE: 5
tgagagcaag tcaggtcatc cgatggcagc cgctctggtg gactatgcac aatcaaattc    60
cgttgagcca agcctgata gagttgagca gtttcaaaat tttcctggtg aagggatatt   120
tggaagaatt gatggaatgg aaatctatgt cgggaatagg aaaatttctt caagagctgg   180
atgtaccaca g                                                        191

<210> SEQ ID NO 6
<211> LENGTH: 139
<212> TYPE: DNA
<213> ORGANISM: Nicotiana tabacum

<400> SEQUENCE: 6
taaatggttg aatcatttct tatgctcata gtagagataa acatcagag ttataattat    60 aagtatatga tttctccagt taattttgct gttagatttt ctttgacctg tttagcacta   120
atgcggtgga tgtttgaat                                                139

<210> SEQ ID NO 7
<211> LENGTH: 23
<212> TYPE: DNA
<213> ORGANISM: Artificial Sequence
<220> FEATURE:
<223> OTHER INFORMATION: HMA4.1-Exon1 forward primer

<400> SEQUENCE: 7
gcatgttctt ataagagaaa ctc                                           23

<210> SEQ ID NO 8
<211> LENGTH: 23
<212> TYPE: DNA
<213> ORGANISM: Artificial Sequence
<220> FEATURE:
<223> OTHER INFORMATION: HMA4.1-Exon1 reverse primer

<400> SEQUENCE: 8
gtgaatttat ttaacaagcc aca                                           23

<210> SEQ ID NO 9
<211> LENGTH: 22
<212> TYPE: DNA
<213> ORGANISM: Artificial Sequence
<220> FEATURE:
<223> OTHER INFORMATION: HMA4.1-Exon2 forward primer

<400> SEQUENCE: 9
ccaaaattgt ttctgcttct cc                                            22

<210> SEQ ID NO 10
<211> LENGTH: 23
<212> TYPE: DNA
<213> ORGANISM: Artificial Sequence
<220> FEATURE:
<223> OTHER INFORMATION: HMA4.1-Exon2 reverse primer

<400> SEQUENCE: 10
cgtcatataa attgggacaa aag                                           23

<210> SEQ ID NO 11
<211> LENGTH: 23
<212> TYPE: DNA
<213> ORGANISM: Artificial Sequence
<220> FEATURE:

<223> OTHER INFORMATION: HMA4.1-Exon4/5 forward primer

<400> SEQUENCE: 11
gtgtctttat tttctcactg ata                                           23

<210> SEQ ID NO 12
<211> LENGTH: 23
<212> TYPE: DNA
<213> ORGANISM: Artificial Sequence
<220> FEATURE:
<223> OTHER INFORMATION: HMA4.1-Exon4/5 reverse primer

<400> SEQUENCE: 12
tagtgacgtg attcataaga caa                                           23

<210> SEQ ID NO 13
<211> LENGTH: 21
<212> TYPE: DNA
<213> ORGANISM: Artificial Sequence
<220> FEATURE:
<223> OTHER INFORMATION: HMA4.1-Exon6 forward primer

<400> SEQUENCE: 13
atcagtcctt tcacttgacc c                                             21

<210> SEQ ID NO 14
<211> LENGTH: 22
<212> TYPE: DNA
<213> ORGANISM: Artificial Sequence
<220> FEATURE:
<223> OTHER INFORMATION: HMA4.1-Exon6 reverse primer

<400> SEQUENCE: 14
aaccattaga gccatttcag aa                                            22

<210> SEQ ID NO 15
<211> LENGTH: 23
<212> TYPE: DNA
<213> ORGANISM: Artificial Sequence
<220> FEATURE:
<223> OTHER INFORMATION: HMA4.1-Exon7/8 forward primer

<400> SEQUENCE: 15
gatactgcaa tacaaaagca cat                                           23

<210> SEQ ID NO 16
<211> LENGTH: 22
<212> TYPE: DNA
<213> ORGANISM: Artificial Sequence
<220> FEATURE:
<223> OTHER INFORMATION: HMA4.1-Exon7/8 reverse primer

<400> SEQUENCE: 16
cacttacttg gtaatacgtt ct                                            22

<210> SEQ ID NO 17
<211> LENGTH: 20
<212> TYPE: DNA
<213> ORGANISM: Artificial Sequence
<220> FEATURE:
<223> OTHER INFORMATION: HMA4.2-Exon1 forward primer

<400> SEQUENCE: 17
ttgctactct gggttgctac                                               20

```
<210> SEQ ID NO 18
<211> LENGTH: 23
<212> TYPE: DNA
<213> ORGANISM: Artificial Sequence
<220> FEATURE:
<223> OTHER INFORMATION: HMA4.2-Exon1 reverse primer

<400> SEQUENCE: 18
tcaagtttaa agtttgcttc tac                                              23

<210> SEQ ID NO 19
<211> LENGTH: 22
<212> TYPE: DNA
<213> ORGANISM: Artificial Sequence
<220> FEATURE:
<223> OTHER INFORMATION: HMA4.2-Exon2 forward primer

<400> SEQUENCE: 19
tgtgcataca taacgtaaat cg                                               22

<210> SEQ ID NO 20
<211> LENGTH: 22
<212> TYPE: DNA
<213> ORGANISM: Artificial Sequence
<220> FEATURE:
<223> OTHER INFORMATION: HMA4.2-Exon2 reverse primer

<400> SEQUENCE: 20
atcaaatacc acataagtag gg                                               22

<210> SEQ ID NO 21
<211> LENGTH: 23
<212> TYPE: DNA
<213> ORGANISM: Artificial Sequence
<220> FEATURE:
<223> OTHER INFORMATION: HMA4.2-Exon4/5 forward primer

<400> SEQUENCE: 21
tttagtcact ttgacataaa tgg                                              23

<210> SEQ ID NO 22
<211> LENGTH: 22
<212> TYPE: DNA
<213> ORGANISM: Artificial Sequence
<220> FEATURE:
<223> OTHER INFORMATION: HMA4.2-Exon4/5 reverse primer

<400> SEQUENCE: 22
aagacagaga acaagttcac at                                               22

<210> SEQ ID NO 23
<211> LENGTH: 20
<212> TYPE: DNA
<213> ORGANISM: Artificial Sequence
<220> FEATURE:
<223> OTHER INFORMATION: HMA4.2-Exon6 forward primer

<400> SEQUENCE: 23
tcagtccttt cgcttgacct                                                  20

<210> SEQ ID NO 24
<211> LENGTH: 20
<212> TYPE: DNA
<213> ORGANISM: Artificial Sequence
<220> FEATURE:
<223> OTHER INFORMATION: HMA4.2-Exon6 reverse primer
```

<400> SEQUENCE: 24
gagaatgtgg tactcgcaag                                                  20

<210> SEQ ID NO 25
<211> LENGTH: 22
<212> TYPE: DNA
<213> ORGANISM: Artificial Sequence
<220> FEATURE:
<223> OTHER INFORMATION: HMA4.2-Exon7/8 forward primer

<400> SEQUENCE: 25
atacattgag gacacataat cg                                               22

<210> SEQ ID NO 26
<211> LENGTH: 21
<212> TYPE: DNA
<213> ORGANISM: Artificial Sequence
<220> FEATURE:
<223> OTHER INFORMATION: HMA4.2-Exon7/8 reverse primer

<400> SEQUENCE: 26
tataccccat tctgaccctt g                                                21

<210> SEQ ID NO 27
<211> LENGTH: 24
<212> TYPE: DNA
<213> ORGANISM: Artificial Sequence
<220> FEATURE:
<223> OTHER INFORMATION: HMA4.1 forward primer

<400> SEQUENCE: 27
tcatgcagaa ataagaagtg ccag                                             24

<210> SEQ ID NO 28
<211> LENGTH: 23
<212> TYPE: DNA
<213> ORGANISM: Artificial Sequence
<220> FEATURE:
<223> OTHER INFORMATION: HMA4.1 reverse primer

<400> SEQUENCE: 28
atggatgctt agagagtcca gga                                              23

<210> SEQ ID NO 29
<211> LENGTH: 25
<212> TYPE: DNA
<213> ORGANISM: Artificial Sequence
<220> FEATURE:
<223> OTHER INFORMATION: HMA4.2 forward primer

<400> SEQUENCE: 29
gttatgcgga ataagaagt gccta                                             25

<210> SEQ ID NO 30
<211> LENGTH: 24
<212> TYPE: DNA
<213> ORGANISM: Artificial Sequence
<220> FEATURE:
<223> OTHER INFORMATION: HMA4.2 reverse primer

<400> SEQUENCE: 30
catggatgct tagagagtcc agac                                             24

<210> SEQ ID NO 31
<211> LENGTH: 24

```
<212> TYPE: DNA
<213> ORGANISM: Artificial Sequence
<220> FEATURE:
<223> OTHER INFORMATION: Actin 9 forward primer

<400> SEQUENCE: 31
ctattctccg ctttggactt ggca                                            24

<210> SEQ ID NO 32
<211> LENGTH: 23
<212> TYPE: DNA
<213> ORGANISM: Artificial Sequence
<220> FEATURE:
<223> OTHER INFORMATION: Actin 9 reverse primer

<400> SEQUENCE: 32
aggacctcag gacaacggaa acg                                             23

<210> SEQ ID NO 33
<211> LENGTH: 14
<212> TYPE: DNA
<213> ORGANISM: Artificial Sequence
<220> FEATURE:
<223> OTHER INFORMATION: HMA4.1 Q293* mutant-probe

<400> SEQUENCE: 33
aggatggcac agct                                                       14

<210> SEQ ID NO 34
<211> LENGTH: 14
<212> TYPE: DNA
<213> ORGANISM: Artificial Sequence
<220> FEATURE:
<223> OTHER INFORMATION: HMA4.1 wild type probe

<400> SEQUENCE: 34
aggatggcac agct                                                       14

<210> SEQ ID NO 35
<211> LENGTH: 35
<212> TYPE: DNA
<213> ORGANISM: Artificial Sequence
<220> FEATURE:
<223> OTHER INFORMATION: HMA4.1 forward primer

<400> SEQUENCE: 35
ctggcactac aaatctaaat ggtagtatag tattt                                35

<210> SEQ ID NO 36
<211> LENGTH: 29
<212> TYPE: DNA
<213> ORGANISM: Artificial Sequence
<220> FEATURE:
<223> OTHER INFORMATION: HMA4.1 reverse primer

<400> SEQUENCE: 36
ctggtgtata atatttagca cacttgtcg                                       29

<210> SEQ ID NO 37
<211> LENGTH: 15
<212> TYPE: DNA
<213> ORGANISM: Artificial Sequence
<220> FEATURE:
<223> OTHER INFORMATION: HMA4.1 E296K mutant-probe
```

```
<400> SEQUENCE: 37
cacagcttgt caaag                                                    15

<210> SEQ ID NO 38
<211> LENGTH: 15
<212> TYPE: DNA
<213> ORGANISM: Artificial Sequence
<220> FEATURE:
<223> OTHER INFORMATION: HMA4.1 wild type probe

<400> SEQUENCE: 38
cacagcttgt cgaag                                                    15

<210> SEQ ID NO 39
<211> LENGTH: 35
<212> TYPE: DNA
<213> ORGANISM: Artificial Sequence
<220> FEATURE:
<223> OTHER INFORMATION: HMA4.1 forward primer

<400> SEQUENCE: 39
ctggcactac aaatctaaat ggtagtatag tattt                              35

<210> SEQ ID NO 40
<211> LENGTH: 29
<212> TYPE: DNA
<213> ORGANISM: Artificial Sequence
<220> FEATURE:
<223> OTHER INFORMATION: HMA4.1 reverse primer

<400> SEQUENCE: 40
ctggtgtata atatttagca cacttgtcg                                     29

<210> SEQ ID NO 41
<211> LENGTH: 19
<212> TYPE: DNA
<213> ORGANISM: Artificial Sequence
<220> FEATURE:
<223> OTHER INFORMATION: HMA4.1 T402I mutant-probe

<400> SEQUENCE: 41
tttgacaaaa cagggatta                                                19

<210> SEQ ID NO 42
<211> LENGTH: 19
<212> TYPE: DNA
<213> ORGANISM: Artificial Sequence
<220> FEATURE:
<223> OTHER INFORMATION: HMA4.1 wild type probe

<400> SEQUENCE: 42
tttgacaaaa cagggacta                                                19

<210> SEQ ID NO 43
<211> LENGTH: 20
<212> TYPE: DNA
<213> ORGANISM: Artificial Sequence
<220> FEATURE:
<223> OTHER INFORMATION: HMA4.1 forward primer

<400> SEQUENCE: 43
ccatgtgttg cgcactttca                                               20

<210> SEQ ID NO 44
```

```
<211> LENGTH: 25
<212> TYPE: DNA
<213> ORGANISM: Artificial Sequence
<220> FEATURE:
<223> OTHER INFORMATION: HMA4.1 reverse primer

<400> SEQUENCE: 44
aactcggtca ccataaattc tcctt                                             25

<210> SEQ ID NO 45
<211> LENGTH: 18
<212> TYPE: DNA
<213> ORGANISM: Artificial Sequence
<220> FEATURE:
<223> OTHER INFORMATION: HMA4.1 G251D mutant-probe

<400> SEQUENCE: 45
agaaaacact gacagacg                                                     18

<210> SEQ ID NO 46
<211> LENGTH: 16
<212> TYPE: DNA
<213> ORGANISM: Artificial Sequence
<220> FEATURE:
<223> OTHER INFORMATION: HMA 4.1 wild type probe

<400> SEQUENCE: 46
aaaacactga caggcg                                                       16

<210> SEQ ID NO 47
<211> LENGTH: 27
<212> TYPE: DNA
<213> ORGANISM: Artificial Sequence
<220> FEATURE:
<223> OTHER INFORMATION: HMA 4.1 forward primer

<400> SEQUENCE: 47
aagtcgtaaa tgttgatgaa gtcaagg                                           27

<210> SEQ ID NO 48
<211> LENGTH: 21
<212> TYPE: DNA
<213> ORGANISM: Artificial Sequence
<220> FEATURE:
<223> OTHER INFORMATION: HMA 4.1 reverse primer

<400> SEQUENCE: 48
cagcccagac cgttgaatct c                                                 21

<210> SEQ ID NO 49
<211> LENGTH: 18
<212> TYPE: DNA
<213> ORGANISM: Artificial Sequence
<220> FEATURE:
<223> OTHER INFORMATION: HMA4.1 V351M mutant-probe

<400> SEQUENCE: 49
ctttggtcac attgatga                                                     18

<210> SEQ ID NO 50
<211> LENGTH: 18
<212> TYPE: DNA
<213> ORGANISM: Artificial Sequence
<220> FEATURE:
<223> OTHER INFORMATION: HMA 4.1 wild type probe
```

```
<400> SEQUENCE: 50
ttggtcacat tggtgagt                                                    18

<210> SEQ ID NO 51
<211> LENGTH: 25
<212> TYPE: DNA
<213> ORGANISM: Artificial Sequence
<220> FEATURE:
<223> OTHER INFORMATION: HMA 4.1 forward primer

<400> SEQUENCE: 51
ggctatatca gcttctttgg caatt                                            25

<210> SEQ ID NO 52
<211> LENGTH: 26
<212> TYPE: DNA
<213> ORGANISM: Artificial Sequence
<220> FEATURE:
<223> OTHER INFORMATION: HMA 4.1 reverse primer

<400> SEQUENCE: 52
aacacatggc aactggtgta gataga                                           26

<210> SEQ ID NO 53
<211> LENGTH: 20
<212> TYPE: DNA
<213> ORGANISM: Artificial Sequence
<220> FEATURE:
<223> OTHER INFORMATION: HMA4.1 G382R mutant-probe

<400> SEQUENCE: 53
ttctgtttaa aagagcagag                                                  20

<210> SEQ ID NO 54
<211> LENGTH: 21
<212> TYPE: DNA
<213> ORGANISM: Artificial Sequence
<220> FEATURE:
<223> OTHER INFORMATION: HMA 4.1 wild type probe

<400> SEQUENCE: 54
tctgtttaaa ggagcagagt a                                                21

<210> SEQ ID NO 55
<211> LENGTH: 20
<212> TYPE: DNA
<213> ORGANISM: Artificial Sequence
<220> FEATURE:
<223> OTHER INFORMATION: HMA 4.1 forward primer

<400> SEQUENCE: 55
ccatgtgttg cgcactttca                                                  20

<210> SEQ ID NO 56
<211> LENGTH: 25
<212> TYPE: DNA
<213> ORGANISM: Artificial Sequence
<220> FEATURE:
<223> OTHER INFORMATION: HMA 4.1 reverse primer

<400> SEQUENCE: 56
aactcggtca cataaattc tcctt                                             25

<210> SEQ ID NO 57
```

<211> LENGTH: 19
<212> TYPE: DNA
<213> ORGANISM: Artificial Sequence
<220> FEATURE:
<223> OTHER INFORMATION: HMA4.2 W265* mutant-probe

<400> SEQUENCE: 57
atagattcaa cggtctagg                                                19

<210> SEQ ID NO 58
<211> LENGTH: 15
<212> TYPE: DNA
<213> ORGANISM: Artificial Sequence
<220> FEATURE:
<223> OTHER INFORMATION: HMA 4.2 wild type probe

<400> SEQUENCE: 58
ttcaacggtc tgggc                                                    15

<210> SEQ ID NO 59
<211> LENGTH: 31
<212> TYPE: DNA
<213> ORGANISM: Artificial Sequence
<220> FEATURE:
<223> OTHER INFORMATION: HMA 4.2 forward primer

<400> SEQUENCE: 59
ggtgaaacta tacctattga tggagttgta a                                  31

<210> SEQ ID NO 60
<211> LENGTH: 32
<212> TYPE: DNA
<213> ORGANISM: Artificial Sequence
<220> FEATURE:
<223> OTHER INFORMATION: HMA 4.2 reverse primer

<400> SEQUENCE: 60
cactaaataa atgaagcatg aaggaatact ac                                 32

<210> SEQ ID NO 61
<211> LENGTH: 16
<212> TYPE: DNA
<213> ORGANISM: Artificial Sequence
<220> FEATURE:
<223> OTHER INFORMATION: HMA4.2 Q561* mutant-probe

<400> SEQUENCE: 61
caaccatgtg taggat                                                   16

<210> SEQ ID NO 62
<211> LENGTH: 16
<212> TYPE: DNA
<213> ORGANISM: Artificial Sequence
<220> FEATURE:
<223> OTHER INFORMATION: HMA 4.2 wild type probe

<400> SEQUENCE: 62
tgccaaccat gtgcag                                                   16

<210> SEQ ID NO 63
<211> LENGTH: 26
<212> TYPE: DNA
<213> ORGANISM: Artificial Sequence
<220> FEATURE:
<223> OTHER INFORMATION: HMA 4.2 forward primer

```
<400> SEQUENCE: 63
ttggtgtaaa agaagcaatg agagag                                          26

<210> SEQ ID NO 64
<211> LENGTH: 25
<212> TYPE: DNA
<213> ORGANISM: Artificial Sequence
<220> FEATURE:
<223> OTHER INFORMATION: HMA 4.2 reverse primer

<400> SEQUENCE: 64
atcatttcag cgtattgcag aattt                                           25
```

REDUCING CADMIUM ACCUMULATION IN FIELD GROWN TOBACCO PLANTS

This application is a U.S. National Stage Application of International Application No. PCT/EP2017/051761 filed Jan. 27, 2017, which was published in English on Aug. 3, 2017, as International Publication No. WO 2017/129739 A1. International Application No. PCT/EP2017/051761 claims priority to European Application No. 16153529.9 filed Jan. 29, 2016.

SEQUENCE LISTING

This application contains an amended Sequence Listing electronically submitted via EFS-Web on to the United States Patent and Trademark Office as an ASCII text file entitled "SequenceListingP10255WO" having a size of 48 kilobytes and created on Feb. 24, 2020. The information contained in the Sequence Listing is incorporated by reference herein.

BACKGROUND

Many heavy metals are naturally present in soil and are taken up by plants to a different degree. Some heavy metals, such as manganese or zinc, are essential for plants, since they represent co-factors required for enzyme activity. Other heavy metals are not essential for plants and in some cases a reduction in the heavy metal concentration would be beneficial. Cadmium (Cd) is one of the metals for which there is no reported beneficial effect on plant or human development. It is classified as known human carcinogen. If Cd is accumulated in excess in plants, it can trigger various deleterious effects—such as a reduced leaf surface, reduced dry weight, reduced water content, reduced chlorophyll content, and reduced carotenoid content. Tobacco is a plant species characterized by an ability to accumulate four times higher levels of Cd in the shoots than in the roots. It is desirable to be able to reduce the accumulation of Cd in plants—such as tobacco. It is especially desirable to be able to reduce the accumulation of Cd in plants—such as tobacco—when grown outside in an open field on a large scale for commercial production.

The degree of Cd accumulation in plants can be variable depending on several parameters attributed to the complexity of the genotype and the growth environment. For example, Cd concentrations in field-grown tobacco leaves can vary depending on factors such as the agro-climate, soil parameters, and cultivars. On average, the Cd concentrations measured in field-grown tobacco leaves (including midribs and veins) can be in the range from approximately 0.5 to 5 ppm (parts per million, or µg/g of dry weight of tobacco leaves). Lower and higher values have been observed in the range of 0 to 6.78 ppm (Lugon-Moulin et al., 2006). Various attempts have been made to reduce Cd accumulation in tobacco leaves. One method has involved reducing the accumulation of Cd in shoots by sequestering Cd in root vacuoles. This was accomplished by over-expressing the *A. thaliana* CAX2 and CAX4 calcium and manganese vacuolar transporters in tobacco roots (Korenkov et al., 2009).

It can be desirable to develop non-genetically modified organism (non-GMO) approaches to reduce Cd accumulation in plant leaves through the use of gene inactivation. Due to the difficulties of growing and commercialising genetically modified crops in countries, including Europe, it can be desirable to work with mutants featuring single nucleotide polymorphisms obtained by treatment with ethyl methanesulfonate (EMS) or the like rather than through the use of genetic engineering techniques. Mutants are not considered as GMOs even when the mutations are induced artificially. In the EU for example, there are no special regulations for plants derived from mutation breeding.

WO2012/041913 describes tobacco plants with reduced heavy metal content in leaves. This is achieved through the use of tobacco plants comprising at least one mutation in a HMA gene. The mutation causes a substitution or a deletion or an insertion of at least one amino acid in the polypeptide encoded by the nucleotide sequence and reduces the heavy metal uptake by the leaves of the plant. Various single mutations were identified in WO2012/041913 as summarised in Table 1, herein. This citation presents data of small plantlets grown in hydroponics. In this system, very high Cd and Zn concentrations were present that do not reflect the conditions in open field systems. Cd concentrations measured in leaves of control plants in such systems are 30- to 300-fold higher compared to that found under soil conditions. Hermand et al. (2014) report the effects of inactivating the tobacco orthologs of *Arabidopsis thaliana* HMA2 and HMA4 using mutations obtained by EMS treatment. AtHMA2 and AtHMA4 encode Heavy Metal ATPases (HMAs) that transport both zinc (Zn) and Cd from roots to shoots. Two orthologues to the AtHMA2 and AtHMA4 genes were identified in the *N. tabacum* genome and named NtHMAα and NtHMAβ, respectively. Expression was altered to determine the possibility of using this approach to obtain tobacco lines with reduced Cd levels in the leaves. To study the role of these NtHMA genes in tobacco, tobacco lines containing a mutation in either one of the NtHMA genes were identified by screening an EMS mutagenized mutant collection. Missense mutations (P249S, E387K and G515R) and nonsense mutations (W265* and R529*) were identified in either NtHMAα (P294S, E387K and W265*) or in NtHMA/3 (G515R, R520*). These mutations altered amino acids or introduced premature stop codons in the second (P294S and W265*) and third (E387K, G515R and R520*) cytosolic loop of the HMA protein. The homozygous single mutant lines generated by Hermand et al. (2014) were grown under artificial sterile conditions on agar plates containing Murashige and Skoog medium. The results obtained with the single mutants as reported in FIGS. 4*a* and 4*b* of Hermand et al. (2014) are summarised in Table 2 herein. The single mutants were reported to show reduced Cd and Zn accumulation in shoots. The single mutant plants were reported to have growth and development that was comparable to the wild type. Plants containing a nonsense mutation in both NtHMA genes showed strong stunted growth and did not produce seeds. Notably, the data reported in FIGS. 4*a* and 4*b* is obtained using small plantlets grown in sterile culture in which artificially high Cd and Zn concentrations are used. These artificially high Cd and Zn concentrations do not reflect the natural conditions that are present in open field conditions. The Cd concentrations measured in the shoots of control plants in FIG. 4*a* is about 135 ppm. These concentrations are about 30- to 300-fold higher as compared to the Cd concentrations seen in plants grown under field conditions. Based on the results of their work, using the mutants containing single nucleotide polymorphisms obtained by EMS treatment, Hermand et al. (2014) concluded that the function of NtHMAα/β needs to be at least partially preserved for normal growth and development and that engineering commercially valuable tobacco plants with no Cd in the shoots cannot be achieved through the sole inactivation of the two NtHMA genes. It is discussed that inactivating only one of the NtHMA genes could lead to commercially valuable plants that display a reduction of Cd concentration in shoots. To further decrease the ability of the plant to accumulate Cd in the leaves, Hermand et al. (2014) contemplate combining different mutations in NtHMA genes together—such as the combination of a nonsense mutation in one NtHMA gene with a leaky mutation in the other NtHMA gene. Liedschulte et al. at the 12th Solanaceae Conference (SOL2015), Bordeaux, France, 25 to 29 Oct., 2015 described that missense or nonsense mutations in either HMA4.1 or HMA4.2 (which correspond to NtHMAα and NtHMAβ, respectively) do not significantly reduce cadmium content in the leaves of tobacco plants grown under field conditions. In this study, HMA4 RNAi tobacco plants are described that exhibit around 10-times reduced Cd content compared to a wild type control. However, the phenotype was strongly affected with reduced growth, thicker leaves and necrotic lesions. A similar phenotype was reported for tobacco HMA4 double knockout mutants by Hermand et al., 2014. 19 homozygous missense HMA4 mutant lines and four homozygous nonsense HMA4 mutant lines were tested adjacent to their null-segregant controls in the field. No phenotypic differences were observed in HMA4 mutant plants. No statistically significant (paired T-test on ratios; p<0.05) Cd and Zn reduction beyond the level of measurement uncertainty (20%) were observed in any of the tested mutant lines containing either a homozygous missense or a nonsense mutation in one of the HMA4 genes. Liedschulte et al. (2015) conclude in their study that the complete knockout of HMA4 results in strong Cd and Zn reduction and phenotypic alterations, including dwarfism and necrotic lesions. It is also concluded that in contrast to Hermand et al. (2014), a deleterious mutation in NtHMA4.1 or NtHMA4.2 does not significantly reduce Cd levels in plants grown under field conditions. The approach of Hermand et al. (2014) is concluded not to be applicable to field conditions. There is a continuing need in the art to develop approaches—such as non-GMO approaches—to reduce Cd accumulation in plants—such as tobacco—when grown outside in an open field on a large scale for commercial production. The present invention seeks to address this need.

SUMMARY OF THE INVENTION

WO2012/041913 and Hermand et al. (2014) describe EMS mutant tobacco lines which show reduced Zn and Cd accumulation in shoots under highly artificial sterile or hydroponic growth conditions. In contrast to the teachings of WO2012/041913 and Hermand et al. (2014), the present invention is concerned with reducing the level of Cd in plants when they are grown outside in the open environment (for example, in the field) where the levels of Cd are 30- to 300-fold lower than the Cd levels used in WO2012/041913 and Hermand et al. (2014). It is intended that the plants described in the present disclosure are used for commercial production which demands that they are grown under field conditions in the open air in very large quantities rather than being grown under artificial conditions. To commercially grow plants under artificial conditions would be uneconomical. The present invention seeks to provide mutants plants—such as non-GMO mutant plants—in which the level of Cd accumulation is reduced when they are grown in open field conditions.

The conditions used by Hermand et al. (2014) do not reflect the natural conditions in open field conditions, which are the conditions that are of interest in the present disclosure. The results reported by Hermand et al. (2014) are of limited use to the skilled person seeking to reduce the level of Cd in plants grown in open field conditions since the Cd level in open field conditions and the artificial conditions used by Hermand et al. (2014) and are not comparable. Furthermore, Liedschulte et al. (2015) conclude that a deleterious mutation in NtHMA4.1 or NtHMA4.2 does not significantly reduce Cd levels in plants grown under field conditions beyond the level of measurement of uncertainty (about 20%). The approach of Hermand et al. (2014) is concluded as not being applicable to field conditions.

The present inventors created various HMA4 homozygous EMS single mutants, including the single W265* nonsense mutation reported by Hermand et al. (2014), and tested them in open field conditions. The results of this experiment are reported in Table 3 herein. The results show that none of the single mutants tested, including the W265* single mutation of Hermand et al. (2014), showed any Cd reduction under open field conditions. As can be seen in Table 3, fourth column, the % Cd reduction vs control for each of the single mutants tested under open field conditions was 0%. These results are consistent with the results reported by Liedschulte et al. (2015).

Based on the knowledge that none of the single mutants tested and reported in Table 3, herein, showed any Cd reduction under open field conditions, the present inventors expectations were that combining two or more of these single mutations that are inactive under open field conditions together would have no or negligible impact on Cd reduction under open field conditions. However, and in direct contrast to this expectation, the present inventors determined that when various single mutations as reported in Table 3 are combined together in different combinations to form double homozygous mutants that high levels of Cd reduction in leaf (for example, 20% or greater) can be achieved in open field conditions. In some instances, the level of Cd reduction in leaf that was achieved in open field conditions was at least about 27%, about 30%, about 40%, about 50%, about 60%, about 70%, about 80% or even about 90% or more, as summarised in Tables 4, 5 and 6 herein. This high level of Cd reduction is highly advantageous in reducing the level of Cd in plants grown under open field conditions. Surprisingly, the double mutant plants with reduced levels of Cd in leaf as described herein do not suffer a deleterious phenotype—such as reduced amounts of growth/dwarfism/biomass. The advantageous results reported for the double mutants described herein is a finding that was not expected nor predicted by the present inventors. Based on this data, the present invention is based, at least in part, on the finding that plants can exhibit reduced accumulation of Cd in leaf when grown in open field conditions by at least partially reducing the expression or activity of NtHMA4.1 and NtHMA4.2. Suitably, non-GMO plants can be prepared through the use of mutagenesis and suitably do not suffer a deleterious phenotype. NtHMA4.1 and NtHMA4.2 correspond to NtHMAα and NtHMAβ, respectively, as reported by Hermand et al. (2014). Advantageously, the different mutant combinations can be used as a toolkit to breed different varieties with reduced levels of cadmium and without compromised phenotype and/or yield.

ASPECTS AND EMBODIMENTS OF THE INVENTION

In a first aspect, there is described a mutant plant or part thereof having at least partially reduced expression or activity of at least two heavy metal ATPases (HMAs), said two HMAs comprising, consisting or consisting essentially of: (i) polypeptides having at least 65% sequence identity to SEQ ID NO:1 and SEQ ID NO:2; (ii) polynucleotides encoding the polypeptides set forth in (i); or (iii) polynucleotides having at least 65% sequence identity to SEQ ID NO:3 and SEQ ID NO:4 encoding HMAs; wherein the mutant plant or part thereof exhibits at least a 27% reduction, as compared to the control plant, in the accumulation of cadmium in leaf when the mutant plant is field grown in the presence of naturally or non-naturally occurring cadmium.

Suitably, the expression or activity of one of the HMAs set forth in (i) or (ii) or (iii) is partially reduced or lost and the expression or activity of one of the HMAs set forth in (i) or (ii) or (iii) is lost as compared to a control plant.

Suitably, the phenotype of the mutant plant or part thereof at harvest time is the same as the control plant at the same harvest time, suitably, wherein the mutant plant or part thereof does not show a biomass (for example, leaf weight) reduction at harvest time as compared to the control plant at the same harvest time.

Suitably, the mutant plant or part thereof comprises at least one genetic alteration in a regulatory region or in the coding sequence of each of the polynucleotide sequences set forth in (ii) or (iii), suitably, where in the mutation is a missense mutation or a nonsense mutation. Suitably, the mutant plant or part thereof comprises one or more of the following mutations: at least one mutation at a position corresponding to an amino acid position in the A-domain loop of a HMA polypeptide encoded by a non-mutated sequence set forth SEQ ID NO: 3 and at least one mutation at a position corresponding to an amino acid position in an P/N-domain loop of a HMA polypeptide encoded by the non-mutated sequence set forth SEQ ID NO: 4; suitably, at least one mutation at a position corresponding to amino acid positions 251 to 296 of the A-domain loop of the HMA polypeptide encoded by the non-mutated sequence set forth in SEQ ID NO: 3 and at least one mutation at a position corresponding to amino acid position 561 of the P/N-domain loop of a HMA polypeptide encoded by the non-mutated sequence set forth in SEQ ID NO: 4, suitably, at least one mutation at a position corresponding to amino acid position 251 or 293 or 296 of the A-domain loop of the HMA polypeptide encoded by the non-mutated sequence set forth in SEQ ID NO: 3 and at least one mutation at a position corresponding to amino acid position 561 of the P/N-domain loop of the HMA polypeptide encoded by the non-mutated sequence set forth in SEQ ID NO: 4; at least one mutation at a position corresponding to an amino acid position in the A-domain loop of a HMA polypeptide encoded by a non-mutated sequence set forth in SEQ ID NO: 3 and at least one mutation at a position corresponding to an amino acid position in the A-domain loop of a HMA polypeptide encoded by a non-mutated sequence set forth in SEQ ID NO: 4; suitably, at least one mutation at a position corresponding to amino acid position 293 of the A-domain loop of the HMA polypeptide encoded by the non-mutated sequence set forth in SEQ ID NO: 3 and at least one mutation at a position corresponding to amino acid positions 223 to 265 of the A-domain loop of the HMA polypeptide encoded by the non-mutated sequence set forth in SEQ ID NO: 4, suitably, wherein the plant comprises at least one mutation at a position corresponding to amino acid position 293 of the A-domain loop of the HMA polypeptide encoded by the non-mutated sequence set forth in SEQ ID NO: 3 and at least one mutation at a position corresponding to amino acid position 223 or 234 or 235 or 265 of the A-domain loop of the HMA polypeptide encoded by the non-mutated sequence set forth in SEQ ID NO: 4; at least one mutation at a position corresponding to an amino acid position in a P/N-domain loop of a HMA polypeptide encoded by a non-mutated sequence set forth in SEQ ID NO: 3 and at least one mutation at a position corresponding to an amino acid position in a P/N-domain loop of a HMA polypeptide encoded by a non-mutated sequence set forth in SEQ ID NO: 4, suitably, at least one mutation at a position corresponding to amino acid positions 402 to 464 of the P/N-domain of the third loop of the HMA polypeptide encoded by the non-mutated sequence set forth in SEQ ID NO: 3 and at least one mutation at a position corresponding to amino acid position 561 of the P/N-domain loop of the HMA polypeptide encoded by the non-mutated sequence set forth in SEQ ID NO: 4. The mutant plant or part thereof, comprising at least one mutation at a position corresponding to amino acid position 402 or 464 of the P/N-domain of the third loop of the HMA polypeptide encoded by the non-mutated sequence set forth in SEQ ID NO: 3 and at least one mutation at a position corresponding to amino acid position 561 of the P/N-domain loop of the HMA polypeptide encoded by the non-mutated sequence set forth in SEQ ID NO: 4; at least one mutation at a position corresponding to an amino acid position in a P/N-domain loop of a HMA polypeptide encoded by a non-mutated sequence set forth in SEQ ID NO: 3 and at least one mutation at a position corresponding to an amino acid position in a A-domain loop of a HMA polypeptide encoded by a non-mutated sequence set forth in SEQ ID NO: 4, suitably, at least one mutation at a position corresponding to amino acid position 438 of the P/N-domain loop of the HMA polypeptide encoded by the non-mutated sequence set forth in SEQ ID NO: 3 and at least one mutation at amino acid position 265 in the A-domain loop of the HMA polypeptide encoded by the non-mutated sequence set forth in SEQ ID NO: 4; at least one mutation at a position corresponding to an amino acid position in the third cytoplasmic loop of the P/N domain of a HMA polypeptide encoded by a non-mutated sequence set forth SEQ ID NO: 3 and at least one mutation at a position corresponding to an amino acid position in a second cytoplasmic loop of the A domain loop of a HMA polypeptide encoded by the non-mutated sequence set forth SEQ ID NO: 4; suitably, at least one mutation at a position corresponding to amino acid positions 464 of the third cytoplasmic loop of the P/N domain of a HMA polypeptide encoded by the non-mutated sequence set forth in SEQ ID NO: 3 and at least one mutation at a position corresponding to amino acid position 265, 223, 234 or 235 of the second cytoplasmic loop of the A domain loop of a HMA polypeptide encoded by the non-mutated sequence set forth in SEQ ID NO: 4; at least one mutation at a position corresponding to an amino acid position in the second cytoplasmic loop of the A domain of a HMA polypeptide encoded by a non-mutated sequence set forth SEQ ID NO: 3 and at least one mutation at a position corresponding to an amino acid position in a second cytoplasmic loop of the A domain loop of a HMA polypeptide encoded by the non-mutated sequence set forth SEQ ID NO: 4; suitably, at least one mutation at a position corresponding to amino acid position 296 of the second cytoplasmic loop of the A domain of the non-mutated sequence set forth in SEQ ID NO: 3 and at least one mutation at a position corresponding to amino acid position 265, 223, 234 or 235 of the second cytoplasmic loop of the A domain loop of a HMA polypeptide encoded by the non-mutated sequence set forth in SEQ ID NO: 4; at least one mutation at a position corresponding to an amino acid position in the third cytoplasmic loop of the P/N domain of a non-mutated sequence set forth SEQ ID NO: 3 and at least one mutation at a position corresponding to an amino acid position in a second cytoplasmic loop of the A domain loop of a HMA polypeptide encoded by the non-mutated sequence set forth SEQ ID NO: 4; suitably, at least one mutation at a position corresponding to amino acid position 402 of the third cytoplasmic loop of the P/N domain of the non-mutated sequence set forth in SEQ ID NO: 3 and at least one mutation at a position corresponding to amino acid position 265, 223, 234 or 235 of the second cytoplasmic loop of the A domain loop of a HMA polypeptide encoded by the non-mutated sequence set forth in SEQ ID NO: 4; at least one mutation at a position corresponding to an amino acid position in the second cytoplasmic loop of the A domain loop of a non-mutated sequence set forth SEQ ID NO: 3 and at least one mutation at a position corresponding to an amino acid position in a second cytoplasmic loop of the A domain loop of a HMA polypeptide encoded by the non-mutated sequence set forth SEQ ID NO: 4; suitably, at least one mutation at a position corresponding to amino acid position 251 of the second cytoplasmic loop of the A domain loop of the non-mutated sequence set forth in SEQ ID NO: 3 and at least one mutation at a position corresponding to amino acid position 265, 223, 234 or 235 of the second cytoplasmic loop of the A domain loop of a HMA polypeptide encoded by the non-mutated sequence set forth in SEQ ID NO: 4; at least one mutation at a position corresponding to an amino acid position in the second cytoplasmic loop of the third cytoplasmic loop of the P/N domain of a non-mutated sequence set forth SEQ ID NO: 3 and at least one mutation at a position corresponding to an amino acid position in a third cytoplasmic loop of the P/N domain second cytoplasmic loop of the A domain loop of a HMA polypeptide encoded by the non-mutated sequence set forth SEQ ID NO: 4; suitably, at least one mutation at a position corresponding to amino acid position 438 of the third cytoplasmic loop of the P/N domain of the non-mutated sequence set forth in SEQ ID NO: 3 and at least one mutation at a position corresponding to amino acid position 265, 223, 234 or 235 of the second cytoplasmic loop of the A domain loop of a HMA polypeptide encoded by the non-mutated sequence set forth in SEQ ID NO: 4; at least one mutation at a position corresponding to an amino acid position in the A-domain loop of a HMA polypeptide encoded by a non-mutated sequence set forth SEQ ID NO: 4 and at least one mutation at a position corresponding to an amino acid position in an P/N-domain loop of a HMA polypeptide encoded by the non-mutated sequence set forth SEQ ID NO: 3; suitably, at least one mutation at a position corresponding to amino acid positions 251 to 296 of the A-domain loop of the HMA polypeptide encoded by the non-mutated sequence set forth in SEQ ID NO: 4 and at least one mutation at a position corresponding to amino acid position 561 of the P/N-domain loop of a HMA polypeptide encoded by the non-mutated sequence set forth in SEQ ID NO: 3, suitably, at least one mutation at a position corresponding to amino acid position 251 or 293 or 296 of the A-domain loop of the HMA polypeptide encoded by the non-mutated sequence set forth in SEQ ID NO: 4 and at least one mutation at a position corresponding to amino acid position 561 of the P/N-domain loop of the HMA polypeptide encoded by the non-mutated sequence set forth in SEQ ID NO: 3; at least one mutation at a position corresponding to an amino acid position in the A-domain loop of a HMA polypeptide encoded by a non-mutated sequence set forth in SEQ ID NO: 4 and at least one mutation at a position corresponding to an amino acid position in the A-domain loop of a HMA polypeptide encoded by a non-mutated sequence set forth in SEQ ID NO: 3; suitably, at least one mutation at a position corresponding to amino acid position 293 of the A-domain loop of the HMA polypeptide encoded by the non-mutated sequence set forth in SEQ ID NO: 4 and at least one mutation at a position corresponding to amino acid positions 223 to 265 of the A-domain loop of the HMA polypeptide encoded by the non-mutated sequence set forth in SEQ ID NO: 3, suitably, wherein the plant comprises at least one mutation at a position corresponding to amino acid position 293 of the A-domain loop of the HMA polypeptide encoded by the non-mutated sequence set forth in SEQ ID NO: 4 and at least one mutation at a position corresponding to amino acid position 223 or 234 or 235 or 265 of the A-domain loop of the HMA polypeptide encoded by the non-mutated sequence set forth in SEQ ID NO: 3; at least one mutation at a position corresponding to an amino acid position in a P/N-domain loop of a HMA polypeptide encoded by a non-mutated sequence set forth in SEQ ID NO: 4 and at least one mutation at a position corresponding to an amino acid position in a P/N-domain loop of a HMA polypeptide encoded by a non-mutated sequence set forth in SEQ ID NO: 3, suitably, at least one mutation at a position corresponding to amino acid positions 402 to 464 of the P/N-domain of the third loop of the HMA polypeptide encoded by the non-mutated sequence set forth in SEQ ID NO: 4 and at least one mutation at a position corresponding to amino acid position 561 of the P/N-domain loop of the HMA polypeptide encoded by the non-mutated sequence set forth in SEQ ID NO: 3; suitably, at least one mutation at a position corresponding to amino acid position 402 or 464 of the P/N-domain of the third loop of the HMA polypeptide encoded by the non-mutated sequence set forth in SEQ ID NO: 4 and at least one mutation at a position corresponding to amino acid position 561 of the P/N-domain loop of the HMA polypeptide encoded by the non-mutated sequence set forth in SEQ ID NO: 3; at least one mutation at a position corresponding to an amino acid position in a P/N-domain loop of a HMA polypeptide encoded by a non-mutated sequence set forth in SEQ ID NO: 4 and at least one mutation at a position corresponding to an amino acid position in a A-domain loop of a HMA polypeptide encoded by a non-mutated sequence set forth in SEQ ID NO: 3, suitably, at least one mutation at a position corresponding to amino acid position 438 of the P/N-domain loop of the HMA polypeptide encoded by the non-mutated sequence set forth in SEQ ID NO: 4 and at least one mutation corresponding to amino acid position 265 in the A-domain loop of the HMA polypeptide encoded by the non-mutated sequence set forth in SEQ ID NO: 3; at least one mutation at a position corresponding to an amino acid position in the third cytoplasmic loop of the P/N domain of a HMA polypeptide encoded by a non-mutated sequence set forth SEQ ID NO: 4 and at least one mutation at a position corresponding to an amino acid position in a second cytoplasmic loop of the A domain loop of a HMA polypeptide encoded by the non-mutated sequence set forth SEQ ID NO: 3; suitably, at least one mutation at a position corresponding to amino acid positions 464 of the third cytoplasmic loop of the P/N domain of a HMA polypeptide encoded by the non-mutated sequence set forth in SEQ ID NO: 4 and at least one mutation at a position corresponding to amino acid position 265, 223, 234 or 235 of the second cytoplasmic loop of the A domain loop of a HMA polypeptide encoded by the non-mutated sequence set forth in SEQ ID NO: 3; at least one mutation at a position corresponding to an amino acid position in the second cytoplasmic loop of the A domain of a HMA polypeptide encoded by a non-mutated sequence set forth SEQ ID NO: 4 and at least one mutation at a position corresponding to an amino acid position in a second cytoplasmic loop of the A domain loop of a HMA polypeptide encoded by the non-mutated sequence set forth SEQ ID NO: 3 suitably, at least one mutation at a position corresponding to amino acid position 296 of the second cytoplasmic loop of the A domain of the non-mutated sequence set forth in SEQ ID NO: 4 and at least one mutation at a position corresponding to amino acid position 265, 223, 234 or 235 of the second cytoplasmic loop of the A domain loop of a HMA polypeptide encoded by the non-mutated sequence set forth in SEQ ID NO: 3; at least one mutation at a position corresponding to an amino acid position in the third cytoplasmic loop of the P/N domain of a non-mutated sequence set forth SEQ ID NO: 4 and at least one mutation at a position corresponding to an amino acid position in a second cytoplasmic loop of the A domain loop of a HMA polypeptide encoded by the non-mutated sequence set forth SEQ ID NO: 3; suitably, at least one mutation at a position corresponding to amino acid position 402 of the third cytoplasmic loop of the P/N domain of the non-mutated sequence set forth in SEQ ID NO: 4 and at least one mutation at a position corresponding to amino acid position 265, 223, 234 or 235 of the second cytoplasmic loop of the A domain loop of a HMA polypeptide encoded by the non-mutated sequence set forth in SEQ ID NO: 3; at least one mutation at a position corresponding to an amino acid position in the second cytoplasmic loop of the A domain loop of a non-mutated sequence set forth SEQ ID NO: 4 and at least one mutation at a position corresponding to an amino acid position in a second cytoplasmic loop of the A domain loop of a HMA polypeptide encoded by the non-mutated sequence set forth SEQ ID NO: 3; suitably, at least one mutation at a position corresponding to amino acid position 251 of the second cytoplasmic loop of the A domain loop of the non-mutated sequence set forth in SEQ ID NO: 4 and at least one mutation at a position corresponding to amino acid position 265, 223, 234 or 235 of the second cytoplasmic loop of the A domain loop of a HMA polypeptide encoded by the non-mutated sequence set forth in SEQ ID NO: 3; and at least one mutation at a position corresponding to an amino acid position in the second cytoplasmic loop of the third cytoplasmic loop of the P/N domain of a non-mutated sequence set forth SEQ ID NO: 4 and at least one mutation at a position corresponding to an amino acid position in a third cytoplasmic loop of the P/N domain second cytoplasmic loop of the A domain loop of a HMA polypeptide encoded by the non-mutated sequence set forth SEQ ID NO: 3; suitably, at least one mutation at a position corresponding to amino acid position 438 of the third cytoplasmic loop of the P/N domain of the non-mutated sequence set forth in SEQ ID NO: 4 and at least one mutation at a position corresponding to amino acid position 265, 223, 234 or 235 of the second cytoplasmic loop of the A domain loop of a HMA polypeptide encoded by the non-mutated sequence set forth in SEQ ID NO: 3.

Suitably, the mutant plant or part thereof comprises one or more of the following mutations: a nonsense mutation at a position corresponding to amino acid position 293 of SEQ ID NO:1 and a nonsense mutation at a position corresponding to amino acid position 561 of a non-mutated sequence set forth in SEQ ID NO:2, suitably, wherein the mutations are Q293* and Q561*, and wherein * denotes a stop codon; a nonsense mutation at a position corresponding to amino acid position 293 of SEQ ID NO:1 and a nonsense mutation at a position corresponding to amino acid position 265 of a non-mutated sequence set forth in SEQ ID NO:2, suitably, wherein the mutations are Q293* and W265*, wherein * denotes a stop codon; a missense mutation at a position corresponding to amino acid position 296 of SEQ ID NO:1 and a nonsense mutation at a position corresponding to amino acid position 561 of a non-mutated sequence set forth in SEQ ID NO:2, suitably, wherein the mutations are E296K and Q561*, wherein * denotes a stop codon; a missense mutation at a position corresponding to amino acid position 402 of SEQ ID NO:1 and a nonsense mutation at a position corresponding to amino acid position 561 of a non-mutated sequence set forth in SEQ ID NO:2, suitably, wherein the mutations are T402I and Q561*, wherein * denotes a stop codon; a missense mutation at a position corresponding to amino acid position 251 of SEQ ID NO:1 and a nonsense mutation at a position corresponding to amino acid position 561 of a non-mutated sequence set forth in SEQ ID NO:2, suitably, wherein the mutations are G251D and Q561*, wherein * denotes a stop codon; a nonsense mutation at a position corresponding to amino acid position 464 of SEQ ID NO:1 and a nonsense mutation at a position corresponding to amino acid position 561 of a non-mutated sequence set forth in SEQ ID NO:2, suitably, wherein the mutations are G251D and Q561*, wherein * denotes a stop codon; a nonsense mutation at a position corresponding to amino acid position 293 of SEQ ID NO:1 and a missense mutation at a position corresponding to amino acid position 223 of a non-mutated sequence set forth in SEQ ID NO:2, suitably, wherein the mutations are Q293* and L223F, wherein * denotes a stop codon; a nonsense mutation at a position corresponding to amino acid position 293 of SEQ ID NO:1 and a missense mutation at a position corresponding to amino acid position 234 of a non-mutated sequence set forth in SEQ ID NO:2, suitably, wherein the mutations are Q293* and D234N, wherein * denotes a stop codon; a nonsense mutation at a position corresponding to amino acid position 293 of SEQ ID NO:1 and a missense mutation at a position corresponding to amino acid position 235 of a non-mutated sequence set forth in SEQ ID NO:2, suitably, wherein the mutations are Q293* and G235E, wherein * denotes a stop codon; a missense mutation at a position corresponding to amino acid position 438 of SEQ ID NO:1 and a nonsense mutation at a position corresponding to amino acid position 265 of a non-mutated sequence set forth in SEQ ID NO:2, suitably, wherein the mutations are H438Y and W265*, wherein * denotes a stop codon; a nonsense mutation at a position corresponding to amino acid position 464 of SEQ ID NO:1 and a nonsense mutation at a position corresponding to amino acid position 265 of SEQ ID NO:2, suitably, wherein the mutations are Q464* and W265**, wherein * denotes a stop codon; a nonsense mutation at a position corresponding to amino acid position 464 of SEQ ID NO:1 and a missense mutation at a position corresponding to amino acid position 223 of SEQ ID NO:2, suitably, wherein the mutations are Q464* and L223F, wherein * denotes a stop codon; a nonsense mutation at a position corresponding to amino acid position 464 of SEQ ID NO:1 and a missense mutation at a position corresponding to amino acid position 234 of SEQ ID NO:2, suitably, wherein the mutations are Q464* and D234N, wherein * denotes a stop codon; a nonsense mutation at a position corresponding to amino acid position 464 of SEQ ID NO:1 and a missense mutation at a position corresponding to amino acid position 235 of SEQ ID NO:2, suitably, wherein the mutations are Q464* and G235E, wherein * denotes a stop codon; a missense mutation at a position corresponding to amino acid position 296 of SEQ ID NO:1 and a nonsense mutation at a position corresponding to amino acid position 265 of SEQ ID NO:2, suitably, wherein the mutations are E296K and W265*, wherein * denotes a stop codon; a missense mutation at a position corresponding to amino acid position 296 of SEQ ID NO:1 and a missense mutation at a position corresponding to amino acid position 223 of SEQ ID NO:2, suitably, wherein the mutations are E296K and L223F; a missense mutation at a position corresponding to amino acid position 296 of SEQ ID NO:1 and a missense mutation at a position corresponding to amino acid position 234 of SEQ ID NO:2, suitably, wherein the mutations are E296K and D234N, wherein * denotes a stop codon; or a missense mutation at a position corresponding to amino acid position 296 of SEQ ID NO:1 and a missense mutation at a position corresponding to amino acid position 235 of SEQ ID NO:2, suitably, wherein the mutations are E296K and G235E; a missense mutation at a position corresponding to amino acid position 402 of SEQ ID NO:1 and a nonsense mutation at a position corresponding to amino acid position 265 of SEQ ID NO:2, suitably, wherein the mutations are T402I and W265*, wherein * denotes a stop codon; a missense mutation at a position corresponding to amino acid position 402 of SEQ ID NO:1 and a missense mutation at a position corresponding to amino acid position 223 of SEQ ID NO:2, suitably, wherein the mutations are T402I and L223F; a missense mutation at a position corresponding to amino acid position 402 of SEQ ID NO:1 and a missense mutation at a position corresponding to amino acid position 234 of SEQ ID NO:2, suitably, wherein the mutations are T402I and D234N; a missense mutation at a position corresponding to amino acid position 402 of SEQ ID NO:1 and a missense mutation at a position corresponding to amino acid position 235 of SEQ ID NO:2, suitably, wherein the mutations are T402I and G235E; a missense mutation at a position corresponding to amino acid position 251 of SEQ ID NO:1 and a nonsense mutation at a position corresponding to amino acid position 265 of SEQ ID NO:2, suitably, wherein the mutations are G251D and W265*, wherein * denotes a stop codon; or a missense mutation at a position corresponding to amino acid position 251 of SEQ ID NO:1 and a missense mutation at a position corresponding to amino acid position 223 of SEQ ID NO:2, suitably, wherein the mutations are G251D and L223F; a missense mutation at a position corresponding to amino acid position 251 of SEQ ID NO:1 and a missense mutation at a position corresponding to amino acid position 234 of SEQ ID NO:2, suitably, wherein the mutations are G251D and D234N; a missense mutation at a position corresponding to amino acid position 251 of SEQ ID NO:1 and a missense mutation at a position corresponding to amino acid position 235 of SEQ ID NO:2, suitably, wherein the mutations are G251D and G235E; a missense mutation at a position corresponding to amino acid position 438 of SEQ ID NO:1 and a nonsense mutation at a position corresponding to amino acid position 561 of SEQ ID NO:2, suitably, wherein the mutations are H438Y and Q561*, wherein * denotes a stop codon; a missense mutation at a position corresponding to amino acid position 438 of SEQ ID NO:1 and a missense mutation at a position corresponding to amino acid position 223 of SEQ ID NO:2, suitably, wherein the mutations are H438Y and L223F, wherein * denotes a stop codon; a missense mutation at a position corresponding to amino acid position 438 of SEQ ID NO:1 and a missense mutation at a position corresponding to amino acid position 234 of SEQ ID NO:2, suitably, wherein the mutations are H438Y and D234N, wherein * denotes a stop codon; a missense mutation at a position corresponding to amino acid position 438 of SEQ ID NO:1 and a missense mutation at a position corresponding to amino acid position 235 of SEQ ID NO:2, suitably, wherein the mutations are H438Y and G235E, wherein * denotes a stop codon; a nonsense mutation at a position corresponding to amino acid position 293 of SEQ ID NO:2 and a nonsense mutation at a position corresponding to amino acid position 561 of a non-mutated sequence set forth in SEQ ID NO:1, suitably, wherein the mutations are Q293* and Q561*, and wherein * denotes a stop codon; a nonsense mutation at a position corresponding to amino acid position 293 of SEQ ID NO:2 and a nonsense mutation at a position corresponding to amino acid position 265 of a non-mutated sequence set forth in SEQ ID NO:1, suitably, wherein the mutations are Q293* and W265*, wherein * denotes a stop codon; a missense mutation at a position corresponding to amino acid position 296 of SEQ ID NO:2 and a nonsense mutation at a position corresponding to amino acid position 561 of a non-mutated sequence set forth in SEQ ID NO:1, suitably, wherein the mutations are E296K and Q561*, wherein * denotes a stop codon; a missense mutation at a position corresponding to amino acid position 402 of SEQ ID NO:2 and a nonsense mutation at a position corresponding to amino acid position 561 of a non-mutated sequence set forth in SEQ ID NO:1, suitably, wherein the mutations are T402I and Q561*, wherein * denotes a stop codon; a missense mutation at a position corresponding to amino acid position 251 of SEQ ID NO:2 and a nonsense mutation at a position corresponding to amino acid position 561 of a non-mutated sequence set forth in SEQ ID NO:1, suitably, wherein the mutations are G251D and Q561*, wherein * denotes a stop codon; a nonsense mutation at a position corresponding to amino acid position 464 of SEQ ID NO:2 and a nonsense mutation at a position corresponding to amino acid position 561 of a non-mutated sequence set forth in SEQ ID NO:1, suitably, wherein the mutations are G251D and Q561*, wherein * denotes a stop codon; a nonsense mutation at a position corresponding to amino acid position 293 of SEQ ID NO:2 and a missense mutation at a position corresponding to amino acid position 223 of a non-mutated sequence set forth in SEQ ID NO:1, suitably, wherein the mutations are Q293* and L223F, wherein * denotes a stop codon; a nonsense mutation at a position corresponding to amino acid position 293 of SEQ ID NO:2 and a missense mutation at a position corresponding to amino acid position 234 of a non-mutated sequence set forth in SEQ ID NO:1, suitably, wherein the mutations are Q293* and D234N, wherein * denotes a stop codon; a nonsense mutation at a position corresponding to amino acid position 293 of SEQ ID NO:2 and a missense mutation at a position corresponding to amino acid position 235 of a non-mutated sequence set forth in SEQ ID NO:1, suitably, wherein the mutations are Q293* and G235E, wherein * denotes a stop codon; a missense mutation at a position corresponding to amino acid position 438 of SEQ ID NO:2 and a nonsense mutation at a position corresponding to amino acid position 265 of a non-mutated sequence set forth in SEQ ID NO:1, suitably, wherein the mutations are H438Y and W265*, wherein * denotes a stop codon; a nonsense mutation at a position corresponding to amino acid position 464 of SEQ ID NO:2 and a nonsense mutation at a position corresponding to amino acid position 265 of SEQ ID NO:1, suitably, wherein the mutations are Q464* and W265**, wherein * denotes a stop codon; a nonsense mutation at a position corresponding to amino acid position 464 of SEQ ID NO:2 and a missense mutation at a position corresponding to amino acid position 223 of SEQ ID NO:1, suitably, wherein the mutations are Q464* and L223F, wherein * denotes a stop codon; a nonsense mutation at a position corresponding to amino acid position 464 of SEQ ID NO:2 and a missense mutation at a position corresponding to amino acid position 234 of SEQ ID NO:1, suitably, wherein the mutations are Q464* and D234N, wherein * denotes a stop codon; a nonsense mutation at a position corresponding to amino acid position 464 of SEQ ID NO:2 and a missense mutation at a position corresponding to amino acid position 235 of SEQ ID NO:1, suitably, wherein the mutations are Q464* and G235E, wherein * denotes a stop codon; a missense mutation at a position corresponding to amino acid position 296 of SEQ ID NO:2 and a nonsense mutation at a position corresponding to amino acid position 265 of SEQ ID NO:1, suitably, wherein the mutations are E296K and W265*, wherein * denotes a stop codon; a missense mutation at a position corresponding to amino acid position 296 of SEQ ID NO:2 and a missense mutation at a position corresponding to amino acid position 223 of SEQ ID NO:1, suitably, wherein the mutations are E296K and L223F; a missense mutation at a position corresponding to amino acid position 296 of SEQ ID NO:2 and a missense mutation at a position corresponding to amino acid position 234 of SEQ ID NO:1, suitably, wherein the mutations are E296K and D234N, wherein * denotes a stop codon; a missense mutation at a position corresponding to amino acid position 296 of SEQ ID NO:2 and a missense mutation at a position corresponding to amino acid position 235 of SEQ ID NO:1, suitably, wherein the mutations are E296K and G235E; a missense mutation at a position corresponding to amino acid position 402 of SEQ ID NO:2 and a nonsense mutation at a position corresponding to amino acid position 265 of SEQ ID NO:1, suitably, wherein the mutations are T402I and W265*, wherein * denotes a stop codon; a missense mutation at a position corresponding to amino acid position 402 of SEQ ID NO:2 and a missense mutation at a position corresponding to amino acid position 223 of SEQ ID NO:1, suitably, wherein the mutations are T402I and L223F; a missense mutation at a position corresponding to amino acid position 402 of SEQ ID NO:2 and a missense mutation at a position corresponding to amino acid position 234 of SEQ ID NO:1, suitably, wherein the mutations are T402I and D234N; a missense mutation at a position corresponding to amino acid position 402 of SEQ ID NO:2 and a missense mutation at a position corresponding to amino acid position 235 of SEQ ID NO:1, suitably, wherein the mutations are T402I and G235E; a missense mutation at a position corresponding to amino acid position 251 of SEQ ID NO:2 and a nonsense mutation at a position corresponding to amino acid position 265 of SEQ ID NO:1, suitably, wherein the mutations are G251D and W265*, wherein * denotes a stop codon; a missense mutation at a position corresponding to amino acid position 251 of SEQ ID NO:2 and a missense mutation at a position corresponding to amino acid position 223 of SEQ ID NO:1, suitably, wherein the mutations are G251D and L223F; a missense mutation at a position corresponding to amino acid position 251 of SEQ ID NO:2 and a missense mutation at a position corresponding to amino acid position 234 of SEQ ID NO:1, suitably, wherein the mutations are G251D and D234N; a missense mutation at a position corresponding to amino acid position 251 of SEQ ID NO:2 and a missense mutation at a position corresponding to amino acid position 235 of SEQ ID NO:1, suitably, wherein the mutations are G251D and G235E; a missense mutation at a position corresponding to amino acid position 438 of SEQ ID NO:2 and a nonsense mutation at a position corresponding to amino acid position 561 of SEQ ID NO:1, suitably, wherein the mutations are H438Y and Q561*, wherein * denotes a stop codon; a missense mutation at a position corresponding to amino acid position 438 of SEQ ID NO:2 and a missense mutation at a position corresponding to amino acid position 223 of SEQ ID NO:1, suitably, wherein the mutations are H438Y and L223F, wherein * denotes a stop codon; a missense mutation at a position corresponding to amino acid position 438 of SEQ ID NO:2 and a missense mutation at a position corresponding to amino acid position 234 of SEQ ID NO:1, suitably, wherein the mutations are H438Y and D234N, wherein * denotes a stop codon; and a missense mutation at a position corresponding to amino acid position 438 of SEQ ID NO:2 and a missense mutation at a position corresponding to amino acid position 235 of SEQ ID NO:1, suitably, wherein the mutations are H438Y and G235E, wherein * denotes a stop codon.

In a further aspect, there is disclosed a method for reducing the level of cadmium in the leaf of a field grown plant comprising the steps of: (a) reducing the expression or activity of two heavy metal ATPases (HMAs), said two HMAs comprising, consisting or consisting essentially of: (i) polypeptides having at least 65% sequence identity to SEQ ID NO:1 and SEQ ID NO:2; (ii) polynucleotides encoding the polypeptides set forth in (i); or (iii) polynucleotides having at least 65% sequence identity to SEQ ID NO:3 and SEQ ID NO:4 encoding HMAs, suitably, wherein the expression or activity of the (HMAs) is reduced by mutagenesis or genome editing; (b) growing the plant in the field; (c) optionally, measuring the cadmium content in the plant obtained in step (b); and (d) identifying a plant in which the cadmium content therein is reduced in comparison to a control plant in which the expression or activity of the HMAs has not been reduced, suitably, wherein the plant or part thereof exhibits at least a 27% reduction, as compared to the control plant, in the accumulation of cadmium in leaf when the plant is field grown in the presence of naturally or non-naturally occurring cadmium; suitably, wherein the phenotype of the mutant plant or part thereof at harvest time is the same as the control plant at the same harvest time, suitably, wherein the mutant plant or part thereof does not show a biomass (for example, leaf weight) reduction at harvest time as compared to the control plant at the same harvest time.

In a further aspect, there is disclosed a method for identifying one or more genetic alterations in a field grown plant that correlates with reduced levels of cadmium in leaf as compared to a field grown control plant that does not comprise the one or more genetic alterations, said method comprising the steps of: (a) identifying a plant with reduced levels of cadmium in the leaves when grown in the field as compared to a control plant grown in the field, optionally wherein the phenotype of the plant or part thereof at harvest time is the same as the control plant at the same harvest time, suitably, wherein the plant or part thereof does not show a biomass (for example, leaf weight) reduction at harvest time as compared to the control plant at the same harvest time; (b) providing a nucleic acid sample from the plant identified in step (a); and (c) identifying in the nucleic acid sample from step (b) one or more genetic alterations in the polynucleotide sequences encoding HMAs having at least 65% sequence identity to the non-mutated sequences set forth in SEQ ID NO:1 and SEQ ID NO:2 or the polynucleotide sequence having at least 65% sequence identity to SEQ ID NO:3 and SEQ ID NO:4.

In a further aspect, there is disclosed plant material from the mutant plant or part thereof as described herein, suitably wherein the plant material is cured or dried plant material, suitably, wherein the phenotype of the mutant plant or part thereof at harvest time is the same as the control plant at the same harvest time, suitably, wherein the mutant plant or part thereof does not show a biomass (for example, leaf weight) reduction at harvest time as compared to the control plant at the same harvest time.

In a further aspect, there is disclosed a method for producing plant material with reduced accumulation of cadmium in leaf when grown in the field as compared to a field grown control plant, said method comprising the steps of: (a) providing a mutant plant or part thereof as described herein; (b) growing the plant in the field; and (c) harvesting plant material from the plant, suitably, wherein the phenotype of the mutant plant or part thereof at harvest time is the same as the control plant at the same harvest time, suitably, wherein the mutant plant or part thereof does not show a biomass (for example, leaf weight) reduction at harvest time as compared to the control plant at the same harvest time.

In a further aspect, there is disclosed a mutant plant or part thereof or plant material derived or derivable therefrom that is obtained or obtainable by the method according to claim 7, suitably wherein the phenotype of the mutant plant or part thereof at harvest time is the same as the control plant at the same harvest time, suitably, wherein the mutant plant or part thereof does not show a biomass (for example, leaf weight) reduction at harvest time as compared to the control plant at the same harvest time.

In a further aspect, there is disclosed a plant product comprising at least a part of the mutant plant or part thereof or the plant material as described herein.

In a further aspect, there is disclosed a tobacco product or smoking article or consumable product comprising the mutant plant or part or the plant material or the plant product as described herein.

Suitably, at least one genetic alteration is introduced by (i) untargeted treatment of seed material with a mutagenising agent; or (ii) targeted by a genome editing system—such as an engineered CRISPR/Cas-based system, an engineered Transcription Activator-Like effector nuclease, an engineered zinc finger nuclease, or an engineered meganuclease.

In a further aspect, there is disclosed an isolated polypeptide encoding a metal ATPase (HMA) polypeptide comprising at least 60% sequence identity to the non-mutated sequence set forth in SEQ ID NO: 1 and comprising one or more of the mutations described herein.

In a further aspect, there is disclosed an isolated polypeptide encoding a metal ATPase (HMA) polypeptide comprising at least 60% sequence identity to the non-mutated sequence set forth in SEQ ID NO: 2 and comprising one or more of the mutations described herein, In a further aspect, there is disclosed a combination of isolated polypeptides comprising the isolated polypeptides described herein.

In a further aspect, there is disclosed an isolated polynucleotide sequence encoding the polypeptide(s) described herein.

In a further aspect, there is disclosed a construct, vector or expression vector comprising the isolated polynucleotide(s) described herein.

In a further aspect, there is disclosed a mutant plant cell from the mutant plant or part thereof or the plant material as described herein.

In a further aspect, there is disclosed cured or dried plant material comprising the mutant plant cell as described herein.

Suitably, the mutant plants described herein are produced by mutagenesis (for example, EMS mutagenesis) or genome editing (for example, using a CRISPR/Cas-based system, an engineered Transcription Activator-Like effector nuclease, an engineered zinc finger nuclease, or an engineered meganuclease).

SOME ADVANTAGES

Producing plants according to the present disclosure provides a number of advantages. The plants described herein can be non-GMO plants which overcomes the difficulties of growing and commercialising genetically modified crops.

The plants described herein can be grown in soils containing variable Cd concentrations. These plants and derivative seeds can provide more options for cultivating them in a broader range of soil environments, which may increase the amount of cultivatable soils available to practitioners. It may also increase the range of potentially acceptable phosphate fertilisers, which may contain higher levels of Cd as a contaminating element. Thus, lower cost phosphate fertilizers may become acceptable for crop production.

Smoking of products derived from these plants and the consumption of food crops to which the invention can be applied can be a healthier option due to the lower Cd levels. The % Cd reduction in the mutant plants—such as the aerial parts of the mutant plants, including the leaf lamina portion, can be approximately at least about 20%, 27%, 30%, 33%, 35%, 40%, 45%, 50%, 55%, 60%, 65%, 70%, 75%, 80%, 85%, 90%, 91%, 92%, 93%, 94% or 95% or more, when compared to the wild-type counterpart.

The phenotype of the mutant plants described herein can be similar to or the same as the wild-type counterparts, especially at harvest time, which means that the amount of biomass obtained for production is commercially acceptable. In particular, the mutant plants do not suffer from reduced amounts of growth/dwarfism, especially at harvest time.

Mutation combinations leading to lowest possible Cd content combined with commercially acceptable biomass levels can be chosen according to the plant species and tobacco cultivar of interest.

DEFINITIONS

Figure 1:
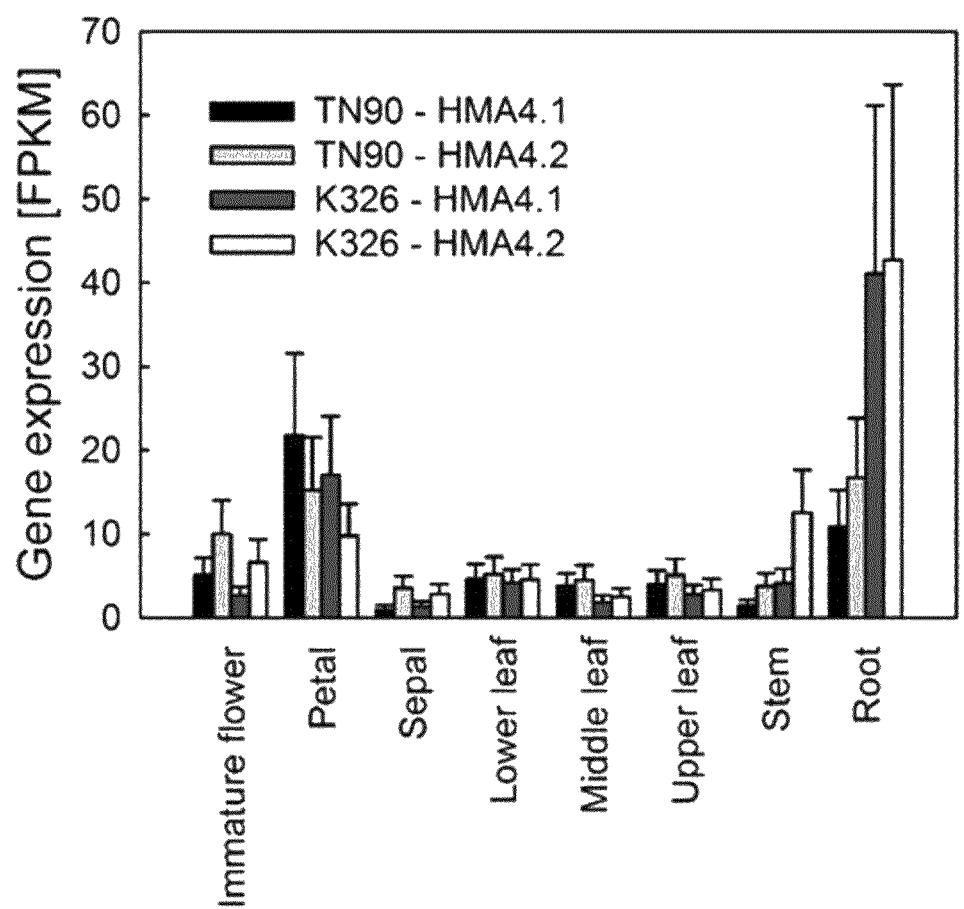
FIG. 1: Gene expression levels for HMA4.1 and HMA4.2 in TN90 and K326 in 8 tissues. The gene expression ratio between roots and leaves is similar for both HMA4.1 and HMA4.2. Plants used in this experiment are mature field grown plants. Bars and errors represent mean and upper confidence intervals of three replicate plants.

The technical terms and expressions used within the scope of this application are generally to be given the meaning commonly applied to them in the pertinent art of plant and molecular biology. All of the following term definitions apply to the complete content of this application. The word "comprising" does not exclude other elements or steps, and the indefinite article "a" or "an" does not exclude a plurality. A single step may fulfil the functions of several features recited in the claims. The terms "about", "essentially" and "approximately" in the context of a given numerate value or range refers to a value or range that is within 20%, within 10%, or within 5%, 4%, 3%, 2% or 1% of the given value or range.

The term "isolated" refers to any entity that is taken from its natural milieu, but the term does not connote any degree of purification.

An "expression vector" is a nucleic acid vehicle that comprises a combination of nucleic acid components for enabling the expression of nucleic acid. Suitable expression vectors include episomes capable of extra-chromosomal replication such as circular, double-stranded nucleic acid plasmids; linearized double-stranded nucleic acid plasmids; and other functionally equivalent expression vectors of any origin. An expression vector comprises at least a promoter positioned upstream and operably-linked to a nucleic acid, nucleic acid constructs or nucleic acid conjugate, as defined below.

The term "construct" refers to a double-stranded, recombinant nucleic acid fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

A "vector" refers to a nucleic acid vehicle that comprises a combination of nucleic acid components for enabling the transport of nucleic acid, nucleic acid constructs and nucleic acid conjugates and the like. Suitable vectors include episomes capable of extra-chromosomal replication such as circular, double-stranded nucleic acid plasmids; linearized double-stranded nucleic acid plasmids; and other vectors of any origin.

A "promoter" refers to a nucleic acid element/sequence, typically positioned upstream and operably-linked to a double-stranded DNA fragment. Promoters can be derived entirely from regions proximate to a native gene of interest, or can be composed of different elements derived from different native promoters or synthetic DNA segments.

The terms "homology, identity or similarity" refer to the degree of sequence similarity between two polypeptides or between two nucleic acid molecules compared by sequence alignment. The degree of homology between two discrete nucleic acid sequences being compared is a function of the number of identical, or matching, nucleotides at comparable positions. The percent identity may be determined by visual inspection and mathematical calculation. Alternatively, the percent identity of two nucleic acid sequences may be determined by comparing sequence information using a computer program such as—ClustalW, BLAST, FASTA or Smith-Waterman. The percentage identity for two sequences may take different values depending on: (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (for example, BLOSUM62, PAM250, Gonnet etc.), and gap-penalty, for example, functional form and constants. Having made the alignment, there are different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent.

Therefore, the shorter a pair of sequences is, the higher the sequence identity one may expect to occur by chance. The popular multiple alignment program ClustalW (*Nucleic Acids Research* (1994) 22, 4673-4680; *Nucleic Acids Research* (1997), 24, 4876-4882) is a suitable way for generating multiple alignments of polypeptides or polynucleotides. Suitable parameters for ClustalW maybe as follows: For polynucleotide alignments: Gap Open Penalty=15.0, Gap Extension Penalty=6.66, and Matrix=Identity. For polypeptide alignments: Gap Open Penalty=10. o, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment. Suitably, calculation of percentage identities is then calculated from such an alignment as (N/T), where N is the number of positions at which the sequences share an identical residue, and T is the total number of positions compared including gaps but excluding overhangs.

A "variant" means a substantially similar sequence. A variant can have a similar function or substantially similar function as a wild-type sequence. For the variants described herein, a similar function is at least about 50%, 60%, 70%, 80% or 90% of wild-type enzyme function. For the variants described herein, a substantially similar function is at least about 90%, 95%, 96%, 97%, 98% or 99% of wild-type enzyme function. The variants can have one or more favourable mutations that result in the enzyme having a reduced level of activity as compared to the wild-type polypeptide. The variants can have one or more favourable mutations that result in their activity being knocked out (ie. a 100% inhibition, and thus a non-functional polypeptide). Exemplary variants having one or more favourable mutations are described herein.

The term "plant" refers to any plant or part of a plant at any stage of its life cycle or development, and its progenies. In one embodiment, the plant is a "tobacco plant", which refers to a plant belonging to the genus *Nicotiana*. Preferred species of tobacco plant are described herein. Suitably, the plant is a mutant plant in which the expression of one or more genes or the activity of one or more proteins is modulated as compared to a control plant. Suitably, the alteration that renders the plant a mutant plant results in the modulation of the expression of one or more genes or the modulation of the activity of one or more polypeptides. In certain embodiments, the alteration is a genetic alternation or a genetic modification. "Plant parts" include plant cells, plant protoplasts, plant cell tissue cultures from which a whole plant can be regenerated, plant calli, plant clumps and plant cells that are intact in plants or parts of plants such as embryos, pollen, anthers, ovules, seeds, leaves, flowers, stems, branches, fruit, roots, root tips and the like. Progeny, variants and mutants of regenerated plants are also included within the scope of the disclosure, provided that they comprise the introduced polynucleotides described herein. Leaves of plants are particularly suitable for use in the present disclosure.

A "plant cell" refers to a structural and physiological unit of a plant. The plant cell may be in the form of a protoplast without a cell wall, an isolated single cell or a cultured cell, or as a part of higher organized unit such as but not limited to, plant tissue, a plant organ, or a whole plant. The term "plant material" refers to any solid, liquid or gaseous composition, or a combination thereof, obtainable from a plant, including biomass, leaves, stems, roots, flowers or flower parts, fruits, pollen, egg cells, zygotes, seeds, cuttings, secretions, extracts, cell or tissue cultures, or any other parts or products of a plant. In one embodiment, the plant material comprises or consists of biomass, stem, seed or leaves. In another embodiment, the plant material comprises or consists of leaves.

The term "variety" refers to a population of plants that share constant characteristics which separate them from other plants of the same species. While possessing one or more distinctive traits, a variety is further characterized by a very small overall variation between individuals within that variety. A variety is often sold commercially.

The term "line" or "breeding line" as used herein denotes a group of plants that are used during plant breeding. A line is distinguishable from a variety as it displays little variation between individuals for one or more traits of interest, although there may be some variation between individuals for other traits.

The term 'non-naturally occurring' as used herein describes an entity (for example, a polynucleotide, a genetic mutation, a polypeptide, a plant, and a plant cell and plant material) that is not formed by nature or that does not exist in nature. Such non-naturally occurring entities or artificial entities may be made, synthesized, initiated, modified, intervened, or manipulated by methods described herein or that are known in the art. Such non-naturally occurring entities or artificial entities may be made, synthesized, initiated, modified, intervened, or manipulated by man. Thus, by way of example, a non-naturally occurring plant, a non-naturally occurring plant cell or non-naturally occurring plant material may be made using genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell.

The term "modulating" may refer to reducing, inhibiting, eliminating increasing or otherwise affecting the expression or activity of a polypeptide. The term may also refer to reducing, inhibiting, eliminating, increasing or otherwise affecting the activity of a gene encoding a polypeptide which can include, but is not limited to, modulating transcriptional activity. The term "reduce" or "reduced" as used herein, refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression. The term "inhibit" or "inhibited" or "eliminate" or "eliminated" as used herein, refers to a reduction of from about 98% to about 100%, or a reduction of at least 98%, at least 99%, but particularly of 100%, of a quantity or an activity, such as but not limited to polypeptide activity, transcriptional activity and expression.

Transformation of a cell may be stable or transient. The term "transient transformation" or "transiently transformed" or variations thereof refers to the introduction of one or more exogenous polynucleotides into a cell in the absence of integration of the exogenous polynucleotide into the host cell's genome. In contrast, the term "stable transformation" or "stably transformed" refers to the introduction and integration of one or more exogenous polynucleotides into the genome of a cell. The term "stable transformant" refers to a cell which has stably integrated one or more exogenous polynucleotides into the genomic or organellar DNA. It is to be understood that an organism or its cell transformed with the nucleic acids, constructs and/or vectors of the present disclosure can be transiently as well as stably transformed. In certain embodiments, stable transformation is preferred.

The term "increase" or "increased" as used herein, refers to an increase of from about 5% to about 99%, or an increase of at least 5%, at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression.

The term "substantially" as used herein and when used in the context of an amount means that the amount is at least about 10%, at least about 9%, at least about 8%, at least about 7%, at least about 6%, at least about 5%, at least about 4%, at least about 3%, at least about 2%, at least about 1%, or at least about 0.1% of the amount that it is being compared to. The term "control" in the context of a control plant or control plant cell and the like means a plant or plant cell in which the expression or activity of the gene or protein of interest has not been modulated and so it can provide a comparison or reference with a plant or plant cell in which the expression or activity of the enzyme has been modified. Thus, in the context of the present invention, the control will not include the at least one genetic alteration which reduces the expression or activity of the HMA4(s) described herein. The control plant or pant cell may comprise an empty vector. The control plant or plant cell may correspond to a wild-type plant or wild-type plant cell and the like. In all such cases, the subject plant and the control plant are grown and harvested under the same conditions and using the same protocols for comparative purposes. Thus, by way of example, the subject plant and the control plant can be grown in and harvested from soil with about the same levels of heavy metal(s) content—such as Cd—so that comparisons between the two can be made. This can entail the subject plant and the control plant being grown in the same part of a field, for example, so that they are exposed to the approximately the same soil Cd levels. Changes in levels, ratios, activity, or distribution of the genes or polypeptides described herein, or changes in plant phenotype, particularly reduced accumulation of Cd and/or zinc can be measured using the methods described herein by comparing a subject plant to the control plant, suitably, where the subject plant and the control plant have been cultured and/or harvested using the same protocols. The control plant can provide a reference point for measuring changes in phenotype of the subject plant. The measurement of changes in phenotype can be measured at any time in a plant, including during plant development, senescence, or after curing. Measurement of changes in phenotype can be measured in plants grown under any conditions, including from plants grown in growth chamber, greenhouse, or in a field. Changes in phenotype can be measured by measuring Cd content and/or zinc content before and/or during and/or after curing or drying using methods that are well known in the art.

The term "field" as used herein, assumes its normal meaning in the art as an area of open land, especially one that can be or is planted with crops. The field is part of the natural environment, rather than an artificial environment—such as a laboratory or a greenhouse. Thus, unlike an artificial environment, which will commonly be a man made building or structure, the field is part of the open outside environment.

As discussed herein, the expression or activity of HMA(s) can be partially reduced in the mutant plant. As used, herein, them term "partially reduced" means that the expression or activity of HMA(s) in the mutant plant is between about 1% and 99% lower than the level of expression or activity of HMA(s) in the control plant. Suitably, the expression or activity of HMA(s) in the mutant plant is between at least about 10%, 20%, 30%, 40%, 50%, 60%, 70%, 80% or 90% lower than the level of expression or activity of HMA(s) in the control plant. By way of example, a nonsense mutation that truncates a large part of the HMA protein is expected not to show any enzyme activity thereby resulting in the complete loss of activity (that is, zero activity). By way of further example, for a missense mutation, enzyme activity can be the same as the control plant, partially reduced or may not be detectable (for example, completely lost or zero).

DETAILED DESCRIPTION

Isolated HMA4 polypeptide variants (mutants) are described herein comprising a polypeptide sequence having at least 65% sequence identity to SEQ ID NO:1 or SEQ ID NO:2 and at least one amino acid mutation as compared to the wild-type sequences set forth in SEQ ID NO:1 or SEQ ID NO:2. SEQ ID NO:1 and SEQ ID NO:2 are non-mutated sequences. SEQ ID NO: 1 and SEQ ID NO:2 correspond to the amino acid sequence of Nicotiana tabacum heavy metal ATPase (NtHMA4.1) GenBank Accession No: CCQ77798 and the amino acid sequence of Nicotiana tabacum heavy metal ATPase (NtHMA4.2) GenBank Accession No: CCW03243.1, respectively. Suitably, the isolated polypeptide comprises, consists or consists essentially of a sequence having at least 65%, 66%, 67%, 68%, 69%, 70%, 75%, 76%, 77%, 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity thereto and at least one amino acid mutation. Certain plants—such as N. tabacum—contain two homeologs of HMA4 which are referred to herein as HMA4.1 and HMA4.2.

In a plant, plant cell or plant material and the like, the function or activity of the mutant polypeptides is modulated, reduced, partially inactivated, inhibited, eliminated, knocked out or lost. In one embodiment, the function or activity of one mutant polypeptide can be inhibited, eliminated, knocked out or lost such that the polypeptide activity is not detectable. In one embodiment, the function or activity of two mutant polypeptides (for example, polypeptides encoded by homeologs of the same gene) can be inhibited, eliminated, knocked out or lost such that the polypeptide activity is not detectable.

In another embodiment, the function or activity of one mutant polypeptide (for example, one homeolog of a gene) is lost, inhibited or eliminated such that polypeptide activity is not detectable and the function or activity of another mutant polypeptide (for example, a second homeolog of the gene) is reduced or partially reduced such that the HMA polypeptide activity is lower as compared to a control HMA polypeptide but is still detectable. An exemplary mutation combination of this type is the double homozygous mutant G251D/Q561*, wherein the G251D mutation partially reduces the activity of NtHMA4.1 (SEQ ID NO:1) and the Q561* mutation knocks out, inhibits or eliminates the activity of NtHMA4.2 (SEQ ID NO:2). Either the activity of SEQ ID NO:1 or SEQ ID NO:2 is partially reduced and either the activity of SEQ ID NO:1 or SEQ ID NO:2 is lost, inhibited or eliminated provided that the activity of one of the HMA4 polypeptides is partially reduced and the activity of one of the HMAs is lost. Either the activity of SEQ ID NO:1 or SEQ ID NO:2 can be partially reduced and either the activity of SEQ ID NO:1 or SEQ ID NO:2 can be lost, inhibited or eliminated provided that the activity of one of the HMA4 polypeptides is partially reduced and the activity of one of the HMAs is lost. Suitably, at least one of the HMAs is fully knocked out and at least one of the HMAs comprises a nonsense or a missense mutation located either in the A-domain, in the DKTGT motif of the P-domain or in the HP locus of the N-domain.

In a plant, plant cell or plant material and the like, the activity of NtHMA4.1 (SEQ ID NO:1) and NtHMA4.2 (SEQ ID NO:2) can be lost, inhibited or eliminated as compared to a control plant. An exemplary mutation combination of this type is the double homozygous mutant Q293*/Q561*, wherein the Q293* mutation knocks out, inhibits or eliminates the activity of NtHMA4.1 (SEQ ID NO:1) and the Q561* mutation knocks out, inhibits or eliminates the activity of NtHMA4.2 (SEQ ID NO:2). Other exemplary mutants are described in Tables 4 and 5. Combinations or mixtures of the variant (mutant) HMA4.1 and HMA4.2 polypeptides and polynucleotides as described herein are contemplated.

For all combinations, the same combination in the other homeolog is contemplated, respectively. For example, the combination HMA4.1 E296K/HMA4.2 Q561* and the combination HMA4.1 Q561*/HMA4.2 E296K is contemplated.

Suitably, the HMA4 polypeptide variants cause the plant in which they are contained to exhibit at least about a 27%, 33%, 35%, 40%, 45%, 50%, 55%, 60%, 65%, 70%, 75%, 80%, 85%, 90%, 91%, 92%, 93%, 94% or 95% or more Cd reduction when compared to the control. Other HMAs with at least 60% identity to SEQ ID NO: 1 or SEQ ID NO:2 that comprise at least one amino acid mutation at the position(s) that upon sequence alignment correspond to the positions disclosed herein are also contemplated for use in the present disclosure. Examples of these sequences include HMA sequences from the Solanaceae family—such as tomato, potato and eggplant.

Fragments of the variant polypeptides are also contemplated with the proviso they that they carry one or more of the amino acid mutation(s). Fragments of variant polypeptides may range from at least about 25 amino acids, about 50 amino acids, about 75 amino acids, about 100 amino acids about 150 amino acids, about 200 amino acids, about 250 amino acids, about 300 amino acids, about 400 amino acids, about 500 amino acids, about 600 amino acids, or up to the full-length polypeptide.

The variants can be produced by introducing any type of alterations (for example, insertions, deletions, or substitutions of amino acids; changes in glycosylation states; changes that affect refolding or isomerizations, three-dimensional structures, or self-association states), provided that the mutant polypeptide causes the plant in which it is expressed to exhibit at least a reduction in the accumulation of Cd in as described herein.

Polypeptides variants include mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. Deliberate amino acid substitutions may be made on the basis of similarity in polarity, charge, solubility, hydrophobicity, hydrophilicity and the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. Conservative substitutions may be made, for example according to the Table below. Amino acids in the same block in the second column and suitably in the same line in the third column may be substituted for each other:

| ALIPHATIC | Non-polar | Gly Ala Pro |
| | | Ile Leu Val |
| | Polar - uncharged | Cys Ser Thr |
| | | Met Asn Gly |
| | Polar - charged | Asp Glu |
| | | Lys Arg |
| AROMATIC | | His Phe TrpTyr |

One suitable type of mutation is a missense mutation which is a point mutation in which a single nucleotide change results in a codon that codes for a different amino acid. Missense mutations can be particularly effective for partially inactivating (eg. reducing) a HMA4 polypeptide—such as HMA4.1 or HMA4.2.

Another suitable type of mutation is a nonsense mutation which is a point mutation in which a single nucleotide change results in a premature stop codon or a nonsense codon in the transcribed mRNA and a truncated, incomplete and non-functional HMA4 polypeptide—such as HMA4.1 or HMA4.2. Nonsense mutations can be particularly effective for inhibiting or eliminating or knocking out the activity of a HMA4 polypeptide—such as HMA4.1 or HMA4.2. As described herein, the expression or activity of one of HMA4.1 or HMA4.2 is at least partially reduced and the expression or activity of the other HMA4.1 or HMA4.2 is lost, eliminated or reduced as compared to a control plant in certain embodiments. In one embodiment, the expression or activity of one of HMA4.1 or HMA4.2 is partially reduced through the use of a missense point mutation and the expression or activity of the other HMA4.1 or HMA4.2 is lost, eliminated or reduced through the use of a nonsense point mutation.

Suitably, the mutations described herein are heterozygous or homozygous mutations. Suitably, the mutations described herein are homozygous mutations.

The mutation(s) can be positioned in, for example, a regulatory region of HMA4.1 or HMA4.2 or in the coding sequence of HMA4.1 or HMA4.2. In certain embodiments, the mutation(s) are positioned in the coding sequence of HMA4.1 or HMA4.2.

The HMA4 polypeptide comprises various domains which are described in Table 7.

For the combinations of mutants described herein, the same combination can be included in the other homeolog, respectively.

The expression or activity of at least two heavy metal ATPases (HMAs) is partially reduced such that a mutant plant or part thereof containing the HMAs exhibits at least a 27% reduction, as compared to the control plant, in the accumulation of cadmium in leaf when the mutant plant is field grown in the presence of naturally or non-naturally occurring cadmium. The expression or activity of one of the HMAs can be partially reduced or lost and the expression or activity of the other HMA can be lost as compared to a control plant.

Suitably, the HMA4 polypeptide variant can comprise at least one mutation at a position corresponding to an amino acid position in the A-domain of the HMA polypeptide encoded by SEQ ID NO: 3 and at least one mutation at a position corresponding to an amino acid position in the P/N-domain loop of the HMA polypeptide encoded by SEQ ID NO: 4.

Suitably, the HMA4 polypeptide variant can comprise at least one mutation at a position corresponding to an amino acid position in the A-domain of the HMA polypeptide encoded by SEQ ID NO: 4 and at least one mutation at a position corresponding to an amino acid position in the P/N-domain loop of the HMA polypeptide encoded by SEQ ID NO: 3.

More suitably, variant comprises at least one mutation at a position corresponding to amino acid positions 251 to 296 of the A-domain of the HMA polypeptide encoded by SEQ ID NO: 3 and at least one mutation at a position corresponding to amino acid position 561 of the P/N-domain loop of the HMA polypeptide encoded by SEQ ID NO: 4.

More suitably, variant comprises at least one mutation at a position corresponding to amino acid positions 251 to 296 of the A-domain of the HMA polypeptide encoded by SEQ ID NO: 4 and at least one mutation at a position corresponding to amino acid position 561 of the P/N-domain loop of the HMA polypeptide encoded by SEQ ID NO: 3.

More suitably, the variant comprises at least one mutation at a position corresponding to amino acid position 251 or 293 or 296 of the A-domain of the HMA polypeptide encoded by SEQ ID NO: 3 and at least one mutation at a position corresponding to amino acid position 561 of the P/N-domain loop of the HMA polypeptide encoded by SEQ ID NO: 4.

More suitably, the variant comprises at least one mutation at a position corresponding to amino acid position 251 or 293 or 296 of the A-domain of the HMA polypeptide encoded by SEQ ID NO: 4 and at least one mutation at a position corresponding to amino acid position 561 of the P/N-domain loop of the HMA polypeptide encoded by SEQ ID NO: 3.

Suitably, the plant comprises at least one mutation at a position corresponding to an amino acid position in the A-domain of the HMA polypeptide encoded by SEQ ID NO: 3 and at least one mutation at a position corresponding to an amino acid position in the A-domain of the HMA polypeptide encoded by SEQ ID NO: 4.

Suitably, the plant comprises at least one mutation at a position corresponding to an amino acid position in the A-domain of the HMA polypeptide encoded by SEQ ID NO: 4 and at least one mutation at a position corresponding to an amino acid position in the A-domain of the HMA polypeptide encoded by SEQ ID NO: 3.

More suitably, the variant comprises at least one mutation at a position corresponding to amino acid position 293 of the A-domain of the HMA polypeptide encoded by SEQ ID NO: 3 and at least one mutation at a position corresponding to amino acid positions 223 to 265 of the A-domain of the HMA polypeptide encoded by SEQ ID NO: 4.

More suitably, the variant comprises at least one mutation at a position corresponding to amino acid position 293 of the A-domain of the HMA polypeptide encoded by SEQ ID NO: 4 and at least one mutation at a position corresponding to amino acid positions 223 to 265 of the A-domain of the HMA polypeptide encoded by SEQ ID NO: 3.

More suitably, the variant comprises at least one mutation at a position corresponding to amino acid position 293 of the A-domain of the HMA polypeptide encoded by SEQ ID NO: 3 and at least one mutation at a position corresponding to amino acid position 223 or 234 or 235 or 265 of the N-domain of the A-domain of the HMA polypeptide encoded by SEQ ID NO: 4.

More suitably, the variant comprises at least one mutation at a position corresponding to amino acid position 293 of the A-domain of the HMA polypeptide encoded by SEQ ID NO: 4 and at least one mutation at a position corresponding to amino acid position 223 or 234 or 235 or 265 of the N-domain of the A-domain of the HMA polypeptide encoded by SEQ ID NO: 3.

Suitably, the variant comprises at least one mutation at a position corresponding to an amino acid position in the P/N-domain loop of the HMA polypeptide encoded by SEQ ID NO: 3 and at least one mutation at a position corresponding to an amino acid position in the P/N-domain of the HMA polypeptide encoded by SEQ ID NO: 4.

Suitably, the variant comprises at least one mutation at a position corresponding to an amino acid position in the P/N-domain loop of the HMA polypeptide encoded by SEQ ID NO: 4 and at least one mutation at a position corresponding to an amino acid position in the P/N-domain of the HMA polypeptide encoded by SEQ ID NO: 3.

More suitably, the variant comprises at least one mutation at a position corresponding to amino acid position 402 to 464 of the P/N-domain loop of the HMA polypeptide encoded by SEQ ID NO: 3 and at least one mutation at a position corresponding to amino acid position 561 of the P/N-domain of the HMA polypeptide encoded by SEQ ID NO: 4.

More suitably, the variant comprises at least one mutation at a position corresponding to amino acid position 402 to 464 of the P/N-domain loop of the HMA polypeptide encoded by SEQ ID NO: 4 and at least one mutation at a position corresponding to amino acid position 561 of the P/N-domain of the HMA polypeptide encoded by SEQ ID NO: 3.

More suitably, the variant comprises at least one mutation at a position corresponding to amino acid position 402 or 464 of the P-domain of the third loop of the HMA polypeptide encoded by SEQ ID NO: 3 and at least one mutation at a position corresponding to amino acid position 561 of the P/N-domain of the HMA polypeptide encoded by SEQ ID NO: 4.

More suitably, the variant comprises at least one mutation at a position corresponding to amino acid position 402 or 464 of the P-domain of the third loop of the HMA polypeptide encoded by SEQ ID NO: 4 and at least one mutation at a position corresponding to amino acid position 561 of the P/N-domain of the HMA polypeptide encoded by SEQ ID NO: 3.

Suitably, the variant comprises at least one mutation at a position corresponding to an amino acid position in the P/N-domain loop of the HMA polypeptide encoded by SEQ ID NO: 3 and at least one mutation at a position corresponding to an amino acid position in the A-domain of the HMA polypeptide encoded by SEQ ID NO: 4.

Suitably, the variant comprises at least one mutation at a position corresponding to an amino acid position in the P/N-domain loop of the HMA polypeptide encoded by SEQ ID NO:4 and at least one mutation at a position corresponding to an amino acid position in the A-domain of the HMA polypeptide encoded by SEQ ID NO: 3.

More suitably, the variant comprises at least one mutation at a position corresponding to amino acid position 438 of the P/N-domain loop encoded by SEQ ID NO: 3 and at least one mutation at amino acid position 265 in the A-domain of the HMA polypeptide encoded by SEQ ID NO: 4.

More suitably, the variant comprises at least one mutation at a position corresponding to amino acid position 438 of the P/N-domain loop encoded by SEQ ID NO: 4 and at least one mutation at amino acid position 265 in the A-domain of the HMA polypeptide encoded by SEQ ID NO: 3.

Suitably, the variant comprises one or more of the mutations selected from the group consisting of: (i) a nonsense mutation at a position corresponding to amino acid position 293 of SEQ ID NO:1 and a nonsense mutation at a position corresponding to amino acid position 561 of SEQ ID NO:2, suitably, wherein the mutations are Q293* and Q561*, wherein * denotes a stop codon; (ii) a nonsense mutation at a position corresponding to amino acid position 293 of SEQ ID NO:1 and a nonsense mutation at a position corresponding to amino acid position 265 of SEQ ID NO:2, suitably, wherein the mutations are Q293* and W265*, wherein * denotes a stop codon; (iii) a missense mutation at a position corresponding to amino acid position 296 of SEQ ID NO:1 and a nonsense mutation at a position corresponding to amino acid position 561 of SEQ ID NO:2, suitably, wherein the mutations are E296K and Q561*, wherein * denotes a stop codon; (iv) a missense mutation at a position corresponding to amino acid position 402 of SEQ ID NO:1 and a nonsense mutation at a position corresponding to amino acid position 561 of SEQ ID NO:2, suitably, wherein the mutations are T402I and Q561*, wherein * denotes a stop codon; (v) a missense mutation at a position corresponding to amino acid position 251 of SEQ ID NO:1 and a nonsense mutation at a position corresponding to amino acid position 561 of SEQ ID NO:2, suitably, wherein the mutations are G251D and Q561*, wherein * denotes a stop codon; (vi) a nonsense mutation at a position corresponding to amino acid position 464 of SEQ ID NO:1 and a nonsense mutation at a position corresponding to amino acid position 561 of SEQ ID NO:2, suitably, wherein the mutations are Q464* and Q561*, wherein * denotes a stop codon; (vii) a nonsense mutation at a position corresponding to amino acid position 293 of SEQ ID NO:1 and a missense mutation at a position corresponding to amino acid position 223 of a non-mutated sequence set forth in SEQ ID NO:2, suitably, wherein the mutations are Q293* and L223F, wherein * denotes a stop codon; (viii) a nonsense mutation at a position corresponding to amino acid position 293 of SEQ ID NO:1 and a missense mutation at a position corresponding to amino acid position 234 of a non-mutated sequence set forth in SEQ ID NO:2, suitably, wherein the mutations are Q293* and D234N, wherein * denotes a stop codon; (ix) a nonsense mutation at a position corresponding to amino acid position 293 of SEQ ID NO:1 and a missense mutation at a position corresponding to amino acid position 235 of a non-mutated sequence set forth in SEQ ID NO:2, suitably, wherein the mutations are Q293* and G235E, wherein * denotes a stop codon; or (x) a missense mutation at a position corresponding to amino acid position 438 of SEQ ID NO:1 and a nonsense mutation at a position corresponding to amino acid position 265 of a non-mutated sequence set forth in SEQ ID NO:2, suitably, wherein the mutations are H438Y and W265*, wherein * denotes a stop codon.

Suitably, the variant comprises one or more of the mutations selected from the group consisting of: (i) a nonsense mutation at a position corresponding to amino acid position 293 of SEQ ID NO:2 and a nonsense mutation at a position corresponding to amino acid position 561 of SEQ ID NO:1, suitably, wherein the mutations are Q293* and Q561*, wherein * denotes a stop codon; (ii) a nonsense mutation at a position corresponding to amino acid position 293 of SEQ ID NO:2 and a nonsense mutation at a position corresponding to amino acid position 265 of SEQ ID NO:1, suitably, wherein the mutations are Q293* and W265*, wherein * denotes a stop codon; (iii) a missense mutation at a position corresponding to amino acid position 296 of SEQ ID NO:2 and a nonsense mutation at a position corresponding to amino acid position 561 of SEQ ID NO:1, suitably, wherein the mutations are E296K and Q561*, wherein * denotes a stop codon; (iv) a missense mutation at a position corresponding to amino acid position 402 of SEQ ID NO:2 and a nonsense mutation at a position corresponding to amino acid position 561 of SEQ ID NO:1, suitably, wherein the mutations are T402I and Q561*, wherein * denotes a stop codon; (v) a missense mutation at a position corresponding to amino acid position 251 of SEQ ID NO:2 and a nonsense mutation at a position corresponding to amino acid position 561 of SEQ ID NO:1, suitably, wherein the mutations are G251D and Q561*, wherein * denotes a stop codon; (vi) a nonsense mutation at a position corresponding to amino acid position 464 of SEQ ID NO:2 and a nonsense mutation at a position corresponding to amino acid position 561 of SEQ ID NO:1, suitably, wherein the mutations are Q464* and Q561*, wherein * denotes a stop codon; (vii) a nonsense mutation at a position corresponding to amino acid position 293 of SEQ ID NO:2 and a missense mutation at a position corresponding to amino acid position 223 of a non-mutated sequence set forth in SEQ ID NO:1, suitably, wherein the mutations are Q293* and L223F, wherein * denotes a stop codon; (viii) a nonsense mutation at a position corresponding to amino acid position 293 of SEQ ID NO:2 and a missense mutation at a position corresponding to amino acid position 234 of a non-mutated sequence set forth in SEQ ID NO:1, suitably, wherein the mutations are Q293* and D234N, wherein * denotes a stop codon; (ix) a nonsense mutation at a position corresponding to amino acid position 293 of SEQ ID NO:2 and a missense mutation at a position corresponding to amino acid position 235 of a non-mutated sequence set forth in SEQ ID NO:1, suitably, wherein the mutations are Q293* and G235E, wherein * denotes a stop codon; or (x) a missense mutation at a position corresponding to amino acid position 438 of SEQ ID NO:2 and a nonsense mutation at a position corresponding to amino acid position 265 of a non-mutated sequence set forth in SEQ ID NO:1, suitably, wherein the mutations are H438Y and W265*, wherein * denotes a stop codon.

It is contemplated that any one of the nonsense mutations can be combined with any one of the missense mutations described herein.

A summary of the data obtained using plants containing the above-mentioned variants when grown outside in the field is set forth in Table 4, 5 and 6. Plants comprising the double mutant Q293*/Q561* or Q293*/W265* or Q464*/Q561* or Q293*/G235E or E296K/Q561* or T402I/Q561* exhibit around 80-96% Cd reduction. Plants comprising the double mutant G251D/Q561* exhibit around 33-70% Cd reduction. Plants comprising the double mutant Q293*/L223F or Q293*/D234N exhibit around 27-37% Cd reduction. At an early stage and under certain conditions delayed plant development is observed for the double mutants Q293*/Q561* or Q293*/W265* or Q464*/Q561* or Q293*/G235E or E296K/Q561* or T402I/Q561*. However, at harvest time, no clear phenotypic differences can be observed between each of the mutants and the control. G251D/Q561* shows normal growth and development. Although Q293*/Q561* or Q293*/W265* or Q464*/Q561* or E296K/Q561* or Q293*/G235E might show necrotic lesions on their leaves at an early stage, depending on environmental conditions, the presence of necrotic lesions is not observed under most conditions at harvest time in the field. The other mutation combinations tested (G382R/Q561*, V351M/Q561*, A188V/Q561*, Q293*/A369V, Q293*/A374V, T189I/Q561*, Q293*/S27L, Q293*/A188V, G128E/Q561*) do not lead to significant or greater than 20% Cd reduction. Suitably, in certain embodiments, the double mutant is not G382R/Q561* or V351M/Q561* or A188V/Q561* or Q293*/A369V or Q293*/A374V or T189I/Q561* or Q293*/S27L or Q293*/A188V or G128E/Q561*.

Data for some of these double mutants when grown in the greenhouse is shown in Table 8. As can be seen from a comparison of Table 4 (field trial) and Table 8 (greenhouse), the level of Cd reduction for the various mutation combinations generally correspond to each other. Further double mutants have been tested in the greenhouse. The results of these data are presented in Table 9. In view of the general agreement on the level of Cd reduction for the double mutants presented in Tables 4 and 8 for the field data and greenhouse data, it is predicted that the greenhouse data presented in Table 9 will also generally correspond to the results that will be obtained the field. The mutation combination H438Y/W265* was tested under greenhouse conditions only where it led to around 58% Cd reduction; phenotypic changes were not observed (Table 9).

In certain embodiments, the double mutants Q293*/Q561* or Q293*/W265* or E296K/Q561* or T402I/Q561* or Q464*/Q561* or Q293*/G235E are preferred because they exhibit about 80% or more Cd reduction in the field. In one embodiment of this preferred combination, the mutant plant or part thereof comprises one or more of the mutations selected from the group consisting of: (i) a nonsense mutation at a position corresponding to amino acid position 293 of SEQ ID NO:1 and a nonsense mutation at a position corresponding to amino acid position 561 of SEQ ID NO:2, suitably, wherein the mutations are Q293* and Q561*, wherein * denotes a stop codon; (ii) a nonsense mutation at a position corresponding to amino acid position 293 of SEQ ID NO:1 and a nonsense mutation at a position corresponding to amino acid position 265 of SEQ ID NO:2, suitably, wherein the mutations are Q293* and W265*, wherein * denotes a stop codon; (iii) a missense mutation at a position corresponding to amino acid position 296 of SEQ ID NO:1 and a nonsense mutation at a position corresponding to amino acid position 561 of SEQ ID NO:2, suitably, wherein the mutations are E296K and Q561*, wherein * denotes a stop codon; (iv) a missense mutation at a position corresponding to amino acid position 402 of SEQ ID NO:1 and a nonsense mutation at a position corresponding to amino acid position 561 of SEQ ID NO:2, suitably, wherein the mutations are T402I and Q561*, wherein * denotes a stop codon; (v) a nonsense mutation at a position corresponding to amino acid position 464 of SEQ ID NO:1 and a nonsense mutation at a position corresponding to amino acid position 561 of SEQ ID NO:2, suitably, wherein the mutations are Q464* and Q561*, wherein * denotes a stop codon; (vi) a nonsense mutation at a position corresponding to amino acid position 293 of SEQ ID NO:1 and a missense mutation at a position corresponding to amino acid position 235 of SEQ ID NO:2, suitably, wherein the mutations are Q293* and G235E, wherein * denotes a stop codon.

In one embodiment of this preferred combination, the mutant plant or part thereof comprises one or more of the mutations selected from the group consisting of: (i) a nonsense mutation at a position corresponding to amino acid position 293 of SEQ ID NO:2 and a nonsense mutation at a position corresponding to amino acid position 561 of SEQ ID NO:1, suitably, wherein the mutations are Q293* and Q561*, wherein * denotes a stop codon; (ii) a nonsense mutation at a position corresponding to amino acid position 293 of SEQ ID NO:2 and a nonsense mutation at a position corresponding to amino acid position 265 of SEQ ID NO:1, suitably, wherein the mutations are Q293* and W265*, wherein * denotes a stop codon; (iii) a missense mutation at a position corresponding to amino acid position 296 of SEQ ID NO:2 and a nonsense mutation at a position corresponding to amino acid position 561 of SEQ ID NO:1, suitably, wherein the mutations are E296K and Q561*, wherein * denotes a stop codon; (iv) a missense mutation at a position corresponding to amino acid position 402 of SEQ ID NO:2 and a nonsense mutation at a position corresponding to amino acid position 561 of SEQ ID NO:1, suitably, wherein the mutations are T402I and Q561*, wherein * denotes a stop codon; (v) a nonsense mutation at a position corresponding to amino acid position 464 of SEQ ID NO:2 and a nonsense mutation at a position corresponding to amino acid position 561 of SEQ ID NO:1, suitably, wherein the mutations are Q464* and Q561*, wherein * denotes a stop codon; (vi) a nonsense mutation at a position corresponding to amino acid position 293 of SEQ ID NO:2 and a missense mutation at a position corresponding to amino acid position 235 of SEQ ID NO:1, suitably, wherein the mutations are Q293* and G235E, wherein * denotes a stop codon.

In certain embodiments, the double mutants G251D/Q561* or H438Y/W265* or Q293*/L223F or Q293*/D234N are preferred (for example, for introduction into plants—such as tobacco, for example, Burley tobacco) because they exhibit 27-70% Cd reduction and are likely not to interfere with growth. In one embodiment of this preferred combination, the mutant plant or part thereof comprises one or more of the mutations selected from the group consisting of: (i) a missense mutation at a position corresponding to amino acid position 251 of SEQ ID NO:1 and a nonsense mutation at a position corresponding to amino acid position 561 of SEQ ID NO:2, suitably, wherein the mutations are G251D and Q561*, wherein * denotes a stop codon; (ii) a missense mutation at a position corresponding to amino acid position 438 of SEQ ID NO:1 and a nonsense mutation at a position corresponding to amino acid position 265 of SEQ ID NO:2, suitably, wherein the mutations are H438Y and W265*, wherein * denotes a stop codon; (iii) a nonsense mutation at a position corresponding to amino acid position 293 of SEQ ID NO:1 and a missense mutation at a position corresponding to amino acid position 223 of SEQ ID NO:2, suitably, wherein the mutations are Q293* and L223F, wherein * denotes a stop codon; (iv) a nonsense mutation at a position corresponding to amino acid position 293 of SEQ ID NO:1 and a missense mutation at a position corresponding to amino acid position 234 of SEQ ID NO:2, suitably, wherein the mutations are Q293* and D234N, wherein * denotes a stop codon.

In one embodiment of this preferred combination, the mutant plant or part thereof comprises one or more of the mutations selected from the group consisting of: (i) a missense mutation at a position corresponding to amino acid position 251 of SEQ ID NO:2 and a nonsense mutation at a position corresponding to amino acid position 561 of SEQ ID NO:1, suitably, wherein the mutations are G251D and Q561*, wherein * denotes a stop codon; (ii) a missense mutation at a position corresponding to amino acid position 438 of SEQ ID NO:2 and a nonsense mutation at a position corresponding to amino acid position 265 of SEQ ID NO:1, suitably, wherein the mutations are H438Y and W265*, wherein * denotes a stop codon; (iii) a nonsense mutation at a position corresponding to amino acid position 293 of SEQ ID NO:2 and a missense mutation at a position corresponding to amino acid position 223 of SEQ ID NO:1, suitably, wherein the mutations are Q293* and L223F, wherein * denotes a stop codon; (iv) a nonsense mutation at a position corresponding to amino acid position 293 of SEQ ID NO:2 and a missense mutation at a position corresponding to amino acid position 234 of SEQ ID NO:1, suitably, wherein the mutations are Q293* and D234N, wherein * denotes a stop codon.

In certain embodiments, the double mutant T402I/Q561* is preferred since it exhibits around 90% Cd reduction and acceptable morphology even at early growing stage. Thus, according to this embodiment, the mutant plant or part thereof comprises a missense mutation at a position corresponding to amino acid position 402 of SEQ ID NO:1 and a nonsense mutation at a position corresponding to amino acid position 561 of SEQ ID NO:2, suitably, wherein the mutations are T402I and Q561*, wherein * denotes a stop codon.

Combinations of the mutations described herein are also contemplated. In particular, different combinations of each of the single mutations in the double mutants are contemplated. Examples of such combinations are shown in Tables 11 and 12 and described below. In one embodiment, the variant comprises at least one mutation at a position corresponding to amino acid position 464 of the P-domain of the third loop of the HMA polypeptide encoded by SEQ ID NO: 3 and at least one mutation at a position corresponding to amino acid position 265 of the second cytoplasmic loop of the A-domain of the HMA polypeptide encoded by SEQ ID NO: 4.

In one embodiment, the variant comprises at least one mutation at a position corresponding to amino acid position 464 of the P-domain of the third loop of the HMA polypeptide encoded by SEQ ID NO: 4 and at least one mutation at a position corresponding to amino acid position 265 of the second cytoplasmic loop of the A-domain of the HMA polypeptide encoded by SEQ ID NO: 3.

In one embodiment, the variant comprises at least one mutation at a position corresponding to amino acid position 464 of the P-domain of the third loop of the HMA polypeptide encoded by SEQ ID NO: 3 and at least one mutation at a position corresponding to amino acid position 223 of the second cytoplasmic loop of the A-domain of the HMA polypeptide encoded by SEQ ID NO: 4.

In one embodiment, the variant comprises at least one mutation at a position corresponding to amino acid position 464 of the P-domain of the third loop of the HMA polypeptide encoded by SEQ ID NO: 4 and at least one mutation at a position corresponding to amino acid position 223 of the second cytoplasmic loop of the A-domain of the HMA polypeptide encoded by SEQ ID NO: 3.

In one embodiment, the variant comprises at least one mutation at a position corresponding to amino acid position 464 of the P-domain of the third loop of the HMA polypeptide encoded by SEQ ID NO: 3 and at least one mutation at a position corresponding to amino acid position 234 of the second cytoplasmic loop of the A-domain of the HMA polypeptide encoded by SEQ ID NO: 4.

In one embodiment, the variant comprises at least one mutation at a position corresponding to amino acid position 464 of the P-domain of the third loop of the HMA polypeptide encoded by SEQ ID NO: 4 and at least one mutation at a position corresponding to amino acid position 234 of the second cytoplasmic loop of the A-domain of the HMA polypeptide encoded by SEQ ID NO: 3.

In one embodiment, the variant comprises at least one mutation at a position corresponding to amino acid position 464 of the P-domain of the third loop of the HMA polypeptide encoded by SEQ ID NO: 3 and at least one mutation at a position corresponding to amino acid position 235 of the second cytoplasmic loop of the A-domain of the HMA polypeptide encoded by SEQ ID NO: 4.

In one embodiment, the variant comprises at least one mutation at a position corresponding to amino acid position 464 of the P-domain of the third loop of the HMA polypeptide encoded by SEQ ID NO: 4 and at least one mutation at a position corresponding to amino acid position 235 of the second cytoplasmic loop of the A-domain of the HMA polypeptide encoded by SEQ ID NO: 3.

In one embodiment, the variant comprises at least one mutation at a position corresponding to amino acid position 296 of the second cytoplasmic loop of the A-domain of the HMA polypeptide encoded by SEQ ID NO: 3 and at least one mutation at a position corresponding to amino acid position 265 of the second cytoplasmic loop of the A-domain of the HMA polypeptide encoded by SEQ ID NO: 4.

In one embodiment, the variant comprises at least one mutation at a position corresponding to amino acid position 296 of the second cytoplasmic loop of the A-domain of the HMA polypeptide encoded by SEQ ID NO: 4 and at least one mutation at a position corresponding to amino acid position 265 of the second cytoplasmic loop of the A-domain of the HMA polypeptide encoded by SEQ ID NO: 3.

In one embodiment, the variant comprises at least one mutation at a position corresponding to amino acid position 296 of the second cytoplasmic loop of the A-domain of the HMA polypeptide encoded by SEQ ID NO: 3 and at least one mutation at a position corresponding to amino acid position 223 of the second cytoplasmic loop of the A-domain of the HMA polypeptide encoded by SEQ ID NO: 4.

In one embodiment, the variant comprises at least one mutation at a position corresponding to amino acid position 296 of the second cytoplasmic loop of the A-domain of the HMA polypeptide encoded by SEQ ID NO: 4 and at least one mutation at a position corresponding to amino acid position 223 of the second cytoplasmic loop of the A-domain of the HMA polypeptide encoded by SEQ ID NO: 3.

In one embodiment, the variant comprises at least one mutation at a position corresponding to amino acid position 296 of the second cytoplasmic loop of the A-domain of the HMA polypeptide encoded by SEQ ID NO: 3 and at least one mutation at a position corresponding to amino acid position 234 of the second cytoplasmic loop of the A-domain of the HMA polypeptide encoded by SEQ ID NO: 4.

In one embodiment, the variant comprises at least one mutation at a position corresponding to amino acid position 296 of the second cytoplasmic loop of the A-domain of the HMA polypeptide encoded by SEQ ID NO: 4 and at least one mutation at a position corresponding to amino acid position 234 of the second cytoplasmic loop of the A-domain of the HMA polypeptide encoded by SEQ ID NO: 3.

In one embodiment, the variant comprises at least one mutation at a position corresponding to amino acid position 296 of the second cytoplasmic loop of the A-domain of the HMA polypeptide encoded by SEQ ID NO: 3 and at least one mutation at a position corresponding to amino acid position 235 of the second cytoplasmic loop of the A-domain of the HMA polypeptide encoded by SEQ ID NO: 4.

In one embodiment, the variant comprises at least one mutation at a position corresponding to amino acid position 296 of the second cytoplasmic loop of the A-domain of the HMA polypeptide encoded by SEQ ID NO: 4 and at least one mutation at a position corresponding to amino acid position 235 of the second cytoplasmic loop of the A-domain of the HMA polypeptide encoded by SEQ ID NO: 3.

In one embodiment, the variant comprises at least one mutation at a position corresponding to amino acid position 402 of the third cytoplasmic loop of the P/N-domain of the HMA polypeptide encoded by SEQ ID NO: 3 and at least one mutation at a position corresponding to amino acid position 265 of the second cytoplasmic loop of the A-domain of the HMA polypeptide encoded by SEQ ID NO: 4.

In one embodiment, the variant comprises at least one mutation at a position corresponding to amino acid position 402 of the third cytoplasmic loop of the P/N-domain of the HMA polypeptide encoded by SEQ ID NO: 4 and at least one mutation at a position corresponding to amino acid position 265 of the second cytoplasmic loop of the A-domain of the HMA polypeptide encoded by SEQ ID NO: 3.

In one embodiment, the variant comprises at least one mutation at a position corresponding to amino acid position 402 of the third cytoplasmic loop of the P/N-domain of the HMA polypeptide encoded by SEQ ID NO: 3 and at least one mutation at a position corresponding to amino acid position 223 of the second cytoplasmic loop of the A-domain of the HMA polypeptide encoded by SEQ ID NO: 4.

In one embodiment, the variant comprises at least one mutation at a position corresponding to amino acid position 402 of the third cytoplasmic loop of the P/N-domain of the HMA polypeptide encoded by SEQ ID NO: 4 and at least one mutation at a position corresponding to amino acid position 223 of the second cytoplasmic loop of the A-domain of the HMA polypeptide encoded by SEQ ID NO: 3.

In one embodiment, the variant comprises at least one mutation at a position corresponding to amino acid position 402 of the third cytoplasmic loop of the P/N-domain of the HMA polypeptide encoded by SEQ ID NO: 3 and at least one mutation at a position corresponding to amino acid position 234 of the second cytoplasmic loop of the A-domain of the HMA polypeptide encoded by SEQ ID NO: 4.

In one embodiment, the variant comprises at least one mutation at a position corresponding to amino acid position 402 of the third cytoplasmic loop of the P/N-domain of the HMA polypeptide encoded by SEQ ID NO: 4 and at least one mutation at a position corresponding to amino acid position 234 of the second cytoplasmic loop of the A-domain of the HMA polypeptide encoded by SEQ ID NO: 3.

In one embodiment, the variant comprises at least one mutation at a position corresponding to amino acid position 402 of the third cytoplasmic loop of the P/N-domain of the HMA polypeptide encoded by SEQ ID NO: 3 and at least one mutation at a position corresponding to amino acid position 235 of the second cytoplasmic loop of the A-domain of the HMA polypeptide encoded by SEQ ID NO: 4.

In one embodiment, the variant comprises at least one mutation at a position corresponding to amino acid position 402 of the third cytoplasmic loop of the P/N-domain of the HMA polypeptide encoded by SEQ ID NO: 4 and at least one mutation at a position corresponding to amino acid position 235 of the second cytoplasmic loop of the A-domain of the HMA polypeptide encoded by SEQ ID NO: 3.

In one embodiment, the variant comprises at least one mutation at a position corresponding to amino acid position 251 of the second cytoplasmic loop of the A-domain of the HMA polypeptide encoded by SEQ ID NO: 3 and at least one mutation at a position corresponding to amino acid position 265 of the second cytoplasmic loop of the A-domain of the HMA polypeptide encoded by SEQ ID NO: 4.

In one embodiment, the variant comprises at least one mutation at a position corresponding to amino acid position 251 of the second cytoplasmic loop of the A-domain of the HMA polypeptide encoded by SEQ ID NO: 4 and at least one mutation at a position corresponding to amino acid position 265 of the second cytoplasmic loop of the A-domain of the HMA polypeptide encoded by SEQ ID NO: 3.

In one embodiment, the variant comprises at least one mutation at a position corresponding to amino acid position 251 of the second cytoplasmic loop of the A-domain of the HMA polypeptide encoded by SEQ ID NO: 3 and at least one mutation at a position corresponding to amino acid position 223 of the second cytoplasmic loop of the A-domain of the HMA polypeptide encoded by SEQ ID NO: 4.

In one embodiment, the variant comprises at least one mutation at a position corresponding to amino acid position 251 of the second cytoplasmic loop of the A-domain of the HMA polypeptide encoded by SEQ ID NO: 4 and at least one mutation at a position corresponding to amino acid position 223 of the second cytoplasmic loop of the A-domain of the HMA polypeptide encoded by SEQ ID NO: 3.

In one embodiment, the variant comprises at least one mutation at a position corresponding to amino acid position 251 of the second cytoplasmic loop of the A-domain of the HMA polypeptide encoded by SEQ ID NO: 3 and at least one mutation at a position corresponding to amino acid position 234 of the second cytoplasmic loop of the A-domain of the HMA polypeptide encoded by SEQ ID NO: 4.

In one embodiment, the variant comprises at least one mutation at a position corresponding to amino acid position 251 of the second cytoplasmic loop of the A-domain of the HMA polypeptide encoded by SEQ ID NO: 4 and at least one mutation at a position corresponding to amino acid position 234 of the second cytoplasmic loop of the A-domain of the HMA polypeptide encoded by SEQ ID NO: 3.

In one embodiment, the variant comprises at least one mutation at a position corresponding to amino acid position 251 of the second cytoplasmic loop of the A-domain of the HMA polypeptide encoded by SEQ ID NO: 3 and at least one mutation at a position corresponding to amino acid position 235 of the second cytoplasmic loop of the A-domain of the HMA polypeptide encoded by SEQ ID NO: 4.

In one embodiment, the variant comprises at least one mutation at a position corresponding to amino acid position 251 of the second cytoplasmic loop of the A-domain of the HMA polypeptide encoded by SEQ ID NO: 4 and at least one mutation at a position corresponding to amino acid position 235 of the second cytoplasmic loop of the A-domain of the HMA polypeptide encoded by SEQ ID NO: 3.

In one embodiment, the variant comprises at least one mutation at a position corresponding to amino acid position 438 of the third cytoplasmic loop of the P/N-domain of the HMA polypeptide encoded by SEQ ID NO: 3 and at least one mutation at a position corresponding to amino acid position 561 of the third cytoplasmic loop of the P/N-domain of the HMA polypeptide encoded by SEQ ID NO: 4.

In one embodiment, the variant comprises at least one mutation at a position corresponding to amino acid position 438 of the third cytoplasmic loop of the P/N-domain of the HMA polypeptide encoded by SEQ ID NO: 4 and at least one mutation at a position corresponding to amino acid position 561 of the third cytoplasmic loop of the P/N-domain of the HMA polypeptide encoded by SEQ ID NO: 3.

In one embodiment, the variant comprises at least one mutation at a position corresponding to amino acid position 438 of the third cytoplasmic loop of the P/N-domain of the HMA polypeptide encoded by SEQ ID NO: 3 and at least one mutation at a position corresponding to amino acid position 223 of the second cytoplasmic loop of the A-domain of the HMA polypeptide encoded by SEQ ID NO: 4.

In one embodiment, the variant comprises at least one mutation at a position corresponding to amino acid position 438 of the third cytoplasmic loop of the P/N-domain of the HMA polypeptide encoded by SEQ ID NO: 4 and at least one mutation at a position corresponding to amino acid position 223 of the second cytoplasmic loop of the A-domain of the HMA polypeptide encoded by SEQ ID NO: 3.

In one embodiment, the variant comprises at least one mutation at a position corresponding to amino acid position 438 of the third cytoplasmic loop of the P/N-domain of the HMA polypeptide encoded by SEQ ID NO: 3 and at least one mutation at a position corresponding to amino acid position 234 of the second cytoplasmic loop of the A-domain of the HMA polypeptide encoded by SEQ ID NO: 4.

In one embodiment, the variant comprises at least one mutation at a position corresponding to amino acid position 438 of the third cytoplasmic loop of the P/N-domain of the HMA polypeptide encoded by SEQ ID NO: 4 and at least one mutation at a position corresponding to amino acid position 234 of the second cytoplasmic loop of the A-domain of the HMA polypeptide encoded by SEQ ID NO: 3.

In one embodiment, the variant comprises at least one mutation at a position corresponding to amino acid position 438 of the third cytoplasmic loop of the P/N-domain of the HMA polypeptide encoded by SEQ ID NO: 3 and at least one mutation at a position corresponding to amino acid position 235 of the second cytoplasmic loop of the A-domain of the HMA polypeptide encoded by SEQ ID NO: 4.

In one embodiment, the variant comprises at least one mutation at a position corresponding to amino acid position 438 of the third cytoplasmic loop of the P/N-domain of the HMA polypeptide encoded by SEQ ID NO: 4 and at least one mutation at a position corresponding to amino acid position 235 of the second cytoplasmic loop of the A-domain of the HMA polypeptide encoded by SEQ ID NO: 3.

Suitably, the variant comprises one or more of the mutations selected from the group consisting of: (i) a nonsense mutation at a position corresponding to amino acid position 464 of SEQ ID NO:1 and a nonsense mutation at a position corresponding to amino acid position 265 of SEQ ID NO:2, suitably, wherein the mutations are Q464* and W265**, wherein * denotes a stop codon; (ii) a nonsense mutation at a position corresponding to amino acid position 464 of SEQ ID NO:1 and a missense mutation at a position corresponding to amino acid position 223 of SEQ ID NO:2, suitably, wherein the mutations are Q464* and L223F, wherein * denotes a stop codon; (iii) a nonsense mutation at a position corresponding to amino acid position 464 of SEQ ID NO:1 and a missense mutation at a position corresponding to amino acid position 234 of SEQ ID NO:2, suitably, wherein the mutations are Q464* and D234N, wherein * denotes a stop codon; (iv) a nonsense mutation at a position corresponding to amino acid position 464 of SEQ ID NO:1 and a missense mutation at a position corresponding to amino acid position 235 of SEQ ID NO:2, suitably, wherein the mutations are Q464* and G235E, wherein * denotes a stop codon; (v) a missense mutation at a position corresponding to amino acid position 296 of SEQ ID NO:1 and a nonsense mutation at a position corresponding to amino acid position 265 of SEQ ID NO:2, suitably, wherein the mutations are E296K and W265*, wherein * denotes a stop codon; (vi) a missense mutation at a position corresponding to amino acid position 296 of SEQ ID NO:1 and a missense mutation at a position corresponding to amino acid position 223 of SEQ ID NO:2, suitably, wherein the mutations are E296K and L223F; (vii) a missense mutation at a position corresponding to amino acid position 296 of SEQ ID NO:1 and a missense mutation at a position corresponding to amino acid position 234 of SEQ ID NO:2, suitably, wherein the mutations are E296K and D234N, wherein * denotes a stop codon; (viii) a missense mutation at a position corresponding to amino acid position 296 of SEQ ID NO:1 and a missense mutation at a position corresponding to amino acid position 235 of SEQ ID NO:2, suitably, wherein the mutations are E296K and G235E; (ix) a missense mutation at a position corresponding to amino acid position 402 of SEQ ID NO:1 and a nonsense mutation at a position corresponding to amino acid position 265 of SEQ ID NO:2, suitably, wherein the mutations are T402I and W265*, wherein * denotes a stop codon; (x) a missense mutation at a position corresponding to amino acid position 402 of SEQ ID NO:1 and a missense mutation at a position corresponding to amino acid position 223 of SEQ ID NO:2, suitably, wherein the mutations are T402I and L223F; (xi) a missense mutation at a position corresponding to amino acid position 402 of SEQ ID NO:1 and a missense mutation at a position corresponding to amino acid position 234 of SEQ ID NO:2, suitably, wherein the mutations are T402I and D234N; (xii) a missense mutation at a position corresponding to amino acid position 402 of SEQ ID NO:1 and a missense mutation at a position corresponding to amino acid position 235 of SEQ ID NO:2, suitably, wherein the mutations are T402I and G235E; (xiii) a missense mutation at a position corresponding to amino acid position 251 of SEQ ID NO:1 and a nonsense mutation at a position corresponding to amino acid position 265 of SEQ ID NO:2, suitably, wherein the mutations are G251D and W265*, wherein * denotes a stop codon; (xiv) a missense mutation at a position corresponding to amino acid position 251 of SEQ ID NO:1 and a missense mutation at a position corresponding to amino acid position 223 of SEQ ID NO:2, suitably, wherein the mutations are G251D and L223F; (xv) a missense mutation at a position corresponding to amino acid position 251 of SEQ ID NO:1 and a missense mutation at a position corresponding to amino acid position 234 of SEQ ID NO:2, suitably, wherein the mutations are G251D and D234N; (xvi) a missense mutation at a position corresponding to amino acid position 251 of SEQ ID NO:1 and a missense mutation at a position corresponding to amino acid position 235 of SEQ ID NO:2, suitably, wherein the mutations are G251D and G235E; (xvii) a missense mutation at a position corresponding to amino acid position 438 of SEQ ID NO:1 and a nonsense mutation at a position corresponding to amino acid position 561 of SEQ ID NO:2, suitably, wherein the mutations are H438Y and Q561*, wherein * denotes a stop codon; (xviii) a missense mutation at a position corresponding to amino acid position 438 of SEQ ID NO:1 and a missense mutation at a position corresponding to amino acid position 223 of SEQ ID NO:2, suitably, wherein the mutations are H438Y and L223F, wherein * denotes a stop codon; (xix) a missense mutation at a position corresponding to amino acid position 438 of SEQ ID NO:1 and a missense mutation at a position corresponding to amino acid position 234 of SEQ ID NO:2, suitably, wherein the mutations are H438Y and D234N, wherein * denotes a stop codon; or (xx) a missense mutation at a position corresponding to amino acid position 438 of SEQ ID NO:1 and a missense mutation at a position corresponding to amino acid position 235 of SEQ ID NO:2, suitably, wherein the mutations are H438Y and G235E, wherein * denotes a stop codon.

Suitably, the variant comprises one or more of the mutations selected from the group consisting of: (i) a nonsense mutation at a position corresponding to amino acid position 464 of SEQ ID NO:2 and a nonsense mutation at a position corresponding to amino acid position 265 of SEQ ID NO:1, suitably, wherein the mutations are Q464* and W265**, wherein * denotes a stop codon; (ii) a nonsense mutation at a position corresponding to amino acid position 464 of SEQ ID NO:2 and a missense mutation at a position corresponding to amino acid position 223 of SEQ ID NO:1, suitably, wherein the mutations are Q464* and L223F, wherein * denotes a stop codon; (iii) a nonsense mutation at a position corresponding to amino acid position 464 of SEQ ID NO:2 and a missense mutation at a position corresponding to amino acid position 234 of SEQ ID NO:1, suitably, wherein the mutations are Q464* and D234N, wherein * denotes a stop codon; (iv) a nonsense mutation at a position corresponding to amino acid position 464 of SEQ ID NO:2 and a missense mutation at a position corresponding to amino acid position 235 of SEQ ID NO:1, suitably, wherein the mutations are Q464* and G235E, wherein * denotes a stop codon; (v) a missense mutation at a position corresponding to amino acid position 296 of SEQ ID NO:2 and a nonsense mutation at a position corresponding to amino acid position 265 of SEQ ID NO:1, suitably, wherein the mutations are E296K and W265*, wherein * denotes a stop codon; (vi) a missense mutation at a position corresponding to amino acid position 296 of SEQ ID NO:2 and a missense mutation at a position corresponding to amino acid position 223 of SEQ ID NO:1, suitably, wherein the mutations are E296K and L223F; (vii) a missense mutation at a position corresponding to amino acid position 296 of SEQ ID NO:2 and a missense mutation at a position corresponding to amino acid position 234 of SEQ ID NO:1, suitably, wherein the mutations are E296K and D234N, wherein * denotes a stop codon; (viii) a missense mutation at a position corresponding to amino acid position 296 of SEQ ID NO:2 and a missense mutation at a position corresponding to amino acid position 235 of SEQ ID NO:1, suitably, wherein the mutations are E296K and G235E; (ix) a missense mutation at a position corresponding to amino acid position 402 of SEQ ID NO:2 and a nonsense mutation at a position corresponding to amino acid position 265 of SEQ ID NO:1, suitably, wherein the mutations are T402I and W265*, wherein * denotes a stop codon; (x) a missense mutation at a position corresponding to amino acid position 402 of SEQ ID NO:2 and a missense mutation at a position corresponding to amino acid position 223 of SEQ ID NO:1, suitably, wherein the mutations are T402I and L223F; (xi) a missense mutation at a position corresponding to amino acid position 402 of SEQ ID NO:2 and a missense mutation at a position corresponding to amino acid position 234 of SEQ ID NO:1, suitably, wherein the mutations are T402I and D234N; (xii) a missense mutation at a position corresponding to amino acid position 402 of SEQ ID NO:2 and a missense mutation at a position corresponding to amino acid position 235 of SEQ ID NO:1, suitably, wherein the mutations are T402I and G235E; (xiii) a missense mutation at a position corresponding to amino acid position 251 of SEQ ID NO:2 and a nonsense mutation at a position corresponding to amino acid position 265 of SEQ ID NO:1, suitably, wherein the mutations are G251D and W265*, wherein * denotes a stop codon; (xiv) a missense mutation at a position corresponding to amino acid position 251 of SEQ ID NO:2 and a missense mutation at a position corresponding to amino acid position 223 of SEQ ID NO:1, suitably, wherein the mutations are G251D and L223F; (xv) a missense mutation at a position corresponding to amino acid position 251 of SEQ ID NO:2 and a missense mutation at a position corresponding to amino acid position 234 of SEQ ID NO:1, suitably, wherein the mutations are G251D and D234N; (xvi) a missense mutation at a position corresponding to amino acid position 251 of SEQ ID NO:2 and a missense mutation at a position corresponding to amino acid position 235 of SEQ ID NO:1, suitably, wherein the mutations are G251D and G235E; (xvii) a missense mutation at a position corresponding to amino acid position 438 of SEQ ID NO:2 and a nonsense mutation at a position corresponding to amino acid position 561 of SEQ ID NO:1, suitably, wherein the mutations are H438Y and Q561*, wherein * denotes a stop codon; (xviii) a missense mutation at a position corresponding to amino acid position 438 of SEQ ID NO:2 and a missense mutation at a position corresponding to amino acid position 223 of SEQ ID NO:1, suitably, wherein the mutations are H438Y and L223F, wherein * denotes a stop codon; (xix) a missense mutation at a position corresponding to amino acid position 438 of SEQ ID NO:2 and a missense mutation at a position corresponding to amino acid position 234 of SEQ ID NO:1, suitably, wherein the mutations are H438Y and D234N, wherein * denotes a stop codon; or (xx) a missense mutation at a position corresponding to amino acid position 438 of SEQ ID NO:2 and a missense mutation at a position corresponding to amino acid position 235 of SEQ ID NO:1, suitably, wherein the mutations are H438Y and G235E, wherein * denotes a stop codon.

A polynucleotide as described herein will generally contain phosphodiester bonds, although in some cases, polynucleotide analogues are included that may have alternate backbones, comprising, for example, phosphoramidate, phosphorothioate, phosphorodithioate, or O-methylphophoroamidite linkages; and peptide polynucleotide backbones and linkages. Other analogue polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogues can be made; alternatively, mixtures of different polynucleotide analogues, and mixtures of naturally occurring polynucleotides and analogues may be made. Isolated HMA4 polynucleotide variants (mutants) are described herein comprising a polynucleotide sequence having at least 65% sequence identity to SEQ ID NO:3 or SEQ ID NO:4 and at least one nucleotide mutation as compared to the wild-type sequences set forth in SEQ ID NO:3 or SEQ ID NO:4. SEQ ID NO:3 and SEQ ID NO:4 are non-mutated sequences. SEQ ID NO: 3 and SEQ ID NO:4 correspond to the polynucleotide sequence of Nicotiana tabacum heavy metal ATPase (NtHMA4.1) GenBank Accession No: HF675181.1 and Nicotiana tabacum heavy metal ATPase (NtHMA4.2) GenBank Accession No: HF937054.1, respectively. Suitably, the isolated polynucleotide comprises, consists or consists essentially of a sequence having at least 65%, 66%, 67%, 68%, 69%, 70%, 75%, 76%, 77%, 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity thereto and at least one nucleotide mutation.

Suitably, the plant comprises at least one mutation in each of SEQ ID NO:3 and SEQ NO:4 and/or a gene fragment that interferes with the translation of an RNA transcript encoding the HMAs set forth in (ii), suitably, where in the mutation is a missense mutation or a nonsense mutation.

A variety of polynucleotide analogues are known, including, for example, phosphoramidate, phosphorothioate, phosphorodithioate, O-methylphophoroamidite linkages and peptide polynucleotide backbones and linkages. Other analogue polynucleotides include those with positive backbones, non-ionic backbones and non-ribose backbones. Polynucleotides containing one or more carbocyclic sugars are also included.

The basic parameters affecting the choice of hybridization conditions for polynucleotides and guidance for devising suitable conditions are described by Sambrook et al., 1989. Using knowledge of the genetic code in combination with the amino acid sequences described herein, sets of degenerate oligonucleotides can be prepared. Such oligonucleotides are useful as primers, for example, in polymerase chain reactions (PCR), whereby DNA fragments are isolated and amplified. In certain embodiments, degenerate primers can be used as probes for genetic libraries. Such libraries would include but are not limited to cDNA libraries, genomic libraries, and even electronic express sequence tag or DNA libraries. Homologous sequences identified by this method would then be used as probes to identify homologues of the sequences identified herein.

Also of potential use are polynucleotides and oligonucleotides (for example, primers or probes) that hybridize under reduced stringency conditions, typically moderately stringent conditions, and commonly highly stringent conditions to the polynucleotide(s) as described herein. The basic parameters affecting the choice of hybridization conditions and guidance for devising suitable conditions can be readily determined by those having ordinary skill in the art based on, for example, the length or base composition of the polynucleotide. One way of achieving moderately stringent conditions involves the use of a prewashing solution containing 5×Standard Sodium Citrate, 0.5% Sodium Dodecyl Sulphate, 1.0 mM Ethylenediaminetetraacetic acid (pH 8.0), hybridization buffer of about 50% formamide, 6×Standard Sodium Citrate, and a hybridization temperature of about 55° C. (or other similar hybridization solutions, such as one containing about 50% formamide, with a hybridization temperature of about 42° C.), and washing conditions of about 60° C., in 0.5×Standard Sodium Citrate, 0.1% Sodium Dodecyl Sulphate. Generally, highly stringent conditions are defined as hybridization conditions as above, but with washing at approximately 68° C., 0.2×Standard Sodium Citrate, 0.1% Sodium Dodecyl Sulphate. SSPE (1×SSPE is 0.15 M sodium chloride, 10 mM sodium phosphate, and 1.25 mM Ethylenediaminetetraacetic acid, pH 7.4) can be substituted for Standard Sodium Citrate (1×Standard Sodium Citrate is 0.15 M sodium chloride and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook, et al., 1989). When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature of the hybrid, where melting temperature is determined according to the following equations. For hybrids less than 18 base pairs in length, melting temperature (° C.)=2(number of A+T bases)+4(number of G+C bases). For hybrids above 18 base pairs in length, melting temperature (° C.)=81.5+16.6(log 10 [Na+])+0.41(% G+C)−(600/N), where N is the number of bases in the hybrid, and [Na+] is the concentration of sodium ions in the hybridization buffer ([Na+] for 1×Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 70%, 75%, 80%, 85%, 90%, 95%, 96%, 97%, 98%, 99% or 100%) with a polynucleotide to which it hybridizes.

Isolated polynucleotides are also contemplated. An "isolated" polynucleotide is free of sequences (optimally protein encoding sequences) that naturally flank the polynucleotide (for example, sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

Recombinant constructs can be used to transform plants or plant cells. A recombinant polynucleotide construct can comprise a polynucleotide encoding one or more variant polypeptides as described herein, operably linked to a regulatory region suitable for expressing the variant polypeptide. Thus, a polynucleotide can comprise a coding sequence that encodes the variant polypeptide. The plant or plant cell can comprise a genome that has been altered by the stable integration of recombinant DNA. Recombinant DNA includes DNA which has been genetically engineered and constructed outside of a cell and includes DNA containing naturally occurring DNA or cDNA or synthetic DNA. The plant can include a plant regenerated from an originally-transformed plant cell and progeny plants from later generations or crosses of a transformed plant. Suitably, the modification alters the expression or activity of the HMA polynucleotide or the HMA polypeptide described herein as compared to a control plant. In certain embodiments, the use of non-GMO approaches to reduce Cd accumulation through the use of gene inactivation is used. Thus, for example, the use of mutants featuring one or more nucleotide polymorphisms obtained thought the use of one or more exogenously added chemicals—such as mutagenic, teratogenic, or carcinogenic organic compounds, for example ethyl methanesulfonate (EMS), that produce random mutations in genetic material is used. A DNA library of treated plants can then be screened for mutations in the two HMA4 genes.

Vectors containing recombinant polynucleotide constructs such as those described herein are also provided. Suitable vector backbones include, for example, those routinely used in the art such as plasmids, viruses, artificial chromosomes, bacterial artificial chromosomes, yeast artificial chromosomes, or bacteriophage artificial chromosomes. Suitable expression vectors include, without limitation, plasmids and viral vectors derived from, for example, bacteriophage, baculoviruses, and retroviruses. Numerous vectors and expression systems are commercially available. The vectors can include, for example, origins of replication, scaffold attachment regions or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, beta-glucuronidase, green fluorescent protein, glutathione S-transferase, polyhistidine, c-myc or hemagglutinin sequences typically are expressed as a fusion with the encoded polypeptide. Such tags can be inserted anywhere within the HMA variant polypeptide, including at either the carboxyl or amino terminus.

A plant or plant cell can be transformed by having the recombinant polynucleotide integrated into its genome to become stably transformed. The plant or plant cell described herein can be stably transformed. Stably transformed cells typically retain the introduced polynucleotide with each cell division. A plant or plant cell can be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions. The use of genome editing is also contemplated.

A number of methods are available in the art for transforming a plant cell which are all encompassed herein, including biolistics, gene gun techniques, *Agrobacterium*-mediated transformation, viral vector-mediated transformation and electroporation. The *Agrobacterium* system for integration of foreign DNA into plant chromosomes has been extensively studied, modified, and exploited for plant genetic engineering. Naked recombinant DNA molecules comprising DNA sequences corresponding to the subject purified protein operably linked, in the sense or antisense orientation, to regulatory sequences are joined to appropriate T-DNA sequences by conventional methods. These are introduced into protoplasts by polyethylene glycol techniques or by electroporation techniques, both of which are standard. Alternatively, such vectors comprising recombinant DNA molecules encoding the subject purified protein are introduced into live *Agrobacterium* cells, which then transfer the DNA into the plant cells. Transformation by naked DNA without accompanying T-DNA vector sequences can be accomplished via fusion of protoplasts with DNA-containing liposomes or via electroporation. Naked DNA unaccompanied by T-DNA vector sequences can also be used to transform cells via inert, high velocity microprojectiles.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a HMA variant coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art. Examples of promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Examples of promoters include constitutive promoters that can be activated in most cell types without requiring specific inducers. Examples of promoters for controlling RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters. In addition to plant promoters, other suitable promoters may be derived from bacterial origin for example, the octopine synthase promoter, the nopaline synthase promoter and other promoters derived from Ti plasmids), or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

It is to be understood that reducing or inhibiting the expression or activity of the HMAs described herein may be achieved by various means. For example, inserting one or more mutations into at least one of the genes encoding the HMAs, including deletions, insertions, site specific mutations, zinc-finger nucleases is contemplated.

In one aspect, there is provided a mutant plant or part thereof having at least partially reduced expression or activity of at least two heavy metal ATPases (HMAs), said two HMAs comprising, consisting or consisting essentially of: (i) polypeptides having at least 65% sequence identity to SEQ ID NO:1 and SEQ ID NO:2; (ii) polynucleotides encoding the polypeptides set forth in (i); or (iii) polynucleotides having at least 65% sequence identity to SEQ ID NO:3 and SEQ ID NO:4 encoding HMAs; wherein the mutant plant or part thereof exhibits at least a 27% reduction, as compared to the control plant, in the accumulation of cadmium in leaf when the mutant plant is grown in the field in the presence of naturally or non-naturally occurring cadmium.

The expression or activity of the HMAs can be modulated through the use of one of more mutations that cause a reduction in the expression or function of said gene or protein encoded thereby. Aside from the one or more mutations described herein, the mutant plant or plant cell can have one or more further mutations in one or more other genes or polypeptides. In certain embodiments, the mutants can have one or more further mutations in one or more other genes or polypeptides.

In another aspect, there is provided a method for reducing the level of cadmium in the leaf of a field grown plant comprising the steps of: (a) reducing the expression or activity of two heavy metal ATPases (HMAs), said two HMAs comprising, consisting or consisting essentially of: (i) polypeptides having at least 65% sequence identity to SEQ ID NO:1 and SEQ ID NO:2; (ii) polynucleotides encoding the polypeptides set forth in (i); or (iii) polynucleotides having at least 65% sequence identity to SEQ ID NO:3 and SEQ ID NO:4 encoding HMAs; (b) growing the plant in the field; (c) optionally, measuring the cadmium content in the plant obtained in step (b); and (d) identifying a plant in which the cadmium content therein is reduced in comparison to a control plant in which the expression or activity of the HMAs has not been reduced, suitably, wherein the plant or part thereof exhibits at least a 27% reduction, as compared to the control plant, in the accumulation of cadmium in leaf when the plant is field grown in the presence of naturally or non-naturally occurring cadmium; suitably, wherein the phenotype of the mutant plant or part thereof at harvest time is the same as the control plant at the same harvest time, suitably, wherein the mutant plant or part thereof does not show a biomass (for example, leaf weight) reduction at harvest time as compared to the control plant at the same harvest time. In certain embodiments, the expression or activity of the two HMAs is reduced via the mutagenesis approach described herein or through the use of the mutants that are described herein.

The "harvest time" of a plant will be immediately apparent to a person skilled in the art. In other words, the skilled person will know when a plant is ready for harvesting. By way of example, the person skilled in the art knows when to harvest a tobacco plant because the leaves of the tobacco plant begin to ripen. For certain varieties of tobacco this means that the leaves begin to yellow, which is intended and desired for proper curing. There are also varieties of tobacco that cure from green to brown or from green to yellow to brown. Plants can be harvested as a whole or in part once the part of the plant is ready to harvest. For example, for tobacco plants, the harvest time can be defined for each stalk position. The leaves on the bottom of the tobacco stalk will start to change colour (eg. yellow) first and can be harvested, and the upper leaves will then yellow later on for harvesting. There is also provided a method for identifying one or more genetic alterations in a field grown plant that correlates with reduced levels of cadmium in leaf as compared to a field grown control plant that does not comprise the one or more genetic alterations, said method comprising the steps of: (a) identifying a plant with reduced levels of cadmium in the leaves when grown in the field as compared to a control plant grown in the field, optionally wherein the phenotype of the plant or part thereof at harvest time is the same as the control plant at the same harvest time, suitably, wherein the plant or part thereof does not show a biomass (for example, leaf weight) reduction at harvest time as compared to the control plant at the same harvest time; (b) providing a nucleic acid sample from the plant identified in step (a); and (c) identifying in the nucleic acid sample from step (b) one or more genetic alterations in the polynucleotide sequences encoding HMAs having at least 65% sequence identity to the non-mutated sequences set forth in SEQ ID NO:1 and SEQ ID NO:2 or the polynucleotide sequence having at least 65% sequence identity to SEQ ID NO:3 and SEQ ID NO:4.

In some embodiments, one or more favourable mutations are identified through screening a mutant plant population. In some embodiments, one or more favourable mutations that are identified through a screening approach can be introduced into a different plant or plant cell and the introduced mutation can be identified or selected using methods known to those of skill in the art—such as Southern blot analysis, DNA sequencing, PCR analysis, or phenotypic analysis. Mutations that impact gene expression or that interfere with the function of the encoded HMA protein can be determined using methods that are well known in the art. Any plant of interest, including a plant cell or plant material can be modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Mutant polypeptide variants can be used to create mutant plants or plant cells comprising one or more mutant polypeptide variants. The HMA activity of the mutant polypeptide variant may be higher, lower or about the same as the unmutated polypeptide. Suitably, the HMA activity of the mutant polypeptide variants is partially inactivated (for example, reduced) or lost (for example, inhibited or eliminated) as described herein.

Mutations in the nucleotide sequences and polypeptides described herein can include man-made mutations or synthetic mutations or genetically engineered mutations. Mutations in the nucleotide sequences and polypeptides described herein can be mutations that are obtained or obtainable via a process which includes an in vitro or an in vivo manipulation step. Mutations in the nucleotide sequences and polypeptides described herein can be mutations that are obtained or obtainable via a process which includes intervention by man. By way of example, the process may include mutagenesis using exogenously added chemicals—such as mutagenic, teratogenic, or carcinogenic organic compounds, for example ethyl methanesulfonate (EMS), that produce random mutations in genetic material. By way of further example, the process may include one or more genetic engineering steps—such as one or more of the genetic engineering steps that are described herein or combinations thereof. By way of further example, the process may include one or more plant crossing steps. The activity of one or more HMA polypeptides in a plant is reduced or inhibited according to the present disclosure if the HMA polypeptide activity is statistically lower than the activity of the same HMA polypeptide(s) in a plant that has not been modified to reduce or inhibit the activity of that HMA polypeptide and which has been cultured and harvested using the same protocols. The activity of a HMA polypeptide in a plant is considered to be eliminated when it is not detectable by the assay methods described herein. In order to analyse the Cd transport activity of a mutant HMA protein, a yeast-based assay can be used. In this assay, the full-length sequence can be cloned into a yeast expression vector and expressed in a Cd-sensitive ycf1 yeast mutant. Cells in the log phase are diluted to different $OD_{600}$ and spotted onto medium containing Cd. The Cd tolerance of the strain reflects the transport activity of the HMA mutant protein. As an alternative, the activity can be deduced when combining a mutated HMA sequence with a second HMA nonsense mutation which completely abolishes HMA transport activity. A nonsense mutation that truncates a large part of the protein is expected not to show any transport activity. For a missense mutation, enzyme activity can be either partially reduced or completely lost. When Cd values in a double mutant combining nonsense and missense mutations are similar to the control, it can be deduced that the missense mutation has no significant influence on protein activity. When the Cd values and/or the phenotype are between a double nonsense mutation and the control, partial activity of the missense mutation can be assumed. When Cd values and phenotype are similar to the double HMA nonsense mutant, it can be concluded that the missense mutation completely abolishes transport activity.

Methods that introduce a mutation randomly in a gene sequence can include chemical mutagenesis, EMS mutagenesis and radiation mutagenesis. Methods that introduce one or more targeted mutations into a cell include but are not limited to genome editing technology, particularly zinc finger nuclease-mediated mutagenesis (reviewed in Petolino, 2015), targeting induced local lesions in genomes (TILLING) (reviewed in Chen et al., 2014), meganuclease-mediated mutagenesis (see, for example, Arnould et al., 2011), TALENs (reviewed in Wright et al., 2014) and the CRISPR/Cas system (reviewed in Bortesi and Fischer, 2015). Methods of genome/gene editing in plants is reviewed in, for example, in Puchta and Fauser (2013), Qiwei and Caixia, (2015) and Chen and Gao (2014).

Combinations of the various methods described above are also contemplated. In other words, the activity or expression of one HMA may be modulated using one particular technique and a second HMA may be modulated using a different technique.

Some non-limiting examples of mutations are deletions, insertions, nonsense and missense mutations of at least one nucleotide, single nucleotide polymorphisms and a simple sequence repeat. After mutation, screening can be performed to identify mutations that create premature stop codons or otherwise non-functional genes. Screening of mutants can be carried out by sequencing, or by the use of one or more probes or primers specific to the gene or protein. Specific mutations in polynucleotides can also be created that can result in modulated gene expression, modulated stability of mRNA, or modulated stability of protein. Such plants are referred to herein as "non-naturally occurring" or "mutant" plants. The mutant or non-naturally occurring plants may include at least a portion of foreign or synthetic or man-made nucleic acid (for example, DNA or RNA) that was not present in the plant before it was manipulated. The foreign nucleic acid may be a single nucleotide, two or more nucleotides, two or more contiguous nucleotides or two or more non-contiguous nucleotides—such as at least 10, 20, 30, 40, 50, 100, 200, 300, 400, 500, 600, 700, 800, 900, 1000, 1100, 1200, 1300, 1400 or 1500 or more contiguous or non-contiguous nucleotides.

In one embodiment, seeds from plants are mutagenised and then grown into first generation mutant plants, which are then screened for mutations in their loci. The first generation plants can be allowed to self-pollinate and seeds from the first generation plant can be grown into second generation plants, which can be screened for mutations in their loci. Though the mutagenized plant material (including seeds) can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant nucleic acid is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

Mutagens that create primarily point mutations and short deletions, insertions, transversions, and or transitions, including chemical mutagens or radiation, may be used to create the mutations. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine dihydrochloride and formaldehyde.

Spontaneous mutations in the locus that may not have been directly caused by the mutagen are also contemplated provided that they result in the desired phenotype. Suitable mutagenic agents can also include, for example, ionising radiation—such as X-rays, gamma rays, fast neutron irradiation and UV radiation. Any method of plant nucleic acid preparation known to those of skill in the art may be used to prepare the plant nucleic acid for mutation screening. Prepared nucleic acid from individual plants, plant cells, or plant material can optionally be pooled in order to expedite screening for mutations in the population of plants originating from the mutagenized plant tissue, cells or material. One or more subsequent generations of plants, plant cells or plant material can be screened. The size of the optionally pooled group is dependent upon the sensitivity of the screening method used.

After the nucleic acid samples are optionally pooled, they can be subjected to polynucleotide-specific amplification techniques, such as Polymerase Chain Reaction. Any one or more primers or probes specific to the gene or the sequences immediately adjacent to the gene may be utilized to amplify the sequences within the optionally pooled nucleic acid sample. Examples of oligonucleotide primers are described herein. Suitably, the one or more primers or probes are designed to amplify the regions of the locus where useful mutations are most likely to arise. Most suitably, the primer is designed to detect mutations within regions of the polynucleotide. Additionally, it is suitable for the primer(s) and probe(s) to avoid known polymorphic sites in order to ease screening for point mutations. To facilitate detection of amplification products, the one or more primers or probes may be labelled using any conventional labelling method. Primer(s) or probe(s) can be designed based upon the sequences described herein using methods that are well understood in the art.

To facilitate detection of amplification products, the primer(s) or probe(s) may be labelled using any conventional labelling method. These can be designed based upon the sequences described herein using methods that are well understood in the art. Polymorphisms may be identified by means known in the art and some have been described in the literature. In a further aspect there is provided a method of preparing a mutant plant. The method involves providing at least one cell of a plant comprising a gene encoding a functional HMA polypeptide as described herein (or any combination thereof as described herein). Next, the at least one cell of the plant is treated under conditions effective to modulate the activity of the HMA polypeptide(s) described herein. The at least one mutant plant cell is then propagated into a mutant plant, where the mutant plant has a modulated level of HMA polypeptide(s) as compared to that of a control plant. In one embodiment of this method of making a mutant plant, the treating step involves subjecting the at least one cell to a chemical mutagenising agent as described above and under conditions effective to yield at least one mutant plant cell. In another embodiment of this method, the treating step involves subjecting the at least one cell to a radiation source under conditions effective to yield at least one mutant plant cell. The term "mutant plant" includes mutant plants in which the genotype is modified as compared to a control plant.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to create a mutation that is non-naturally occurring in that plant and to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the genes described herein which confer a desired trait. The mutant allele(s) that occurs naturally can be transferred to the second plant by various methods including breeding, backcrossing and introgression to produce a lines, varieties or hybrids that have one or more mutations in the genes described herein. Plants showing a desired trait may be screened out of a pool of mutant plants. Suitably, the selection is carried out utilising the knowledge of the nucleotide sequences as described herein. Consequently, it is possible to screen for a genetic trait as compared to a control. Such a screening approach may involve the application of conventional nucleic acid amplification and/or hybridization techniques as discussed herein.

In another aspect there is provided a method for preparing a mutant plant which has reduced levels of Cd as compared to a control plant comprising the steps of: (a) providing a sample from a first plant; (b) determining if said sample comprises a simultaneous mutations in each of the HMA4 polypeptides described herein that result in reduced levels of Cd in plants grown in the field; and (c) transferring both mutations into a second plant. The mutation(s) can be transferred into the second plant using various methods that are known in the art—such as by genetic engineering, genetic manipulation, introgression, plant breeding, backcrossing and the like. In one embodiment, the second plant has a different genetic background to the first plant.

In another aspect there is provided a method for preparing a mutant plant which has reduced levels of Cd as compared to a control plant comprising the steps of: (a) providing a sample from a first plant; (b) determining if said sample comprises a double mutations in the HMA4 polypeptides described herein that result in reduced levels of Cd in plants grown in the field; and (c) introgressing both mutations from the first plant into a second plant. In one embodiment, the step of introgressing comprises plant breeding, optionally including backcrossing and the like. In one embodiment, the second plant has a different genetic background to the first plant. In one embodiment, the first plant is not a cultivar or an elite cultivar. In one embodiment, the second plant is a cultivar or an elite cultivar.

A further aspect relates to a mutant plant (including a cultivar or elite cultivar mutant plant) obtained or obtainable by the methods described herein. In certain embodiments, the "mutant plant" may have one or more mutations localised only to a specific region of the plant—such as within the sequence of the one or more polynucleotide(s) described herein. According to this embodiment, the remaining genomic sequence of the mutant plant will be the same or substantially the same as the plant prior to the mutagenesis.

The present disclosure is likely reproducible in other plants and applicable for breeding with variant lines.

Plants of interest include, but are not limited to, monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species may include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (*eucalyptus*), *Triticosecale* (tritic wheat times rye), bamboo, *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), *Brassica juncea, Beta vulgaris* (sugarbeet), *Manihot esculenta* (cassava), *Lycopersicon esculentum* (tomato), *Lactuca sativa* (lettuce), *Musyclise alca* (banana), *Solanum tuberosum* (potato), *Brassica oleracea* (broccoli, cauliflower, Brussels sprouts), *Camellia sinensis* (tea), Fragaria *ananassa* (strawberry), *Theobroma cacao* (cocoa), *Coffe cliseca* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Rosa* spp. (rose), *Dianthus caryophyllus* (carnation), *Petunia* spp. (*petunia*), Poinsettia *pulcherrima* (poinsettia), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy), *Panicum virgatum* (switchgrass), Sorghu57yclise57or (sorghum, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Various embodiments are directed to mutant plants or plant cells modified to modulate gene expression levels thereby producing a plant or plant cell—such as a tobacco plant or tobacco plant cell—in which the expression level of a HMA polypeptide is modulated within tissues of interest as compared to a control. The disclosed compositions and methods can be applied to any species of the genus *Nicotiana*, including *N. rustica* and *N. tabacum* (for example, LA B21, LN KY171, TI 1406, Basma, *Galpao*, Perique, Beinhart 1000-1, and Petico). Other species include *N. acaulis, N. acuminata, N. africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis subsp. hesperis, N. otophora, N. paniculata, N. pauciflora, N. petunioides, N. plumbaginifolia, N. quadrivalvis, N. raimondii, N. repanda, N. rosulata, N. rosulata subsp. ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae*.

The use of tobacco cultivars and elite tobacco cultivars is also contemplated herein. The mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar).

Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Periqe' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B13P, Xanthi (Mitchell-Mor), Bel-W3, 79-615, Samsun Holmes NN, KTRDC number 2 Hybrid 49, Burley 21, KY8959, KY9, MD 609, PG01, PG04, P01, P02, P03, RG11, RG 8, VA509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpão Comum, HBO4P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated. In one embodiment, the Burley type of *Nicotiana tabacum* is used.

Embodiments are also directed to compositions and methods for producing mutant plants that have been modified to modulate the expression or activity of a HMA polynucleotide(s) described herein (or any combination thereof as described herein). Advantageously, the mutant plants that are obtained may be similar or substantially the same in overall appearance to control plants. Various phenotypic characteristics such as degree of maturity, number of leaves per plant, stalk height, leaf insertion angle, leaf size (width and length), internode distance, and lamina-midrib ratio can be assessed by field observations.

One aspect relates to a seed of a mutant plant. Suitably, the seed is a tobacco seed. A further aspect relates to pollen or an ovule of a mutant plant that is described herein. In addition, there is provided a mutant plant as described herein which further comprises a nucleic acid conferring male sterility.

Also provided is a tissue culture of regenerable cells of the mutant plant or a part thereof as described herein, which culture regenerates plants capable of expressing all the morphological and physiological characteristics of the parent. The regenerable cells include but are not limited to cells from leaves, pollen, embryos, cotyledons, hypocotyls, roots, root tips, anthers, flowers and a part thereof, ovules, shoots, stems, stalks, pith and capsules or callus or protoplasts derived therefrom.

A still further aspect, relates to a cured or dried plant material—such as cured or dried leaf or cured or dried tobacco—derived or derivable from a mutant plant or cell, wherein expression of one or more of the HMA polynucleotides described herein or the activity of the protein encoded thereby is reduced and which results in reduced levels of Cd therein.

Embodiments are also directed to compositions and methods for producing mutant plants or plant cells that have been modified to modulate the expression or activity of the one or more of the HMA polynucleotides or HMA polypeptides described herein which can result in plants or plant components (for example, leaves—such as cured or dried leaves) or plant cells with reduced levels of Cd as described herein.

Suitably the visual appearance of the plants described herein is substantially the same as the control plant. Suitably, the biomass and leaf size is substantially unchanged as compared to the control plant. In one embodiment, the leaf weight of the mutant plant is substantially the same as the control plant. In one embodiment, the leaf number of the mutant plant is substantially the same as the control plant. In one embodiment, the leaf weight and the leaf number of the mutant plant is substantially the same as the control plant. In one embodiment, the stalk height of the mutant plants is substantially the same as the control plants at, for example, one, two or three or more months after field transplant or 10, 20, 30 or 36 or more days after topping. For example, the stalk height of the mutant plants is not less than the stalk height of the control plants. In another embodiment, the chlorophyll content of the mutant plants is substantially the same as the control plants. In another embodiment, the stalk height of the mutant plants is substantially the same as the control plants and the chlorophyll content of the mutant plants is substantially the same as the control plants. In other embodiments, the size or form or number or colouration of the leaves of the mutant plants is substantially the same as the control plants.

A reduction in expression as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional activity or polynucleotide expression or polypeptide expression or a combination thereof.

A reduction in activity as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%.

Polynucleotides and recombinant constructs described herein can be used to modulate the expression of NtHMA4 as described herein in a plant species of interest, suitably tobacco. Polynucleotides and recombinant constructs described herein can be used to express the mutant NtHMA4 polypeptides as described herein in a plant species of interest, suitably tobacco.

In certain embodiments, the leaf phenotype and growth rate of the mutant plant or part thereof is the same as the control plant. An example of a double mutation that confers these properties is G251D/Q561*.

In certain embodiments, the leaf phenotype of the mutant plant or part thereof is the same as the control plant and the mutant plant or part thereof exhibits at an early stage delayed growth as compared to the control plant. Delayed growth at an early stage is not considered to be problematic because at harvest time, biomass differences as compared to the control plants are not observed. An example of a double mutant that confers these properties is T402I/Q561*.

In certain embodiments, the leaf phenotype of the mutant plant or part thereof is the same as the control plant except for the presence of necrotic lesions at an early stage and the mutant plant or part thereof exhibits delayed growth as compared to the control plant at an early stage. The presence of necrotic lesions is not problematic because necrotic lesions are not observed under most conditions at harvest time in the field. An example of a double mutant that confers these properties is Q293*/Q561* or Q293*/W265* or E296K/Q561* or Q464*/Q561* or Q293*/G235E. Suitably, the amount of growth of the mutant plants or part thereof as described herein is not reduced as compared to the control plant.

Suitably, the mutant plants or part thereof as described herein do not exhibit a dwarf phenotype as compared to the control plant. Suitably, the mutant plants or part thereof as described herein do not exhibit a dwarf phenotype at harvest time as compared to the control plant harvest time.

Suitably, the mutant plants or part thereof as described herein do not show a biomass (leaf weight) reduction as compared to the control. Suitably, the mutant plants or part thereof as described herein do not show a biomass (leaf weight) reduction at harvest time as compared to the control.

In certain embodiments, the mutant plants may be supplemented with zinc during growth. Various embodiments are directed to methods for reducing the expression level of one or more polynucleotides described herein by integrating multiple copies of the polynucleotide into a plant genome, comprising: transforming a plant cell host with an expression vector that comprises a promoter operably-linked to one or more polynucleotides described herein. The polypeptide encoded by a recombinant polynucleotide can be a native polypeptide, or can be heterologous to the cell.

A plant carrying a mutant allele of one or more polynucleotides described herein (or any combination thereof as described herein) can be used in a plant breeding program to create useful lines, varieties and hybrids. In particular, the mutant allele is introgressed into the commercially important varieties described above. Thus, methods for breeding plants are provided, that comprise crossing a mutant plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars.

Intraspecific as well as interspecific matings are contemplated. The progeny plants that arise from such crosses, also referred to as breeding lines, are examples of non-naturally occurring plants of the disclosure.

In one embodiment, a method is provided for producing a non-naturally occurring or mutant plant comprising: (a) crossing the mutant plant with a second plant to yield progeny tobacco seed; (b) growing the progeny seed, under plant growth conditions, to yield the non-naturally occurring plant. The method may further comprise: (c) crossing the previous generation of non-naturally occurring plant with itself or another plant to yield progeny seed; (d) growing the progeny seed of step (c) under plant growth conditions, to yield additional non-naturally occurring plants; and (e) repeating the crossing and growing steps of (c) and (d) multiple times to generate further generations of non-naturally occurring plants. The method may optionally comprises prior to step (a), a step of providing a parent plant which comprises a genetic identity that is characterized and that is not identical to the mutant plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly plant breeding, are well known and can be used in the methods of the disclosure. The disclosure further provides non-naturally occurring plants produced by these methods. Certain embodiments exclude the step of selecting a plant.

In some embodiments of the methods described herein, lines resulting from breeding and screening for variant genes are evaluated in the field using standard field procedures. Control genotypes including the original unmutagenized parent are included and entries are arranged in the field in a randomized complete block design or other appropriate field design. For tobacco, standard agronomic practices are used, for example, the tobacco is harvested, weighed, and sampled for chemical and other common testing before and during curing or drying. Statistical analyses of the data are performed to confirm the similarity of the selected lines to the parental line. Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed mutant alleles of a gene into other plants, as described herein. For example, a breeder can create segregating populations from hybridizations of a genotype containing a mutant allele with an agronomically desirable genotype. Plants in the F2 or backcross generations can be screened using a marker developed from a genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

In a breeding program, successful crosses yield F1 plants that are fertile. Selected F1 plants can be crossed with one of the parents, and the first backcross generation plants are self-pollinated to produce a population that is again screened for variant gene expression (for example, the null version of the gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant gene expression. In some embodiments, a plant population in the F2 generation is screened for variant gene expression, for example, a plant is identified that fails to express a polypeptide due to the absence of the gene according to standard methods, for example, by using a PCR method with primers based upon the nucleotide sequence information for the polynucleotide(s) described herein (or any combination thereof as described herein). Hybrid varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant plants can be screened or selected for those members of the population that have a desired trait or phenotype. For example, a population of progeny of a single transformation event can be screened for those plants having a desired level of expression or activity of the polypeptide(s) encoded thereby. Physical and biochemical methods can be used to identify expression or activity levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining and enzyme assays also can be used to detect the presence or expression or activity of polypeptides or polynucleotides.

Mutant plant cells and plants are described herein comprising one or more recombinant polynucleotides, one or more polynucleotide constructs, one or more double-stranded RNAs, one or more conjugates or one or more vectors/expression vectors.

Without limitation, the mutant plants described herein may be modified for other purposes either before or after the expression or activity has been modulated according to the present disclosure. Suitably, the mutant plants remain as non-GMO plants despite these further modifications. One or more of the following genetic modifications can be present in the mutant plants. In one embodiment, one or more genes that are involved in the conversion of nitrogenous metabolic intermediates is modified resulting in plants (such as leaves)

that when cured, produces lower levels of at least one tobacco-specific nitrosamine than control plants. Non-limiting examples of genes that can be modified include, as described herein, genes encoding an asparagine synthetase, such as CYP82E4, CYP82E5 and CYP82E10 which participate in the conversion of nicotine to nornicotine and are described in WO2006091194, WO2008070274, WO2009064771 and PCT/US2011/021088 and as described herein. In another embodiment, one or more genes that are involved in heavy metal uptake or heavy metal transport are modified resulting in plants or parts of plants (such as leaves) having a lower heavy metal content than control plants or parts thereof without the modification(s). Non-limiting examples include genes in the family of multidrug resistance associated proteins, the family of cation diffusion facilitators (CDF), the family of Zrt-, Ift-like proteins (ZIP), the family of cation exchangers (CAX), the family of copper transporters (COPT), the family of heavy-metal P-type ATPases (for example, HMAs, as described in WO2009074325), the family of homologs of natural resistance-associated macrophage proteins (NRAMP), and the family of ATP-binding cassette (ABC) transporters (for example, MRPs, as described in WO2012/028309, which participate in transport of heavy metals, such as Cd. The term heavy metal as used herein includes transition metals. Examples of other modifications include herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. QB protein of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*. Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single protein and significantly delayed the evolution of resistant insects. Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered. Another exemplary modification results in altered reproductive capability, such as male sterility. Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance. Other exemplary modifications can result in plants with improved storage proteins and oils, plants with enhanced photosynthetic efficiency, plants with prolonged shelf life, plants with enhanced carbohydrate content, and plants resistant to fungi; plants encoding an enzyme involved in the biosynthesis of alkaloids. Transgenic plants in which the expression of S-adenosyl-L-methionine (SAM) and/or cystathionine gamma-synthase (CGS) has been modulated are also contemplated.

One or more such traits may be introgressed into the mutant plants from another cultivar or may be directly transformed into it. The introgression of the trait(s) into the mutant plants may be achieved by any method of plant breeding known in the art, for example, pedigree breeding, backcrossing, doubled-haploid breeding, and the like (see, Wernsman, E. A, and Rufty, R. C. 1987. Chapter Seventeen. Tobacco. Pages 669-698 In: Cultivar Development. Crop Species. W. H. Fehr (ed.), MacMillan Publishing Co, Inc., New York, N.Y. 761 pp.). Molecular biology-based techniques described above, in particular RFLP and microsatellite markers, can be used in such backcrosses to identify the progenies having the highest degree of genetic identity with the recurrent parent. This permits one to accelerate the production of varieties having at least 90%, suitably at least 95%, more suitably at least 99% genetic identity with the recurrent parent, yet more suitably genetically identical to the recurrent parent, and further comprising the trait(s) introgressed from the donor parent. Such determination of genetic identity can be based on molecular markers known in the art.

The last backcross generation can be selfed to give pure breeding progeny for the nucleic acid(s) being transferred. The resulting plants generally have essentially all of the morphological and physiological characteristics of the mutant plants, in addition to the transferred trait(s) (for example, one or more single gene traits). The exact backcrossing protocol will depend on the trait being altered to determine an appropriate testing protocol. Although backcrossing methods are simplified when the trait being transferred is a dominant allele, a recessive allele may also be transferred. In this instance, it may be necessary to introduce a test of the progeny to determine if the desired trait has been successfully transferred.

Various embodiments provide mutant plants as well as biomass in which the expression level of NtHMA4 polynucleotides is reduced to reduce the Cd content therein.

Parts of such plants, particularly tobacco plants, and more particularly the leaf lamina and midrib of tobacco plants, can be incorporated into or used in making various consumable products including but not limited to aerosol forming materials, aerosol forming devices, smoking articles, smokable articles, smokeless products, and tobacco products. Examples of aerosol forming materials include but are not limited to tobacco compositions, tobaccos, tobacco extract, cut tobacco, cut filler, cured or dried tobacco, expanded tobacco, homogenized tobacco, reconstituted tobacco, and pipe tobaccos. Smoking articles and smokable articles are types of aerosol forming devices. Examples of smoking articles or smokable articles include but are not limited to cigarettes, cigarillos, and cigars. Examples of smokeless products comprise chewing tobaccos, and snuffs. In certain aerosol forming devices, rather than combustion (or burning), a tobacco composition or another aerosol forming material is heated, for example, by one or more electrical heating elements, to produce an aerosol. Typically in such heated smoking articles, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user. Such devices include, for example, electrically heated aerosol-generating devices in which an aerosol is generated by the transfer of heat from one or more electrical heating elements of the aerosol-generating device to the aerosol-forming substrate of a heated smoking article.

In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as cigarettes, or by combusting an aerosol forming material.

In one embodiment, there is also provided cured plant material from the mutant tobacco plants described herein. Processes of curing green tobacco leaves are known by those having ordinary skill in the art and include without limitation air-curing, fire-curing, flue-curing and sun-curing. The process of curing green tobacco leaves depends on the type of tobacco harvested. For example, Burley and certain dark strains are usually air-cured, and pipe tobacco, chewing tobacco, and snuff are usually fire-cured.

Smokeless tobacco products incorporating tobacco plants as described herein can be manufactured in any format suitable for comfort in a consumer's oral cavity. Smokeless tobacco products contain tobacco in any form, including as dried particles, shreds, granules, powders, or a slurry deposited on, mixed in, surrounded by, or otherwise combined with other ingredients in any format, such as flakes, films, tabs, foams, or beads. Smokeless tobacco products may be wrapped with a material, which may be edible or nonedible. Liquid contents of smokeless tobacco products can be enclosed in a form, such as beads, to preclude interaction with a water-soluble wrapper. The wrapper may be shaped as a pouch to partially or completely enclose tobacco-incorporating compositions, or to function as an adhesive to hold together a plurality of tabs, beads, or flakes of tobacco. A wrapper may also enclose a mouldable tobacco composition that conforms to the shape of a consumer's mouth. An orally disintegrable wrapper may enclose smokeless tobacco, for example, as dry snuff or soluble tobacco, and may be formed on continuous thermoforming or horizontal form/fill/seal equipment or other suitable packaging equipment using edible films (which may or may not contain tobacco). Exemplary materials for constructing a wrapper include film compositions comprising HPMC, CMC, pectin, alginates, pullulan, and other commercially viable, edible film-forming polymers. Wrappers that are not orally disintegrable may be composed of woven or nonwoven fabrics, of coated or uncoated paper, or of perforated or otherwise porous plastic films. Wrappers may incorporate flavouring and/or colouring agents. Smokeless products can be assembled together with a wrapper utilizing any method known to persons skilled in the art of commercial packaging, including methods such as blister packing and stick-packing, in which a small package can be formed by a vertical form/fill/seal packaging machine.

In another embodiment, there is also provided dried plant material from the mutant plants described herein. Processes of drying leaves are known by those having ordinary skill in the art and include without limitation air-drying and sun-drying. The exact process of drying leaves depends on the type of plant that is harvested. Suitably, the plant material is dried after harvesting. Thus, the use of dried material and post-harvested dried material is contemplated herein. The drying process may activate one or more senescence associated genes. The expression of activity of the genes and proteins described herein can be monitored during curing or drying.

In another embodiment, there is described tobacco products including tobacco-containing aerosol forming materials comprising plant material—such as leaves, suitably cured or dried leaves—from the mutant tobacco plants described herein. The tobacco products described herein can be a blended tobacco product which may further comprise unmodified tobacco. The amount of Cd in the field grown plant, part of the plant, plant material, plant product or tobacco product described herein can be reduced by at least about 33%, 35%, 40%, 45%, 50%, 55%, 60%, 65%, 70%, 75%, 80%, 85%, 90%, 91%, 92%, 93%, 94% or 95% or more, when compared to the wild-type counterpart. As HMA4 acts in root-to-shoot Cd translocation, reducing or eliminating the activity or expression of HMA4 can lead to reduced Cd accumulation in leaves and increased Cd accumulation in roots.

In certain embodiments, it may be desirable to grow the plants described herein in the presence of fertilisers. In one embodiment, the fertiliser may comprise or consist of Zn which is added to the field either before or during the time that the plants are grown. This supplementation may help to replenish or restore the Zn content in the plant whilst still have reduced levels of Cd. This supplementation may help to restore the phenotype of the plant whilst still having reduced levels of Cd. Zn addition may increase stalk height and/or leaf weight.

Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the package that describes the nature of the seeds therein.

Compositions, methods and kits for genotyping plants for identification, selection, or breeding can comprise a means of detecting the presence of a polynucleotide (or any combination thereof as described herein) in a sample of polynucleotide. Accordingly, a composition is described comprising one of more primers for specifically amplifying at least a portion of one or more of the polynucleotides and optionally one or more probes and optionally one or more reagents for conducting the amplification or detection.

In one embodiment, there is also provided cured or dried plant material from the mutant plants described herein. For example, processes of curing or drying tobacco leaves are known by those having skills in the field and include without limitation air-curing, fire-curing, flue-curing and sun-curing. The process of curing green tobacco leaves depends on the type of tobacco harvested as described herein.

In another embodiment, there is described tobacco products including tobacco products comprising plant material— such as leaves, suitably cured plant material—such as cured or dried leaves—from the mutant plants described herein or which are produced by the methods described herein. The tobacco products described herein may further comprise unmodified tobacco.

In another embodiment, there is described tobacco products comprising plant material, suitably leaves—such as cured or dried leaves, from the mutant plants described herein. For example, the plant material may be added to the inside or outside of the tobacco product and so upon burning a desirable aroma is released. The tobacco product according to this embodiment may even be an unmodified tobacco or a modified tobacco. The tobacco product according to this embodiment may even be derived from a mutant plant which has mutations in one or more genes other than the genes disclosed herein.

The invention is further described in the Examples below, which are provided to describe the invention in further detail. These examples, which set forth a preferred mode presently contemplated for carrying out the invention, are intended to illustrate and not to limit the invention.

EXAMPLES

Example 1—Materials & Methods

HMA4 Sequences

NtHMA4.1 (protein sequence: SEQ ID NO:1, Genbank: CCQ77798.1; nucleotide sequence: SEQ ID NO:3, Genbank: HF675181.1) and NtHMA4.2 (protein sequence: SEQ ID NO:2, Genbank: CCW03243.1; nucleotide sequence: SEQ ID NO:4, Genbank: HF937054.1)

Plant Material

TN90 (PI 543792, TC 586, USDA-GRIN database), K326 (PI 552505, TC 319, USDA-GRIN database). AA37 is presumably a cross between a South American dark tobacco and American Burley germplasm.

Generation of HMA4 RNAi Plants

For construction of an HMA4 RNAi construct, a sequence of exon 7 of HMA4.1 (5'-TGAGAGCAAGTCAGGT-CATCCGATGGCAGCCGCTCTGGTGGAC-TATGCACAATCAAAT TCCGTTGAGCCAAAGCCTGA-TAGAGTTGAGCAGTTTCAAAATTTTCCTGGTGAAGG-GAT ATTTGGAAGAATTGATGGAATGGAAATC-TATGTCGGGAATAGGAAAATTTCTTCAAGAG CTG-GATGTACCACAG-3') (SEQ ID NO:5) is used in sense and antisense direction and part of the adjacent intron (5'-TAAATGGTTGAATCATTTCTTATGCTCAT-AGTAGAGATAAAACATCAGA GTTATAAT-TATAAGTATATGATTTCTCCAGTTAATTTTGCTGTTAGAT-TTTCTTTGACCTGT TTAGCACTAATGCGGTGGATGTTTGAAT-3') (SEQ ID NO:6) is employed as hairpin loop. The construct is designed with Gateway sites and synthesized by Geneart (Invitrogen, Life technologies, Regensburg, Germany). Then it is transferred into an expression vector using the Gateway technology and corresponding enzymes (Invitrogen, Life technologies, Carlsbad, Calif., USA). *Agrobacterium tumefaciens* is transformed with the expression vector and is used for tobacco leaf disc transformation using previously described methods (Horsch et al., 1985). T0 primary transformants are grown on soil and their roots analysed for HMA4 expression. Best performing lines (lowest HMA4 expression) are identified and the T1 generation and wild type plants are grown on agar medium and total roots are again analysed for HMA4 expression.

EMS Mutant Lines and TILLING

A mutant population is created by treating tobacco AA37 seeds with the mutagenic agent ethyl methanesulfonate (EMS). A DNA library of about 9'800 M2 generation EMS-treated plants (representing the segregating progeny of 1050 M1 generation variants) is screened for mutations in the two HMA4 genes. Five amplicons were sequenced and analysed for mutations in HMA4.1 and in HMA4.2, respectively. The following primer pairs are used for amplification: HMA4.1-Exon1: forward primer 5'-GCATGTTCT-TATAAGAGAAACTC-3' (SEQ ID NO:7), reverse primer 5'-GTGAATTTATTTAACAAGCCACA-3'(SEQ ID NO:8); HMA4.1-Exon2: forward primer 5'-CCAAAAT-TGTTTCTGCTTCTCC-3'(SEQ ID NO.9), reverse primer 5'-CGTCATATAAATTGGGACAAAAG-3 (SEQ. ID NO:10)'; HMA4.1-Exon4/5: forward primer 5'-GTGTCTT-TATTTTCTCACTGATA-3 (SEQ ID NO:11)', reverse primer 5'-TAGTGACGTGATTCATAAGACAA-3 (SEQ ID NO:12)'; HMA4.1-Exon6: forward primer 5'-ATCAGTCCTTTCACTTGACCC-3 (SEQ ID NO:13)', reverse primer 5'-AACCATTAGAGCCATTTCAGAA-3' (SEQ ID NO:14); HMA4.1-Exon7/8: forward primer 5'-GATACTGCAATACAAAAGCACAT-3 (SEQ ID NO:15)', reverse primer 5'-CACT-TACTTGGTAATACGTTCT-3 (SEQ ID NO:16)'; HMA4.2-Exon1: forward primer 5'-TTGCTACTCTGGGTTGC-TAC-3 (SEQ ID NO:17)', reverse primer 5'-TCAAGTTTAAAGTTTGCTTCTAC-3 (SEQ ID NO: 18)'; HMA4.2-Exon2: forward primer 5'-TGTGCATACAT-AACGTAAATCG-3 (SEQ ID NO:19)', reverse primer 5'-ATCAAATACCACATAAGTAGGG-3 (SEQ ID NO:20)'; HMA4.2-Exon4/5: forward primer 5'-TTTAGT-CACTTTGACATAAATGG-3' (SEQ ID NO:21), reverse primer 5'-AAGACAGAGAACAAGTTCACAT-3 (SEQ ID NO:22)'; HMA4.2-Exon6: forward primer 5'-TCAGTCCTTTCGCTTGACCT-3 (SEQ ID NO:23)', reverse primer 5'-GAGAATGTGGTACTCGCAAG-3 (SEQ ID NO:24)'; HMA4.2-Exon7/8: forward primer 5'-ATACAT-TGAGGACACATAATCG-3 (SEQ ID NO:25)', reverse primer 5'-TATACCCCATTCTGACCCTTG-3 (SEQ ID NO:26)'. The amplification products are sequenced according to the Sanger method on ABI XL3730 (Applied Biosystems, Life Technologies, Foster City, Calif., USA). The amplification primers are likewise used for sequencing, except for HMA4.2-Exon6, where a nested reverse primer 5'-TTATGAATATATGCTACAAATCAC-3' is used for sequencing. In order to select mutant lines with impact on protein function, stop mutations as well as missense mutations are chosen.

Greenhouse Conditions for Plant Cultivation.

The following solutions are used for fertilization, all solutions are purchased from Yara Benelux B.V. (Vlaardingen, The Netherlands): "Flue cured": macroelements: 666.5 mg NO3-l-1, 18 mg NH4+ l-1 (total of 165.39 mg N l-1), 88.78 mg P2O5 l-1, 306.25 mg K2O l-1, 49.99 mg Mg l-1, 185.61 mg Ca l-1, 369.60 mg SO42-l-1; microelements: 0.839 mg Fe l-1, 0.549 mg Mn l-1, 0.262 mg Zn l-1, 0.216 mg B l-1, 0.048 mg Cu l-1, 0.048 mg Mo l-1. "Burley": macroelements: 850.3 mg NO3-l-1, 18.5 mg NH4+ l-1 (total of 207.35 mg N l-1), 91.31 mg P2O5 l-1, 383.65 mg K2O l-1, 49.99 mg Mg l-1, 185.61 mg Ca l-1, 369.60 mg SO42-l-1; microelements: 0.839 mg Fe l-1, 0.549 mg Mn l-1, 0.327 mg Zn l-1, 0.324 mg Bl-1, 0.048 mg Cu l-1, 0.048 mg Mo l-1. HMA4 RNAi lines are fertilized in two parallel experiments with either "Flue Cured" or "Burley" solution. The varying nitrate content in the solutions does not have a differential effect on Cd levels or HMA4 phenotype. (Data presented in this study are from plants fertilized with "Flue Cured" solution".) AA37 lines are fertilized with the "Burley" solution. For Zn addition, 0.1 g of Zn in the form of ZnSO4.H2O (Landor, Birsfelden, Switzerland) is applied, diluted in 100 ml H2O. All plants are grown in 10 L pots, in a 16 h:8 h light:dark cycle.

Field Trials

The field trial is carried out in a field in Switzerland (Vaud). All plants are sown in floating trays (according to agricultural practices) and grown in a greenhouse prior to transplanting. Plants are grouped into genotypic classes. Plants are grouped into experimental units which are repeated six times in the field. In the first year, for each mutation combination, 10 plants carrying both mutations in a homozygous state are grown adjacent with 10 plants homozygous only for the mutation in HMA4.1, 10 plants homozygous only for the mutation in HMA4.2 and 10 plants that are null-segregant plants for both HMA4 genes. For the double nonsense mutants, also two other genotypes are included (in three replicates): 10 plants that are homozygous nonsense mutants for HMA4.1 and heterozygous nonsense mutants for HMA4.2 and 10 plants that are homozygous nonsense mutants for HMA4.2 and heterozygous nonsense mutants for HMA4.1, these latter groups only containing one functional non-mutant allele. In the second year, for each mutation combination, 20 plants carrying both mutations in a homozygous state are grown adjacent with 20 plants that are null-segregant plants for both HMA4 genes. The field is fertilized according to standard practices for Burley cultivation. Two field trials are carried out in one year in two fields in two tobacco growing regions containing high cadmium. For each mutation combination, 20 plants carrying both mutations in a homozygous state are grown adjacent with 20 plants that were null-segregant plants for both HMA4 genes.

Expression Analysis Using qPCR

Total RNA is extracted from tobacco using the RNeasy Plant Mini Kit (Qiagen, Hilden, Germany). The RNA is digested using RQ1 RNase-free DNase (Promega, Madison, Wis., USA) and reverse transcribed using an oligo dT17 primer, dTNPs, RNasin Plus RNase Inhibitor and M-MLV Reverse Transcriptase, RNase (H-), Point Mutant (all from Promega, Madison, Wis., USA). qRT-PCR is performed on the Mx3005P system (Stratagene, Agilent, Waldbronn, Germany). Amplification reactions are carried out with the HMA4.1 forward primer (5'-TCATGCAGAAATAAGAAGTGCCAG-3') (SEQ ID NO:27) an the HMA4.1 reverse primer (5'-ATGGATGCT-TAGAGAGTCCAGGA-3') (SEQ ID NO:28) or with the HMA4.2 forward primer (5'-GTTATGCG-GAAATAAGAAGTGCCTA-3') (SEQ ID NO:29) and the HMA4.2 reverse primer (5'-CATGGATGCT-TAGAGAGTCCAGAC-3') (SEQ ID NO:30) using SYBR 2-step QRT Low Rox (Thermo Scientific, Surrey, UK). As an internal standard, the actin9 gene is used with forward primer (5'-CTATTCTCCGCTTTGGACTTGGCA-3') (SEQ ID NO:31) and reverse primer (5'-AGGACCTCAGGACAACGGAAACG-3') (SEQ ID NO:32).

DNA Extraction and Plant Genotyping

Leaf samples are extracted using the BioSprint 96 (Qiagen, Hilden, Germany) together with the BioSprint 96 DNA plant kit (Qiagen, Hilden, Germany). DNA samples are used in a TaqMan reaction in order to determine the plant genotype. Taqman is carried out using the ABI PRISM 7900HT Sequence Detection System (Applied Biosystems, Life Technologies, Foster City, Calif., USA) and TaqMan Fast Advanced Master Mix (Applied Biosystems, Foster City, Calif., USA). The following Taqman primers (Microsynth, Balgach, Switzerland) and probes (Applied Biosystems, Life Technologies, Warrington, UK) are employed: HMA4.1 Q293*: mutant-probe 5'-AGGATGGCATAGCT-3' (SEQ ID NO:33), Wild-type (WT) probe 5'-AG-GATGGCACAGCT-3' (SEQ ID NO:34), forward primer 5' CTGGCACTACAAATCTAAATGGTAGTATAGTATTT-3' SEQ ID NO:35), reverse primer 5'-CTGGTGTATAATATT-TAGCACACTTGTCG-3' (SEQ ID NO:36); HMA4.1 E296K: mutant-probe 5'-CACAGCTTGTCAAAG-3' (SEQ ID NO:37), WT probe 5'-CACAGCTTGTCGAAG-3' (SEQ ID NO:38), forward primer 5'-CTGGCACTA-CAAATCTAAATGGTAGTATAGTATTT-3' (SEQ ID NO:39), reverse primer 5'-CTGGTGTATAATATT-TAGCACACTTGTCG-3' (SEQ ID NO:40); HMA4.1 T402I: mutant-probe 5'-TTTGACAAAACAGGGATTA-3' (SEQ ID NO:41), WT probe 5'-TTTGACAAAACAGGGACTA-3' (SEQ ID NO:42), forward primer 5'-CCATGTGTTGCGCACTTTCA-3' (SEQ ID NO:43), reverse primer 5'-AACTCGGTCACCATAAAT-TCTCCTT-3' (SEQ ID NO:44); HMA4.1 G251D: mutant-probe 5'-AGAAAACACTGACAGACG-3' (SEQ. ID NO:45), WT probe 5'-AAAACACTGACAGGCG-3' (SEQ. ID NO:46), forward primer 5'-AAGTCGTAAATGTTGAT-GAAGTCAAGG-3' (SEQ. ID NO:47), reverse primer 5'-CAGCCCAGACCGTTGAATCTC3' SEQ. ID NO:48); HMA4.1 V351M: mutant-probe 5'-CTTTGGTCACATT-GATGA-3' (SEQ ID NO:49), WT probe 5'-TTGGTCACAT-TGGTGAGT-3' (SEQ ID NO:50), forward primer 5'-GGC-TATATCAGCTTCTTTGGCAATT-3' (SEQ ID NO:51), reverse primer 5'-AACACATGGCAACTGGTGTAGA-TAGA-3' (SEQ ID NO:52); HMA4.1 G382R: mutant-probe 5'-TTCTGTTTAAAAGAGCAGAG-3' (SEQ ID NO:53), WT probe 5'-TCTGTTTAAAGGAGCAGAGTA-3' (SEQ ID NO:54), forward primer 5'-CCATGTGTTGCGCACTTTCA-3' (SEQ ID NO:55), reverse primer 5'-AACTCGGTCACCATAAATTCTCCTT-3' (SEQ ID NO:56); HMA4.2 W265*: mutant-probe 5'-ATAGATTCAACGGTCTAGG-3' (SEQ ID NO:57), WT probe 5'-TTCAACGGTCTGGGC-3' (SEQ ID NO:58), forward primer 5'-GGTGAAACTATACCTATTGATG-GAGTTGTAA-3' (SEQ ID NO:59), reverse primer 5'-CACTAAATAAATGAAGCATGAAGGAATACTAC-3' (SEQ ID NO:60); HMA4.2 Q561*: mutant-probe 5'-CAAC-CATGTGTAGGAT-3' (SEQ ID NO:61), WT probe 5'-TGC-CAACCATGTGCAG-3' (SEQ ID NO:62), forward primer 5'-TTGGTGTAAAAGAAGCAATGAGAGAG-3' (SEQ ID NO:63), reverse primer 5'-ATCATTTCAGCGTAT-TGCAGAATTT-3' (SEQ ID NO:64).

Analysis of Elemental Composition

At harvest time, mid-lower stalk positions of mature plants are harvested in pooled samples for each field plot (1 leaf per plant). From individual greenhouse plants, two mid-lower stalk position leaves (same leaf position for all plants) are harvested. The harvested material is dried in the oven at 60° C. until completely dry.

The sample analysis is carried out by ALS (Prague, Czech Republic). Samples are homogenized and mineralized by acids and hydrogen peroxide prior to analysis. Zn and Cd are measured by mass spectrometry with inductively coupled plasma (ICP-MS) according to CZ_SOP_D06_02_002 (US EPA 200.8, CSN EN ISO 17294-2).

Bioinformatics Analysis

Mutation tolerance scores are derived using the SIFT software (Ng and Henikoff, 2003), based on a database of plant sequences from UniProt (downloaded Dec. 30, 2012). RNA-seq libraries are made using the Illumina TruSeq RNA Sample prep kit and sequenced on an Illumina HiSeq-2500. Base calling and sample demultiplexing are performed using Illumina HiSeq Control Software and CASAVA pipeline software. The reads are mapped to the previously published genome (Sierro et al., 2014) using the Tophat2 software (Kim et al. 2013; version 2.0.11). Differential gene expression is calculated using Cuffdiff (Trapnell et al, 2013, version 2.2.1).

Statistics

When the analytical value is below LOQ, the LOQ value are considered for calculation and graphical representation. For evaluation of significance, 2-sided T-tests are performed, using the Satterthwaite correction for the heterogeneity of variance. For the field experiments, paired t-tests on ratios were conducted for the mutant plots and their corresponding control plots. Raw p-values were calculated for the probability that it is by chance that mean (mutant)<0.8 * mean (control), in order to determine a significant Cd/Zn reduction below the measuring uncertainty (20%).

Example 2—Identification of Orthologs of the *A. thaliana* HMA2/3/4 Transporters and NtHMA4 Expression Analysis The *Arabidopsis* transporters HMA2, HMA3 and HMA4 are closely related. While HMA2 and HMA4 are involved in Zn and Cd root-to-shoot translocation (Wong and Cobbett, 2009), HMA3 is in Cd accumulation by root vacuolar storage of Zn, Cd, Co and Pb (Gravot et al., 2004; Morel et al., 2009). Based on *Arabidopsis* sequences, the tobacco genome is screened for putative AtHMA2/3/4 orthologs and two homologs of HMA4, HMA4.1 and HMA4.2, inherited from *N. sylvestris* and *N. tomentosiformis* respectively, are found in *N. tabacum*. The expression pattern of HMA4.1 and HMA4.2 is investigated in the two main tobacco cultivars, TN90 and K326. Flue cured tobacco types (K326) require fertilization less rich in nitrogen compared to Burley type (TN90) tobacco (Lewis et al., 2012). These differences in fertilization practices also partially explain why Cd content was found to be higher in Burley type tobacco compared to flue cured tobacco (Lugon-Moulin et al., 2006). The expression pattern of NtHMA4.1 and NtHMA4.2 is analysed in different tissues of TN90 and K326 tobacco plants, grown in the field. In these two cultivars, both genes are found to be especially expressed in root and flower tissues, but also to a smaller extent in all other tissues (FIG. 1). This pattern is in accordance with GUS-expression data reported by Hussain et al. (2004) for *Arabidopsis* and by Hermand et al. (2014) for tobacco.

Example 3—Effect of NtHMA4 Silencing on Leaf Cd Accumulation and Phenotype

Figure 2:
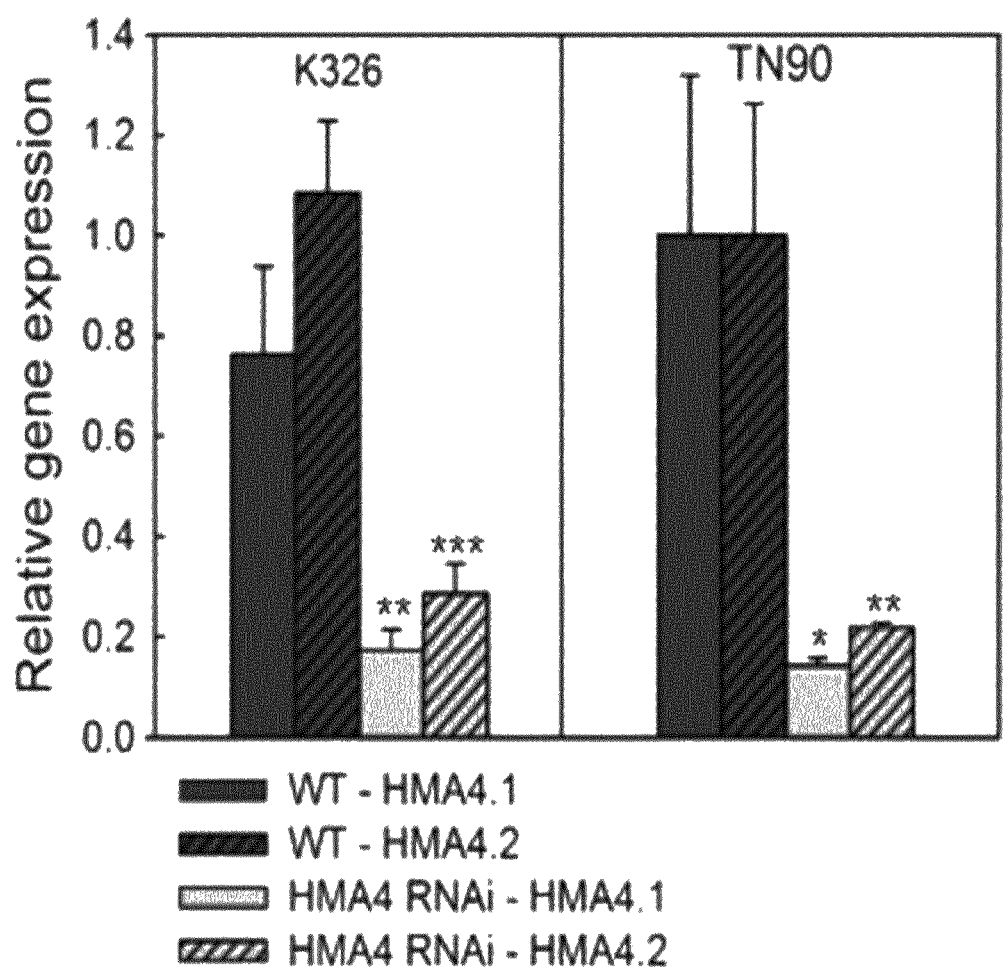
FIG. 2: Gene expression levels of HMA4.1 and HMA4.2 in TN90 and K326 HMA4 RNAi lines and their respective WT controls. Entire roots are harvested from agar grown plants, ground and extracted. Bars and errors represent mean and standard deviation (SD) of 4 replicate plants. *, , and * indicate levels of significance at $P<0.05$, $P<0.01$ and $P<0.001$, respectively, compared to the WT control plants.

To evaluate the potential of NtHMA4 tobacco genes as targets for reducing Cd, RNAi constructs are designed against both NtHMA4 homologs. DNA fragments are cloned into binary vectors under the control of the constitutive MMV promoter (Dey and Maiti, 1999) and transformed in the two above-mentioned cultivars TN90 and K326. For each tobacco type, an RNAi line is selected, based on the reduced expression of both HMA4 homeologs (FIG. 2). Five plants per line and their respective untransformed controls are grown on soil, with and without Zn supplementation.

Figure 3:
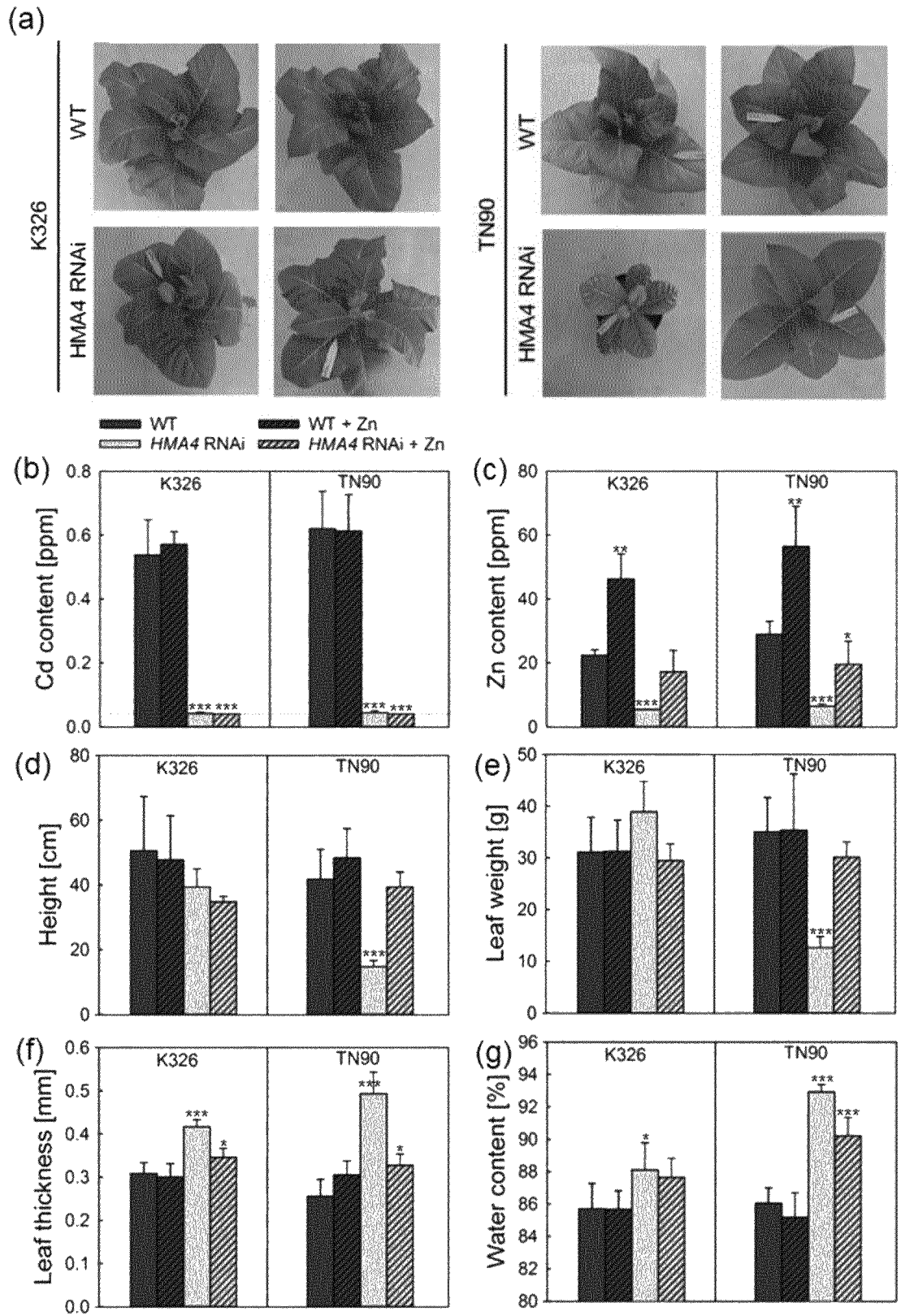
FIG. 3: (a) HMA4 RNAi K326 and TN90 tobacco plants and their respective background WT plants are grown for five weeks under low N fertilization regime in the greenhouse. (b, c) Cd/Zn levels in dry weight, (d) height, (e) leaf weight, (f) leaf thickness and (g) water content (comparison between fresh and dry weight) are determined. Bars and errors represent mean±SD of five plants. *, , and * indicate levels of significance at $P<0.05$, $P<0.01$ and $P<0.001$, respectively, compared to the untreated control plants. The dotted lines indicate LOQ=0.05 ppm for Cd measurement.

Representative plants of each line are depicted in FIG. 3a. Their respective content in Cd and Zn is shown in FIGS. 3b and c. Both TN90 and K326 HMA4 RNAi lines are very low in Cd (around LOQ=0.05 ppm) compared to control plants (>0.55 ppm Cd) in both cultivars. Besides this more than 10-fold reduction in Cd, an around 4-fold Zn reduction observed. With respect to the plant biomass (stalk height and leaf weight) the K326 HMA4 RNAi line performs very well and is not significantly smaller, with even slightly heavier leaves than the control plants (FIG. 3d, e). Leaf shape differ only slightly, transgenic leaves being rounder with thicker veins (FIG. 3a). By contrast, TN90 HMA4 RNAi lines displays stunted growth and necrotic patches on the leaves (FIG. 3a, d). Leaves are thicker compared to the TN90 WT control (FIG. 3f). Based on fresh and dry weight measurements, these plants exhibits increased water content (FIG. 3g). The experiment is repeated under high nitrate fertilization, however nitrogen supply does not affect Cd levels and phenotype (data not shown). In conclusion, these results demonstrate that silencing both HMA4 homeologs in both tobacco cultivars reduces leaf Cd more than 10-fold and Zn around 4-fold. However, despite similar Cd/Zn reduction in both varieties, phenotypic effects were very different between K326 and TN90 with K326 performing better.

Interestingly, it is observed that treating HMA4 RNAi plants with Zn replenished plant Zn content to almost control levels and restored the normal (Burley) plant phenotype in TN90 whilst still keeping reduced Cd levels (FIG. 3a-c, hatched bars). Zn addition increases stalk height and leaf weight in the TN90 RNAi line and decreases water content and leaf thickness in both TN90 and K326 HMA4 RNAi plants (FIG. 3d-g, hatched bars). This shows that Zn can complement HMA4 RNAi and restore the WT phenotype, keeping more than 90% reduced Cd content.

Example 4—Cd Reduction in the Field Requires Combination of NtHMA4 Mutations

For tobacco breeding, an EMS population of the cultivar AA37 is screened for mutations in HMA4. AA37 is a cultivar derived from a crossing between a South American dark tobacco and American Burley germplasm, it is therefore more closely related to TN90 than to K326 (Fricano et al., 2012). Comparable expression profiles suggest that both HMA4 homeologs (FIG. 1 and FIG. 2) are involved in Zn and Cd translocation from root to shoot. Therefore, exons coding for catalytically important domains are screened for point mutations in both HMA4 copies. All amino acid substitutions identified in NtHMA4.1 and NtHMA4.2 are analysed for possible impact on protein function using the SIFT program (Ng and Henikoff, 2003). A small SIFT score (<0.05) implies that an amino acid residue is likely not tolerated at the functional level. In NtHMA4.1 and in NtHMA4.2 36 and 33 mutations are identified, respectively, including 2 nonsense mutations in each of the homeologs and 15 missense mutations in each homeolog with a SIFT score ratio below 0.05 (Table 10). The SIFT score is used as a tool to facilitate the selection of mutations.

Mutations in both HMA4 isoforms are combined by crossings. Such crossings include at least one nonsense mutation and a second mutation which was either a nonsense mutation or a SIFT predicted missense mutation. Before each greenhouse and field test, the segregating offspring are grown in floating trays, genotyped using Taqman and grouped into individual classes prior to soil transplantation.

Figure 4:
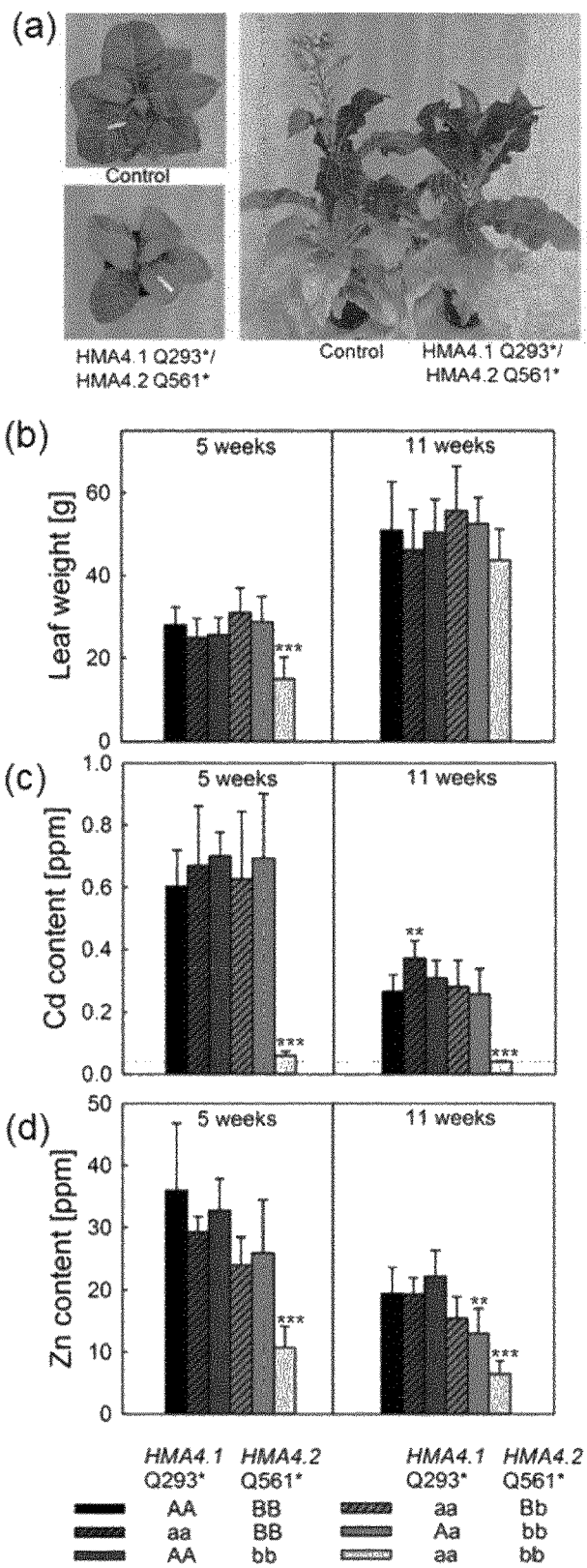
FIG. 4: (a) Phenotype, (b) leaf fresh weight and (c) leaf Cd and (d) leaf Zn levels in dry weight of mutant plants containing decreasing numbers of functional HMA4 alleles after five (left) and eleven (right) weeks growth in the greenhouse. The genotype is indicated beneath the panels: A and a are the wild-type and mutant alleles for HMA4.1, B and b are wild-type and mutant alleles for HMA4.2. Bars and errors represent mean±SD of eight plants. *, , and * indicate levels of significance at P<0.05, P<0.01 and P<0.001, respectively, compared to the WT control plants. The dotted line indicates LOQ=0.05 ppm for Cd measurement.

In a greenhouse experiment, six combinations of mutations are tested. For each of them, eight plants carrying two homozygous mutations are grown together with eight plants homozygous for only one mutation in HMA4.1, eight plants homozygous only for a mutation in HMA4.2 and eight null-segregant plants for both HMA4 genes. For the double nonsense mutants, also two other genotypes are included: eight plants that are homozygous nonsense mutants for HMA4.1 and heterozygous nonsense mutants for HMA4.2 and eight plants that are homozygous nonsense mutants for HMA4.2 and heterozygous nonsense mutants for HMA4.1, these latter groups only containing one functional non-mutant allele. After five and eleven weeks growth on soil (a), lower stalk position leaves are harvested for fresh weight determination (b) and Cd, Zn analysis (FIG. 4c, d).

Unlike the simple nonsense mutants and the nonsense mutants with one functional HMA4 allele, only the double nonsense mutant HMA4.1 Q293*IHMA4.2 Q561* shows a similar Cd reduction as the reduction observed for the HMA4 RNAi plants. After five weeks growth on soil, homozygous double nonsense mutants shows a Cd reduction from 0.6 ppm in control plants to levels around the limit of quantification (LOQ=0.05 ppm), while Zn content is only reduced by one third (FIG. 4c, d). Cd analysis after eleven weeks shows that the greenhouse plants with further plant growth diluted Cd in the increasing biomass. Mean control levels are at around 0.3 ppm Cd while the two double mutant lines analysed shows Cd levels below the limit of quantification (FIG. 4c). Interestingly, single nonsense mutants and mutant plants carrying only one functional HMA4 allele shows intermediate Zn content while exhibiting control Cd levels. These Zn levels seem sufficient for normal growth, as no growth difference is observed in these plants, compared to the control. The homozygous double nonsense mutants on the other hand show a 50% reduction in leaf weight after five weeks of growth. However, after eleven weeks, mutant plants reach the same size as the control (FIG. 4a, b), only flowering is slightly delayed.

Figure 5:
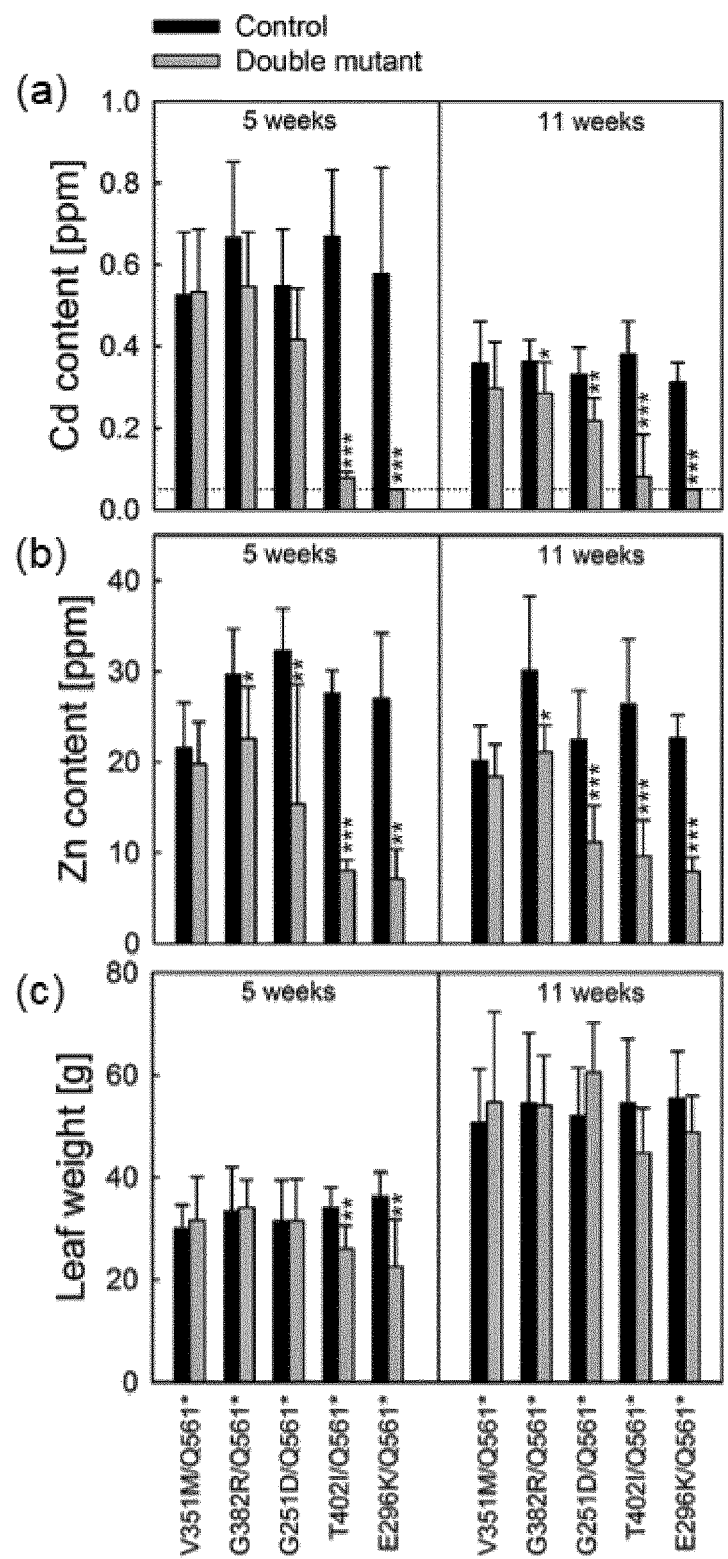
FIG. 5: Analysis of (a) leaf Cd and (b) Zn and (c) leaf fresh weight in the different double mutant plants and their respective HMA4 WT null-segregant controls grown for five and eleven weeks on soil in the greenhouse. Black bars indicate the null-segregant controls, grey bars the respective HMA4 homozygous double mutants. *, , and * indicate levels of significance at P<0.05, P<0.01 and P<0.001, respectively, compared to the WT control plants. The dotted lines indicates LOQ=0.05 ppm for Cd measurement.

Of the other mutant combinations investigated after five weeks growth, two other combinations (E296K/Q561* and T402I/Q561*) show a similar Cd reduction as the double nonsense mutant while containing only one third of control Zn content (FIG. 5a, b). These two lines display likewise delayed growth: at an early stage T402I/Q561* showed about 25% leaf weight reduction and E296K/Q561* showed 50% reduced leaf weight (FIG. 5c). After growth for six more weeks, there are no significant differences in leaf size and height any more between controls and double mutants. However, in the double mutant lines flower formation is slightly delayed. Two other mutation combinations (G382R/Q561* and G251D/Q561*) do not show significant Cd reduction. All Cd and Zn data are summarized in Table 8. For the control group in Table 8 values of all individual control plants are grouped together.

Altogether, these experiments show that both HMA4 genes need to be at least partially impacted to reduce Cd levels significantly.

Example 5—Validation of Cd Reduction in Two Field Trials Under Moderate Cd Conditions Two field experiments are conducted under moderate cadmium conditions in order to confirm the greenhouse data. In the first experiment, the same genotype groups (single mutants, double mutants and control plants) are grown in six replicate plots. Each replicate unit contains 10 plants of the double mutant, the HMA4 WT control and the two simple mutants, respectively. For the double nonsense mutants, also the two other genotypes containing one functional non-mutant allele are included (homozygous nonsense mutants for HMA4.1/heterozygous nonsense mutants for HMA4.2 and heterozygous nonsense mutants for HMA4.1I homozygous nonsense mutants for HMA4.2). Plants are grown for 14 weeks in a field in Switzerland. Plant phenotypes are investigated and leaves at mid-stalk position harvested, dried and subjected to Cd/Zn analysis. P-values are calculated for the probability that the observed reduction in Cd in the mutant by more than 20% compared to the control is by chance.

Globally, the field and the greenhouse data are corresponding. While the single mutants do not show any Cd reduction compared to the controls (Table 2), the same double mutant lines that had been low in Cd in the greenhouse (T402I/Q561*; E296K/Q561*; Q293*/Q561*), as well as an additional double nonsense mutant (Q293*/W265*), shows likewise more than ten-times reduced Cd content under field conditions with a probability p<0.05 (highest p-value=0.0054) that the mean double mutant value is at least 20% reduced (Table 4). Besides these four lines, line G251D/Q561* show 30% Cd reduction, however, in this line the Cd content is not significantly more than 20% reduced (p-value=0.1029). While Zn content is reduced by around 70% in the greenhouse, the low Cd lines (T402I/Q561*; E296K/Q561*; Q293*/Q561*; Q293*/W265*) grown in the field show only a maximum of around 50% Zn reduction (Table 4). In the first field trial, leaf weight is reduced in line E296K/Q561*, whereas in the three other low Cd lines (T402I/Q561*; Q293*/Q561*; Q293*/W265*) leaf weight is not significantly affected (FIG. 6b). Plant and leaf morphology is not affected by the mutations. However, for lines E296K/Q561*, Q293*/Q561* and Q293*/W265*, necrotic spots are observed on the lower leaves, especially at an early growth stage. The double mutants T402I/Q561* and G251D/Q561* show the best phenotypes and do not display necrotic lesions at any time. These two lines are hardly distinguishable from their controls.

Figure 7:
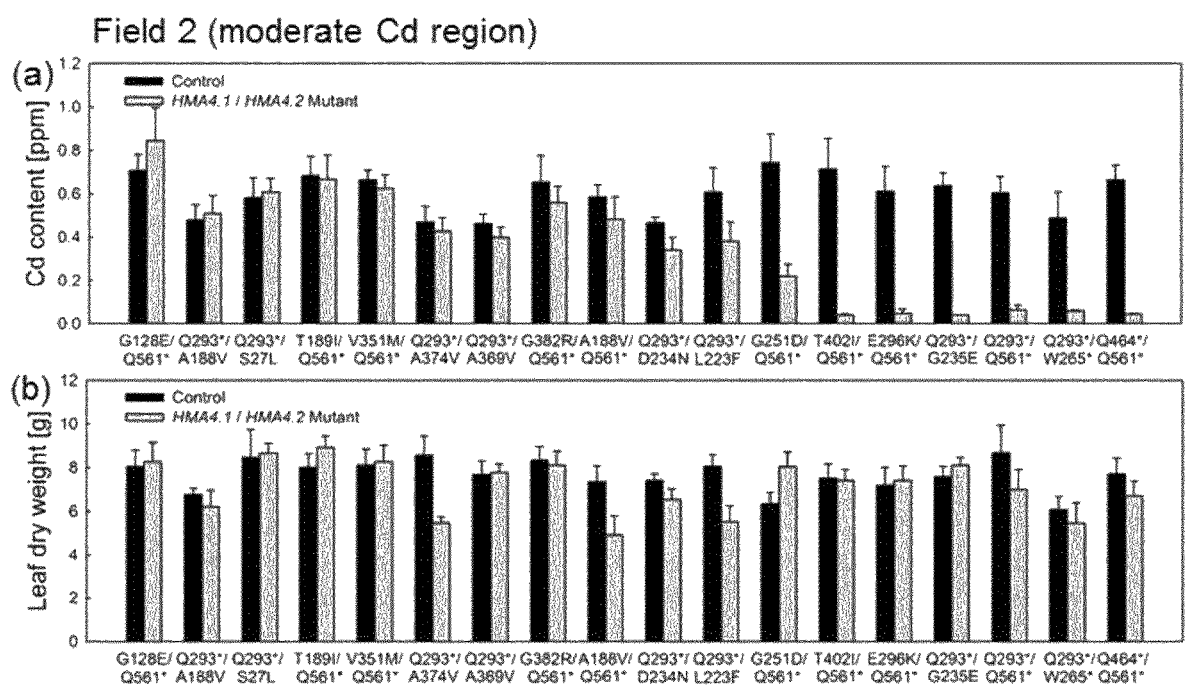
FIG. 7: (a) Leaf Cd and (b) leaf dry weight data of the HMA4 mutants grown in the field in a region where a moderate Cd content is present. Black bars indicate the null-segregant controls, grey bars the respective HMA4 homozygous double mutants. Leaf pooled samples were collected at lower stalk position in six (for Q293*/W265* and Q293*/D234N four) replicated plots. Bars and error represent mean and standard deviation.

In a second field trial, the same mutation combinations are grown together with additional combinations (18 in total) in the field. This time one experimental unit contains 20 homozygous HMA4 double mutant plants and 20 HMA4 WT control plants. The single mutants are not analysed again. The Cd/Zn data are shown in Table 5; graphs on Cd data and phenotypic data are depicted in FIG. 7. The same lines that show a Cd reduction in the first field trial, show again a comparable Cd reduction; except line G251D/Q561* which even shows 70% Cd reduction this time. Besides these lines, one more double nonsense mutations is analysed (Q464*/Q561*) and shows as expected a very strong Cd reduction of 94%. Likewise the new mutation combination Q293*/G235E show 94% Cd reduction. The mutation combinations Q293*/L223F and Q293*/D234N exhibit intermediate Cd reduction (37% and 27%, respectively). The lines Q293*/Q561*, Q293*/W265*, Q464*/Q561*, Q293*/G235E, E296K/Q561*, T402I/Q561*, G251D/Q561*, and Q293*/L223F show a significant more than 20% Cd reduction (p<0.05; highest p-value=0.0007). The line Q293*/D234N shows a 27% Cd reduction, but the reduction is not bigger than 20% with p<0.05. All other double mutants analysed only show less than 20% Cd reduction and thus are not interesting for further development. The mutation combinations Q293*/Q561* and Q293*/W265*, Q464*/Q561*, Q293*/G235E and E296K/Q561* show necrotic spots on the leaves and reduced growth rate at an early stage. However, at harvest time, no clear difference is seen between these double mutants and their controls. Leaf dry weight of most mutant lines in the field is similar to their control plants (FIG. 7b). In some cases, leaf dry weight differs slightly from the controls, however, without being correlated to the Cd reduction.

Figure 8:
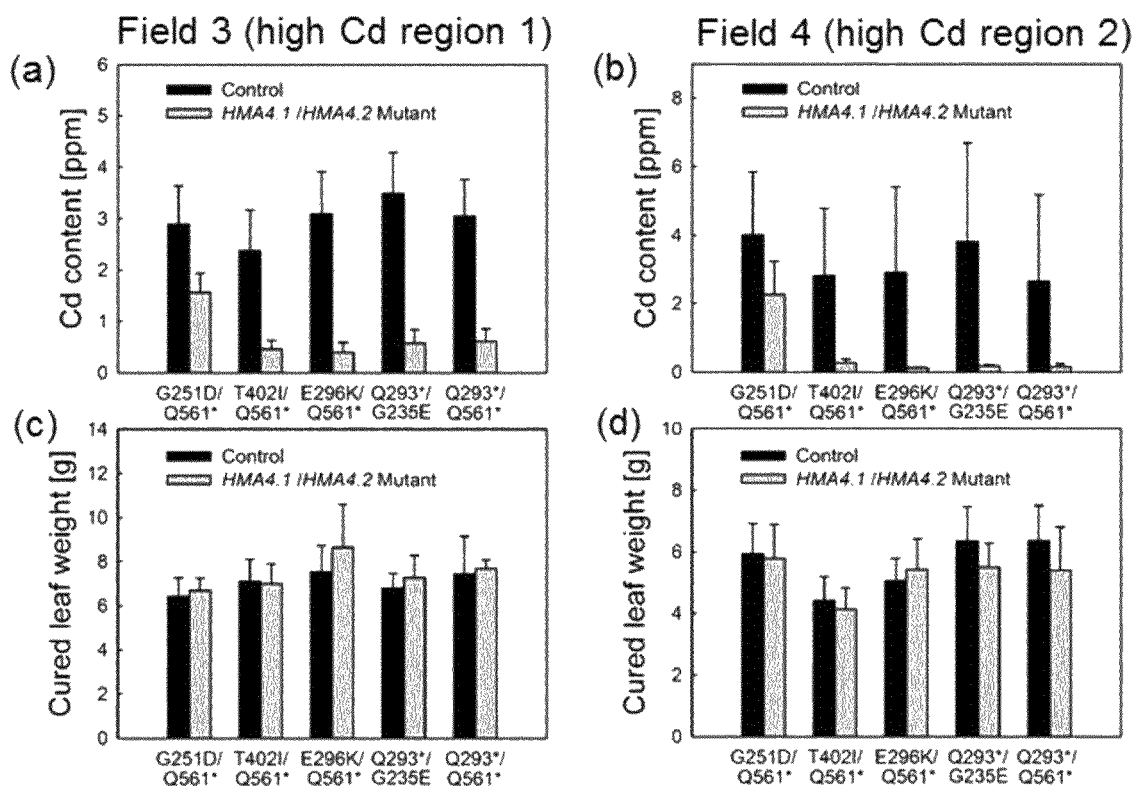
FIG. 8: (a, b) Leaf Cd and (c, d) cured leaf weight data of the HMA4 mutants grown in the field in two regions where a high Cd content is present. (a) and (c) correspond to Cd and cured leaf weight data from field 3 and b and d to Cd and cured leaf weight data from field 4. Black bars indicate the null-segregant controls, grey bars the respective HMA4 homozygous double mutants. Leaf pooled samples were collected at lower stalk position in five replicated plots. Bars and error represent mean and standard deviation.

Example 6—Validation of Cd Reduction in Two Field Trials Under High Cd Conditions In two small field trials, five promising low Cd mutation combinations (the double nonsense mutation combination Q293*/Q561* as well as the combinations Q293*/G235E, E296K/Q561*, T402I/Q561* and G251D/Q561*) as well as their respective controls are grown in two regions that are known for high Cd content. Cd/Zn data are shown in Table 6; graphs on Cd and phenotypic data are shown in FIG. 8. The control plants accumulate around 3 ppm Cd, whereas the Cd content is reduced by 80c/o and by 90c/o for mutation combinations Q293*/Q561*, Q293*/G235E, E296K/Q561* and T402I/Q561* in the first (field 3) and second region (field 4), respectively. For the combination G251D/Q561* the Cd reduction is at around 45% in both field locations. For all lines the probability that the mean is below 20% is significant (p<0.05; highest p-value=0.0068). No impact on leaf weight is observed (FIG. 8b). Altogether, the field data show that under agricultural field conditions, even in different regions, HMA4 mutation combinations have the potential to reduce Cd content by 5 to 10-fold. Plant development and yield do not seem to be impacted at a later stage in the cultivar AA37.

Example 7—NtHMA4 is the Key Enzyme for Root-to-Shoot Cd Translocation

In HMA4 RNAi lines as well as HMA4 double nonsense mutants described herein, leaf Cd can be reduced by more than 10-fold, indicating that Cd root-to shoot transfer in tobacco is essentially dependent on HMA4. Mutations in both HMA4 genes are necessary to breed for low Cd tobacco. Under both greenhouse and field conditions, HMA4 double nonsense mutants exhibit 90% Cd reduction. Under all Cd conditions tested, a nonsense mutation in only one of the HMA4 genes is not able to reduce Cd content in tobacco plants.

Interestingly, under extremely high non-naturally occurring Cd conditions, 50% reduction of Cd has been observed in plants carrying only one nonsense mutation in one of the NtHMA4 genes (Hermand, 2014). This corresponds to what has been observed in *Arabidopsis*, where on high Cd agar medium, the knockout of AtHMA4 reduced shoot Cd content by more than 50%, whereas simultaneous knockout of both these transporter genes leads to an even greater reduction (Wong and Cobbett, 2009). Our study on NtHMA4.1 and NtHMA4.2 demonstrates that results from artificial systems need to be confirmed under soil and field conditions to evaluate the impact of a mutation for plant breeding.

Like for many crop species diverse tobacco cultivars exist. They exhibit large differences e.g. in fertilization requirements and accumulation of amino acids and sugars (Lewis et al., 2012). In the three cultivars analysed, TN90, K326 and AA37, HMA4 disruption shows a comparable effect, i.e. in all of these cultivars Cd reduction by more than 90% is achieved. However, despite the comparable effect seen on Cd and Zn reduction, plant performance is very different. While K326 is only slightly affected by the lack of HMA4, exhibiting rounder leaf shape and increased leaf veins with constant biomass and plant size, TN90 shows strongly stunted growth and necrotic lesions, whereas AA37, not being a typical Burley plant like TN90, displays only small effects. This underlines the metabolic differences between tobacco cultivars with respect to Zn homeostasis. Supply of Zn to the soil is able to restore the phenotype which indicates that other transporters can compensate for HMA4 and mediate Zn uptake, although on a lower level.

Example 8—Low Cd Combined with Unaffected Phenotype Requires Fine-Tuning of Both NtHMA4 Homeologs In order to minimize phenotypic effects of HMA4 double knockout, a second mutation is identified in one of the HMA4 genes. The aim is that when breeding this combination in a variety of choice, it is sufficient to reduce Cd significantly, but without affecting the plant phenotype. While in the AA37 EMS mutant background an effect is especially visible at an early growing stage, no clear impact on growth and biomass can be observed at a later stage. However, according to the data of the HMA4 RNAi lines (FIG. 3) according to the variety of interest and especially in Burley varieties, a negative impact on growth might occur. In the following, mutation combinations that are considered especially useful for further plant breeding are described. Besides the double HMA4 knockout mutants (Q293*/Q561*, Q293*/W265*, Q464*/Q561*), further combinations were identified with comparable Cd reduction (80-90%):

While the double mutants E296K/Q561* and Q293*/G235E show a similar phenotype as the double knockout mutants at an early stage (necrotic lesions, reduced growth), the T402I/Q561* mutant plants displays better growth and do not exhibit necrotic patches on the leaves at an early stage. The combination G251D/Q561* provides 30 to 70% Cd reduction and a phenotype that cannot be distinguished from the control. Two more mutations combinations (Q293*/L223F and Q293*/D234N) only show low Cd reduction (37% and 27%, respectively in one field trial).

A second greenhouse experiment was performed with additional mutation combinations in which the combination H438Y/W265* showed 58% Cd reduction and no impact on phenotype (Table 9).

The above described mutation combinations offer the possibility to dose Cd and Zn content and to find the optimal mutation combination for each cultivar. For a cultivar such as Burley, which is more impacted by lack of HMA4 as shown in transgenic lines (FIG. 3), it might be necessary to use an intermediate solution (e.g. G251D/Q561*, H438Y/W265*, Q293*/L223F, or Q293*/D234N).

Figure 9:
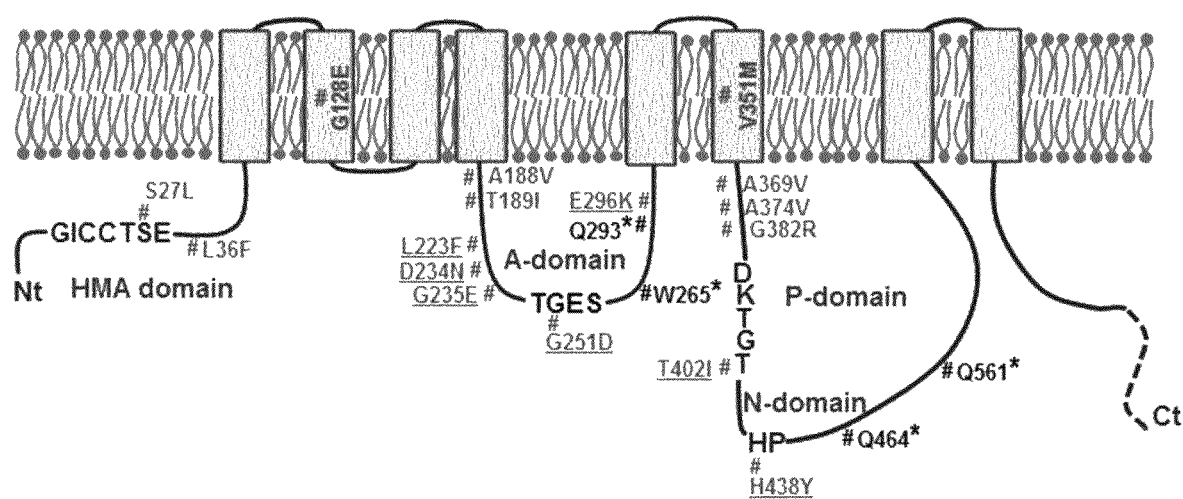
FIG. 9: Scheme of the *N. tabacum* HMA4 proteins. Three functional domains carry out catalytic functions: the phosphorylation (P), nucleotide binding (N) and actuator (A) domains which are located in the second and third cytoplasmic loop of the protein. The missense mutations that were found to have an impact on protein function and reduced Cd in combination with a nonsense mutation are highlighted with underscore characters. All other missense mutations analysed in this study had no impact on Cd reduction when combined with a nonsense mutation. Nonsense mutations are highlighted in black. (This model only serves for illustration purposes and does not reflect domain folding.)

In the following, the localisation of the mutations was investigated (FIG. 9). Heavy metal ATPases comprise three domains that are important for catalytic function: the phosphorylation (P), nucleotide binding (N) and actuator (A) domains. The P-domain is composed of the N- and C-terminal parts of the third cytoplasmic loop. The middle part of the loop is the N-domain. A DKTGT motif is found in the P-domain. The aspartate residue in this motif is predicted to be phosphorylated in the active enzyme during catalysis. In the A-domain, the catalytically active TGE(S) loop protrudes from the structure, interacting with the phosphorylated site in the ATP-binding domain (Banci et al., 2009).

Five functional mutations that have an impact on Cd uptake are found in the A (actuator)-domain of the transporter (L223F, D234N, G235E, G251D, E296K) with G251* being localised in the TGES motif. It is known from other HMA transporters that mutations occurring in the A-domain either destabilize the fold of the domain or affect interactions with the other domains of the enzyme (Banci et al., 2009). The T402I mutation is found in the DKTGT motif, the P (phosphorylation)-domain in the third cytoplasmic loop of the protein. The H438Y mutation is found in the HP motif of the N (nucleotide binding)-domain in the third cytoplasmic loop of the protein which might act by impairing nucleotide coordination.

In conclusion, two mutations are necessary to inhibit Cd translocation, one of them being a full knockout and the second a nonsense or a missense mutation likely located either in the A-domain, in the DKTGT motif of the P-domain or in the HP locus of the N-domain in the second HMA4 copy.

Altogether, this work highlights the need to identify a suitable system to measure the effect of HMA4 mutations and their combinations on Cd content and phenotype. This work shows the importance of fine-tuning HMA4 root-to-shoot translocation system in order to obtain low Cd tobacco without phenotypic alterations for all cultivars on interest.

REFERENCES

Arnould, S., Delenda, C., Grizot, S., Desseaux, C., Pâques, F., Silva, G. H., and Smith, J. (2011). The I-CreI meganuclease and its engineered derivatives: applications from cell modification to gene therapy. *Protein Eng Des Sel.* 24(1-2):27-31.

Banci, L., Bertini, I., Cantini, F., Migliardi, M., Natile, G., Nushi, F., and Rosato, A. (2009). Solution structures of the actuator domain of ATP7A and ATP7B, the Menkes and Wilson disease proteins. Biochemistry 48(33): 7849-7855

Bortesi, L., and Fischer, R. (2015). The CRISPR/Cas9 system for plant genome editing and beyond. *Biotechnol Adv.* 33(1):41-52.

Chen, K, and Gao, C. (2014). Targeted genome modification technologies and their applications in crop improvements. Plant Cell Rep. 33(4):575-583.

Chen, L., Hao, L., Parry, M. A., Phillips, A. L., and Hu, Y. G. (2014). Progress in TILLING as a tool for functional genomics and improvement of crops. *J Integr Plant Biol.* 56(5):425-443.

Dey, N., and Maiti, I. B. (1999). Structure and promoter/leader deletion analysis of mirabilis mosaic virus (MMV) full-length transcript promoter in transgenic plants. *Plant Mol Biol.* 40(5):771-82.

Fricano, A., Bakaher, N., Del Corvo, M., Piffanelli, P., Donini, P., Stella, A., Ivanov, N. V., and Pozzi, C. (2012). Molecular diversity, population structure, and linkage disequilibrium in a worldwide collection of tobacco (*Nicotiana tabacum* L.) germplasm. BMC Genet. 13:18. doi: 10.1186/1471-2156-13-18.

Gravot, A., Lieutaud, A., Verret, F., Auroy, P., Vavasseur, A., and Richaud, P. (2004). AtHMA3, a plant P1B-ATPase, functions as a Cd/Pb transporter in yeast. *FEBS Lett.* 561(1-3):22-28.

Hermand, V., Julio, E., Dorlhac de Borne, F., Punshon, T., Ricachenevsky, F. K., Bellec, A., Gosti, F., and Berthomieu, P. (2014) Inactivation of two newly identified tobacco heavy metal ATPases leads to reduced Zn and Cd accumulation in shoots and reduced pollen germination. *Metallomics,* 6(8), 1427-1440.

Horsch, R. B., Fry, J. E., Hoffmann, N. L., Wallroth, M., Eichholtz, D., Rogers, S. G. and Fraley, R. T. (1985). A Simple and General Method for Transferring Genes into Plants. *Science,* 227, 1229-1231

Hussain, D., Haydon, M. J., Wang, Y., Wong, E., Sherson, S. M., Young, J, Camakaris J, Harper J F, Cobbett C S. (2004) P-type ATPase heavy metal transporters with roles in essential zinc homeostasis in *Arabidopsis*. Plant Cell, 16(5), 1327-1339.

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. *Genome Biology* 14:R36.

Korenkov, V., King, B., Hirschi, K., and Wagner, G. J. (2009). Root-selective expression of AtCAX4 and AtCAX2 results in reduced lamina cadmium in field-grown *Nicotiana tabacum* L. *Plant Biotechnol J* 7(3):219-226.

Lewis, R. S., Parker, R. G., Danehower, D. A., Andres, K., Jack, A. M., Whitley, D. S., and Bush, L. P. (2012) Impact of alleles at the Yellow Burley (Yb) loci and nitrogen fertilization rate on nitrogen utilization efficiency and tobacco-specific nitrosamine (TSNA) formation in air-cured tobacco. *J Agric Food Chem.* 60, 6454-6461.

Liedschulte, V., Laparra, H., Battey, J., Goepfert, S., and Bovet, L. Missense or nonsense mutations in either HMA4.1 or HMA4.2 do not significantly reduce cadmium content in the leaves of tobacco plants grown under field conditions. Poster session presented at: The 12th Solanaceae conference; 2015 Oct. 25-29; Bordeaux, France.

Lugon-Moulin, N., Martin, F., Krauss, M. R., Ramey, P. B., and Rossi L. (2006) Cd concentration in tobacco (*Nicotiana tabacum* L.) from different countries and its relationship with other elements. *Chemosphere* 63, 1074-1086.

Morel, M., Crouzet, J., Gravot, A., Auroy, P., Leonhardt, N., Vavasseur, A., and Richaud, P. (2009). AtHMA3, a P1B-ATPase allowing Cd/Zn/Co/Pb vacuolar storage in *Arabidopsis*. *Plant Physiol.,* 149(2), 894-904.

Ng, P. C., and Henikoff, S. (2003). SIFT: Predicting amino acid changes that affect protein function. Nucleic Acids Res. 31(13):3812-4.

Petolino, J. F. (2015). Genome editing in plants via designed zinc finger nucleases. In Vitro Cell Dev Biol Plant. 51(1):1-8.

Puchta, H., and Fauser, F. (2013). Gene targeting in plants: 25 years later. *Int J Dev Biol.* 57(6-8):629-37.

Qiwei, S., and Caixia, G. (2015). Research progress of genome editing and derivative technologies in plants. *Yi Chuan.* 37(10):953-973.

Sambrook, J., Fritsch, E. F., and Maniatis, T. (1989). Molecular Cloning: A Laboratory Manual, Cold Spring Harbor Laboratory Press, Cold Spring Harbor, N.Y.

Schneider, C. A., Rasband, W. S., Eliceiri, K. W. 2012. NIH Image to ImageJ: 25 years of image analysis. Nature Methods 9, 671-675, 2012.

Sierro, N., Battey, J. N. D., Ouadi, S., Bakaher, N., Bovet, L., Willig, A., Goepfert, S., Peitsch, M. C., and Ivanov, N. V. (2014) The tobacco genome sequence and its comparison with those of tomato and potato. *Nature Communications* 5, Article number: 3833

Trapnell, C., Hendrickson, D., Sauvageau, M., Goff, L., Rinn, J. L., and Pachter, L. (2013). Differential analysis of gene regulation at transcript resolution with RNA-seq. Nature Biotechnology 31: 46-53.

Wong, C. K., and Cobbett C. S. (2009) HMA P-type ATPases are the major mechanism for root-to-shoot Cd translocation in *Arabidopsis thaliana*. *New Phytol.,* 181 (1), 71-78.

Wright, D. A., Li, T., Yang, B., and Spalding, M. H. (2014) TALEN-mediated genome editing: prospects and perspectives. *Biochem J.* 462(1):15-24.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

| SEQUENCES |
|---|

SEQ ID NO: 1
Amino acid sequence of *Nicotiana tabacum* heavy metal ATPase (NtHMA4.1)
GenBank Accession No: CCQ77798.
```
   1 MVESEKMNET KKLSKSYFDV LGICCTSEVV LVEKILKNLE GVKEVSVIVT TKTVIVIHDS
  61 LLISPQQIVK ALNQARLEAS IRVKGEKNYQ KKWPSPFAIG SGILLGLSFL KYFFAPFQWL
 121 ALAAVAVGIP IIFRGVAAV RNLTLDINIL VLIAVAGSIV LHDYWEAGTI VFLFAIAEWL
 181 ESRASHKATA AMSSLVNIVP PTAVLAESGE VVNVDEVKHN SILAVKAGET IPIDGVVVEG
 241 ECDVDEKTLT GESFPVSKQR DSTVWAGTTN LNGYISVKTT ALAEDCAVAR MAQLVEDAQN
 301 KKSKTQRYID KCAKYYTPAI VAISASLAIV PTALRVHNRN EWYRLALVTL VSACPCALVL
 361 STPVAMCCAL SKAATSGLLF KGAEYLETLA KIKIMAFDKT GTITKGEFMV TEFKSLIDGF
 421 SLNTLLYWVS SIESKSGHPM AAALVDYAQS NSVEPKPDRV EQFQNFPGEG IFGRIDGMEI
 481 YVGNRKISSR AGCTTVPEIE GDSFKGKSVG YIFLGSSPAG IFSLSDVCRI GVKEAMRELK
 541 QMGIKTAMLT GDCYAAANHV QDQLGGALDE FQAELLPEDK ATIIKGFQKE APTAMIGDGL
 601 NDAPALATAD IGISMGISGS ALAKETGHVI LMTNDIGRIP KAARLARRVR RKIVENMIIS
 661 VVTKAAIVAL AIAGYPLVWA AVLADTGTCL LVILNSMLLL RGGTRRHGKK CWRSSTPSHA
 721 PHHKDKASCC KSENAPQLCC SDIESQKKCT SQSCSSEVCV PRCQPVSSGS KSCGNNQCPD
 781 SIENSGFHSH RRPQCCSSKM AAKACQSAVS ESKSCGNNQC PDSVENSGFH SHPRPECCSS
 841 KMAAKACQSA VSESKSCGNN QCPDSVENSG FHSHPRPQCC SSKMAAKAGQ SALSESKSCG
 901 NNNCSDSIHK SNCHSLTNSL VCSSKMSAPQ CHSATSSNKS CGSTKCSDFS DKKCCQSDKI
 961 PQTCSTKKSA PGCQSAVSGS KSCGNSKCSD SKDNSSHPSH PDHQTCMSKL CAPQSQSATS
1021 SSRTCGNTKC SDTNSKNSCY SQTNSESCSS KMSGPSCKTA NSGSRSCRNK KCQDSATENS
1081 FHSPLTNPLS GEKLSEQKSL DLVRKDKESS HDLRHGCSDE EHDHTNLDKA YDSCALQECC
1141 YSVQGNKTDV SETGIQETAH CDSTNQTCQT ASSGSMTCGN DKILDSLSIH GCHSHDNPLH
1201 EENNLEQKIL DVVGEGIKSP HAVGHGCSDK EHDHSHPEKA YDSCATDDCC FSVQVHGIDD
1261 VSKSEIQETA HCDSTKQSMV ISSSCKHEPK DQVNHCGLHS KTTPTDEELA KLVRRCCKYK
1321 PCHDVRSGCR KHAAECGPTV RSTINILRDN HHHYLDCSGR KVCSLLEKRH IGGCCDSFRK
1381 ECCAKKKHLG ASFGGGLSEI VIE
```

SEQ ID NO: 2
Amino acid sequence of *Nicotiana tabacum* heavy metal ATPase (NtHMA4.2)
GenBank Accession No: CCW03243.1.
```
   1 MVESEKMNDT KNLSKSYFDV LGICCTSEVV LVEKILKNLE GVKEVSVIVT TKTVIVIHDS
  61 LLISQQQIVK ALNQARLEAS IRVKGEKNYQ KKWPSPFAIG SGILLGLSFL KYFFAPFQWL
 121 ALAAVAVGIP IIFRGVAAV RNLTLDINIL VLIAVTGSIV LHDYWEAGTI VFLFTIAEWL
 181 ESRASHKATA AMSSLVNIVP PTAVLAESGE VVNVDEVKLN SILAVKAGET IPIDGVVMEG
 241 ECDVDEKTLT GESFPVSKQI DSTVWAGTTN LNGYISVKTT ALAEDCAVAR MAQLVEDAQN
 301 KKSKTQRYID KCAKYYTPAI VAISASLAIV PTALRVHNRN EWYRLALVTL VSACPCALVL
 361 STPVAMCCAL SKAATSGLLF KGAEYLETLA KIKIMAFDKT GTITRGEFMV TEFKSLVDGL
 421 GLNTLLYWVS SIESKSGHPM AAALVDYAQS NSVEPKPDRV EQFQNFPGEG IFGRIDGMEI
 481 YVGNRKISSR AGCTTVPEIE GDSFQGKSVG YIFLGSSPAG IFGLSDVCRI GVKEAMRELK
 541 QMGIKTAMLT GDCYAAANHV QDQLGGAMDE FQAELLPEDK ATIIKGFQKE APTAMIGDGL
 601 NDAPALATAD IGISMGISGS ALAKETGHVI LMTNDIGRIP KAARLARRVR RKIVENMIIS
 661 VVTKAAIVAL AIAGYPLVWA AVLADTGTCL LVILNSMLLL RVGTHRHGKK CCRSATPSHA
 721 PNHKDKASCC KSENAPQLCC SDIESQKKCT SQSCSSEVCV PRCQPVSSGS KSCGNNQCPD
 781 SVENSGFHSH PRPQCCSSKM ASKACQSAVS ESKSCGNNQC PDSVENSGFH SHPRPQCCSS
 841 KMASKACQSA VSESKSCGNN QCPDSVENSG FHSHPRPQCC SLKMASKACQ SAVSESKSCG
 901 NNQCPDSVEN SGFHSHPRPQ CCSSKMAAKA CQSAVSESKS CGNNNCSESI YKSSCHSLTS
 961 SLVCSSKMSA PQCHSATSSS KSCGSTKCSN FSDKKCCQYD KIPQTCSTKK SAPGCQSAVS
1021 GSKSCGDSKC SDSKDNSSHP SHPDHQICTS KLCAPQSQSA TSSSRTCGNM KCSDTNSKNS
1081 CYSHTNSESC SSKMSGPACK TANSGSRLCG NKKCCLDSANE NSFHSLTNPL CEEKLLEKES
1141 LDLARKDRES NHDLSHGCSD EEHDHLNLDK AHDSCALQEC CYSVQGNKTD VSETGIQEAA
1201 HCDSINQTCQ TAISGSMTCG NNKSLDSLSI HGCHSHDSPL HKESNLEQKS LDVAGEGIKS
1261 PHAVGQGCSD KEHNHSHPEK AYDSCATDDC CFSVQVHGID DVSRSEIQET AHCDSTKQST
1321 VIPSSCEHEP KDQVNHCGSH SKSIPTDEEL AKLVRRCCKY KPCHDVRSGC RKHAAECGPT
1381 VRSTINILRD NHHHHLDCSG RKVCSLLEKR HIGGCCDSFR KECCAKNNHL GASFGGGLSE
1441 IVIE
```

SEQ ID NO: 3
Polynucleotide sequence of *Nicotiana tabacum* heavy metal ATPase (NtHMA4.1)
GenBank Accession No: HF675181.1.
```
   1 agagaaggag aaaaatggtg gaaagtgaaa aatgaatga aacaaagaag ttgagcaaga
  61 gctattttga tgttttggga atttgctgta cttcagaagt tgttctagtt gaaaaaattc
 121 tcaagaatct tgaagggtt aaagaggttt cagtaattgt cacaacaaag actgtcattg
 181 ttattcatga ttctcttctc atttctccgc aacaaattgt taagcattg atcaagcaa
 241 gattagaagc aagcataaga gtgaaggag agaaaacta ccaaagaaa tggccaagtc
 301 catttgcaat tggcagtgga atattgcttg gactctcatt tttgaagtac tttttgcac
 361 ctttccaatg gttagcactt gcagctgttg cagttgggat tcctccaatt attttttagag
 421 gtgtggctgc cgtgcgaaac ctcactcttg acatcaacat tcttgtttta atagcagtgg
 481 ctggatcaat tgttttacac gattattggg aagctggtac tattgtcttc ttattcgcca
 541 ttgcagaatg gctagagtca agggcaagtc acaaggctac cgctgctatg tcatcactgg
 601 tcaatatagt ccctccaaca gcagttttag ctgaaagcgg agaagtcgta aatgttgatg
 661 aagtcaaggt gaatagcatt cttgctgtga agctggtga actatacctt attgatggag
 721 ttgtagtgga aggggaatgt gacgtgacg agaaaacact gacaggcgag tcgtttccag
 781 tttctaagca aagagattca acggtctggg ctggcactac aaatctaaat ggctatatca
 841 gtgttaagac tacggctttg gctgaagatt gtgcggtggc taggatggca cagcttgtcg
 901 aagatgctca gaacaagaaa tcaaaaaccc aaagatacat cgacaagtgt gctaaatatt
 961 ataccagca aattgtggct atatcagctt cttggcaat tgttcctact gcattaagag
1021 ttcacaatcg aaatgaatgg tatcgcttgg ctttggtcac attggtgagt gcatgtccgt
1081 gtgcacttgt tctatctaca ccagttgcca tgtgttgcgc actttcaaaa gcagcaacgt
```

```
1141 ccggtcttct gtttaaagga gcagagtacc ttgagactct agctaaaatc aaaatcatgg
1201 cttttgacaa aacagggact ataactaaag gagaatttat ggtgaccgag ttcaagtctc
1261 tgattgatgg ttttagtctc aatacactgc tttactgggt ttcaagcatt gagagcaagt
1321 caggtcatcc gatggcagcc gctctggtgg actatgcaca atcaaattcc gttgagccaa
1381 agcctgatag agttgagcag tttcaaaatt ttcctggtga agggatattt ggaagaattg
1441 atggaatgga aatctatgtc gggaatagga aaatttcttc aagagctgga tgtaccacag
1501 taccagaaat agagggtgat agtttcaaag gaaagtctgt tggatacata ttttttgggat
1561 catctccagc tggaattttc agtctttccg atgtttgtcg aattggtgta aaagaagcaa
1621 tgagagaact gaagcagatg ggtatcaaaa ccgcgatgct tactggtgat tgttatgcag
1681 ctgccaacca tgtgcaggat cagttaggtg gagctttgga tgaatttcaa gcagaactcc
1741 taccagagga caaggcaaca atcatcaagg gttttcagaa ggaagctcca acagcgatga
1801 taggcgacgg ccttaatgat gctcctgcat tagcaacggc tgacattggc atctcaatgg
1861 gcatctctgg gtcagctctc gctaaagaaa caggccatgt tatactaatg acaaatgaca
1921 tcggaagaat accgaaagct gcacgtcttg ctagaagagt tcgaaggaag attgttgaga
1981 atatgattat atcagtcgtt acaaaggctg ccatagttgc attggcaata gcaggttatc
2041 cattggtttg ggctgctgtc ctcgcagata ctggagcatg cttgctagtg attttgaaca
2101 gcatgctact tctacgagga ggcacacgca gacatgggaa aaaatgttgg agatcttcta
2161 ctccttcgca tgctccccac cacaaagaca aagcttcatg ttgcaagtcg gaaaatgctc
2221 cccagctgtg ttgctctgat attgagtcac aaaagaaatg tacaagtcaa tcatgctcgt
2281 ccgaggtgtg tgttccaaga tgtcaacctg tctcctcaga atcaaagtca tgtggaaata
2341 atcagtgccc agactccatt gaaaatagtg gttttcattc tcatcgccgt cctcaatgct
2401 gctcgtcgaa gatggctgct aaagcatgcc aatctgcagt ttcagaatca aagtcatgcg
2461 gaaataatca gtgcccagac tccgttgaaa atagtggttt tcattctcat ccccgtcctg
2521 aatgctgctc gtcgaagatg gctgctaaag cgtgccaatc tgcagtttca gaatcaaagt
2581 catgtggaaa taatcagtgc ccagactccg ttgaaaatag tggttttcat tctcatcccc
2641 gtcctcaatg ctgttcatcg aagatggctg ctaaagcagg ccaatctgca ctttcagaat
2701 caaagtcatg tggaaataac aattgctcag actccattca caagagtaat tgtcattctt
2761 taactaactc tctagtatgt tcttccaaga tgtctgctcc acaatgtcat tctgctactt
2821 caagcaacaa atcatgtgga agtaccaagt gctccgactt cagtgacaaa aaatgttgtc
2881 aatccgacaa aattcctcaa acgtgctcta ccaagaagtc tgctccagga tgtcaatctg
2941 cagtttctgg gtctaaatca tgtggaaata gcaagtgttc agactcaaaa gacaatagta
3001 gccatccttc acatcccgat catcaaacat gcatgtctaa gttgtgtgct ccacaaagcc
3061 aatctgcaac ttcaagctcc aggacatgtg gaaatacaaa gtgctcggac accaatagca
3121 agaattcttg ttattcacaa accaactctg aatcatgctc ttcaaagatg tctggtccat
3181 catgcaaaac tgctaattca ggttcaaggt catgcagaaa taagaagtgc caggactctg
3241 caaccgagaa cagttttcat tcaccactta ctaatccact cagtggggaa aagctttcgg
3301 agcagaaaag cttggattta gtccgaaaag ataaggaatc aagtcatgat cttcgtcatg
3361 gctgctctga cgaggaacat gatcatacaa atttagacaa ggcatatgac agttgtgcct
3421 tacaagaatg ttgttattcg gttcaaggca ataaaactga tgtatcagaa actggaatcc
3481 aggaaactgc tcattgtgac agcaccaatc aaacatgcca aactgcaagt tcaggatcga
3541 tgacatgcgg aaatgataag atcctggact ctctaagcat ccatggttgt cattcgcatg
3601 ataatccact ccacgaggag aacaacttgg agcagaaaat cttggatgtt gttggagaag
3661 gtataaaatc acctcatgct gtcggtcatg gctgttcgga caaggaacac gatcactcac
3721 atccagaaaa ggcatatgac agttgtgcaa cagatgattg ttgtttttca gttcaagtcc
3781 atggcattga cgacgtatca aaaagtgaaa ttcaagaaac tgctcattgt gacagcacaa
3841 agcagagcat ggtcatctcc agcagctgca aacatgaacc aaaagatcag gtaaatcact
3901 gtggacttca ctctaaaact actccaactg atgaagaact agccaagctg gttagaagat
3961 gctgcaaata caaaccatgc cacgacgtcc gttctggctg caggaagcat gctgcagaat
4021 gtggtccaac cgttcgatca accatcaata tcttacgagg caaccatcat cattacctag
4081 actgcagtgg tcgtaaggtt tgttcgctgt tggagaagag acacatcggt ggatgctgtg
4141 acagcttcag aaaagaatgt tgtgccaaga aaaacacctt ggagcaagt tttggaggag
4201 gtttatcaga aattgtcata gagtagatgc aatccgaagt gtacat
```

SEQ ID NO: 4
Polynucleotide sequence of *Nicotiana tabacum* heavy metal ATPase (NtHMA4.2)
GenBank Accession No: HF937054.1.

```
   1 atagaaagaa gagaatggtg gaaagtgaga aaatgaatga cacaaagaat ctgagcaaga
  61 gctattttga tgttttggga atttgctgta cttcagaagt tgttcttgtt gaaaaaattc
 121 tcaagaatct tgaagggtt aaagaggttt cagtaattgt cacaacaaag actgtcattg
 181 ttattcatga ttctctcctc atttctcagc aacaaattgt taagcattg aatcaagcaa
 241 gattagaagc aagtataaga gtgaaaggag agaaaaacta ccaaaagaaa tggccaagtc
 301 catttgcaat tggcagtgga atattgcttg gactctcatt tttgaagtac tttttttgcac
 361 ctttccaatg gttagcactt gcagctgttg cagttgggat tcctccaatt attttttaggg
 421 gtgtggctgc cgtgcgaaac ctcactcttg acatcaacat tcttgtttta atagcagtga
 481 cgggatcaat tgttttacac gattattggg aagctggtac tattgtcttc ttattcacca
 541 ttgcagaatg gctagagtca agggcaagtc acaaggctac tgctgctatg tcatcactgg
 601 tcaatatagt ccctccaaca gcagttttag ctgaaagtgg agaagtcgta aatgttgatg
 661 aagtcaagtt gaatagcatt cttgctgtta aagctggtga aactatacct attgatggag
 721 ttgtaatgga aggggaatgt gacgtggacg agaaaacact gacaggcgag tcgtttccag
 781 tttctaagca aatagattca acggtctggg ctggcactac aaatctaaat ggctatatca
 841 gtgttaagac tacggctttg gctgaagatt gtgcggtggc taggatggcg cagcttgtcg
 901 aagatgctca gaacaagaaa tcaaaaaccc aaagatact tgacaagtgt gctaaatatt
 961 atacaccagc aattgtggct atatcagctt cttttggcaat agttcctact gcattaagag
1021 ttcacaatcg aaatgagtgg tatcgcttgg ctttggtcac gttggtgagt gcatgtccgt
1081 gtgcacttgt gctatctaca ccagttgcca tgtgttgtgc actttctaaa gcagcaacgt
1141 ccggtcttct gtttaaagga gcagagtacc ttgagactct tgctaaaatc aaaatcatgg
1201 cttttgacaa aacagggact ataactagag gagaatttat ggtgaccgag ttcaagtctc
```

-continued

| | SEQUENCES | | | |
|---|---|---|---|---|
| 1261 | tggttgatgg | tcttggtctc | aatacactgc | tttactgggt ttcaagtatt gagagcaagt |
| 1321 | caggtcatcc | gatggcagcc | gctctggttg | actatgcaca atcaaattcc gttgagccaa |
| 1381 | agcctgatag | agttgagcag | tttcaaaatt | ttcctggtga agggatattt ggaagaattg |
| 1441 | atggaatgga | aatctatgtc | gggaatagga | aaattcttc aagagctgga tgtactacag |
| 1501 | taccagaaat | agagggtgat | agtttccaag | gaaagtctgt tggatacata ttttgggat |
| 1561 | catctcccgc | tggaattttc | ggtctttccg | atgtttgtcg aattggtgta aagaagcaa |
| 1621 | tgagagagct | gaagcagatg | ggtatcaaaa | ccgcgatgct tactggtgat tgtttatgcag |
| 1681 | ctgccaacca | tgtgcaggat | cagttaggtg | gagctatgga tgaatttcaa gcggaactct |
| 1741 | taccagagga | caaggcaaca | atcatcaagg | gttttcagaa ggaagctcca acagcgatga |
| 1801 | taggcgacgg | ccttaatgat | gctcctgcat | tagcaacagc tgacattggc atctcaatgg |
| 1861 | gcatctctgg | gtcagctctc | gcgaaagaaa | caggccatgt tatactaatg acaaatgaca |
| 1921 | tcggaagaat | accaaaagct | gcacgtcttg | ctagaagagt tcgaaggaag attgttgaga |
| 1981 | atatgattat | atcagtcgtt | acaaaggccg | ccatagttgc attggcaata gcaggttatc |
| 2041 | cattggtttg | ggctgctgtc | ctcgcggata | ctgggacatg cttgctagtg atcttgaaca |
| 2101 | gcatgctact | tctacgagta | ggcacacaca | gacatgggaa aaaatgttgt agatctgcta |
| 2161 | ctccttcgca | tgctcccaac | cacaaagaca | aagcttcttg ttgcaagtcg gaaaatgctc |
| 2221 | cgcagctgtg | ttgctctgat | attgagtcac | aaaagaaatg tacgagtcaa tcatgctcgt |
| 2281 | ccgaggtgtg | tgttccaaga | tgtcaacctg | tctcctcggg atcaaagtca tgtggaaata |
| 2341 | atcagtgccc | agactccgtt | gaaaatagtg | gttttcattc tcatcccgt cctcaatgct |
| 2401 | gctcgtcgaa | gatggcttct | aaagcatgcc | aatctgaatc ttcagaatca aagtcatgtg |
| 2461 | gaaataatca | gtgcccagac | tccgttgaaa | atagtggttt tcattctcat ccccgccctc |
| 2521 | aatgctgctc | gtctaagatg | gcttctaaag | catgccaatc tgcagttca gaatcaaagt |
| 2581 | catgtggaaa | taatcagtgc | ccagactccg | ttgaaaatag tggttttcat tctcatcccc |
| 2641 | gtcctcaatg | ctgctcgttg | aagatggctt | ctaaagcatg ccaatctgca gtttcagaat |
| 2701 | caaagtcatg | tggaaataat | cagtgcccag | actccgttga aaatagtggt tttcattctc |
| 2761 | atccccgtcc | tcaatgctgc | tcgtcgaaga | tggctgctaa agcatgccaa tctgcagttt |
| 2821 | cagaatcaaa | gtcatgtgga | ataacaatt | gctcggagtc catttacaag agtagttgtc |
| 2881 | attctttaac | aagttctcta | gtatgttctt | ccaagatgtc tgctcccaca tgtcattctg |
| 2941 | ccacttcaag | ctccaaatca | tgtggaagta | ccaagtgctc caacttcagt gacaaaaaat |
| 3001 | gttgccaata | tgacaaaatt | cctcaaacgt | gctctaccaa gaagtctgct ccaggatgtc |
| 3061 | aatctgcagt | ttctgggtct | aaatcatgtg | gagatagcaa gtgttcgac tcgaaagaca |
| 3121 | atagtagcca | tccttcacat | cccgatcatc | aaatatgcac gtctaagttg tgtgctccac |
| 3181 | aaagccaatc | tgcaacttca | agctccagga | catgtggaaa tatgaagtgc tcggacacca |
| 3241 | atagcaagaa | ttcttgttat | tcacatacca | actctgaatc atgctcttca aagatgtctg |
| 3301 | gtccagcatg | caaaactgct | aattcaggtt | caaggttatg cggaaataag aagtgcctag |
| 3361 | actctgcaaa | cgagaacagt | tttcattcac | ttactaatcc actctgtgag gaaaagcttt |
| 3421 | tggagaagga | aagcttggat | ttagcccgaa | aagtagggga atcaaatcat gatcttagtc |
| 3481 | atggttgctc | tgacgaggaa | catgatcatc | taaatttaga caaggcacat gacagttgtg |
| 3541 | ccttacaaga | atgttgttat | tctgttcaag | gcaataaaac tgatgtatca gaaactggaa |
| 3601 | tccaggaagc | tgctcattgt | gacagcatca | atcaaacatg ccaaactgca atttcaggat |
| 3661 | caatgacatg | cggaaataat | aagagtctgg | actctctaag catccatggt tgtcattcac |
| 3721 | atgatagtcc | actccacaag | gagagcaact | tggagcagaa aagcttggat gttgctggag |
| 3781 | aaggtataaa | atcacctcat | gctgtcggtc | aaggctgttc ggacaaggag cacaatcact |
| 3841 | cgcatccaga | aaaggcgtat | gacagttgtg | caacgacga ttgttgtttt tcagttcaag |
| 3901 | tccatggcat | tgacgacgta | tcaagaagtg | aaattcaaga aactgctcat tgtgacacga |
| 3961 | caaaacagag | cacggtcatc | cccagcagct | gcgaacatga accaaaagat caggtaaatc |
| 4021 | actgtggatc | tcactctaaa | agtattccaa | ctgatgaaga actagccaag ctggttagaa |
| 4081 | gatgctgcaa | atacaaacca | tgccacgatg | tccgctctgg ctgcaggaag catgctgcag |
| 4141 | aatgtggtcc | aaccgttcga | tcaaccatca | atatcttacg ggacaaccat catcatcatc |
| 4201 | tagactgcag | tggtcgtaag | gtttgttcgc | tgttgagaa gagacacatt ggtggatgct |
| 4261 | gtgacagctt | cagaaaagaa | tgttgtgcca | agaacaatca ccttggagca gttttggag |
| 4321 | gaggtttatc | agaaattgtc | atagagtaga | tgcaatctga agtgtacata tgttgt |

TABLE 1

| Mutation | Mutation denomination (WO'913) | Level of Cd in leaf (ppm) | % Cd reduction vs control | Level of Zn in leaf (ppm) | % Zn reduction vs control |
|---|---|---|---|---|---|
| Control | E3-277-Wild type | 92.3 ± 26.5 (mean ± SD, n = 4) | — | 92 | |
| R529* homozygous | E3-277 - Mutant (HMA-DT R342*) | 7.2 (mean, n = 2) | 92% | 62.3 | 32% |
| Control | BB16NN (Control) | ~560 | — | | |
| E387K homozygous | 276B5 (Hma-B E200K) | ~160 | ~71% | | |
| E387K homozygous | 276B8 (Hma-B E200K) | ~250 | ~55% | | |
| E387K homozygous | 276B18 (Hma-B E200K) | ~250 | ~55% | | |
| Control | 277S (Wild type) | 525.0 | — | | |
| R529* heterozygous | 277Htz (HMA-DT R342*) | 232.6 | 56% | | |

TABLE 1-continued

| Mutation | Mutation denomination (WO'913) | Level of Cd in leaf (ppm) | % Cd reduction vs control | Level of Zn in leaf (ppm) | % Zn reduction vs control |
|---|---|---|---|---|---|
| Control | 425S (Wild type) | 207.0 | — | | |
| W265* homozygous | 425M (Hma-AS W78*) | 36.1 | 83% | | |
| Control | 90S (Wild type) | 77.2 | — | | |
| L294F homozygous | 90M (HMA-AS L107F) | 25.7 | 67% | | |

Summary of Cd and Zn data in single HMA mutants as described in WO2012/041913A1. The denomination of the mutants in WO'913 differs from the mutant denomination herein and the mutants described in Hermand et al., 2014. This is due to the incomplete sequence used in WO'913. In the first column, the corresponding standard denomination is used.

TABLE 2

| Mutation | Level of Cd in shoots (ppm) | % Cd reduction vs the control | Level of Zn (ppm) | % Zn reduction vs the control |
|---|---|---|---|---|
| Control | ~135 | — | 2300 | — |
| P294S missense | ~50 | 63% | 2900 | 0% |
| E387K missense | ~70 | 48% | 1700 | 26% |
| W265* nonsense | ~50 | 63% | 1100 | 52% |
| G515R missense | ~70 | 48% | 2000 | 13% |
| R259* nonsense | ~60 | 56% | 1500 | 35% |

Summary of data reported in FIGS. 4a and 4c of Hermand et al. (2014) *Metallomics*. 6(8): 1427-1440

TABLE 3

Field trial 1 (moderate Cd region): Field data of single mutants

| Mutation | Control: Level of Cd in leaf (ppm) | Mutant: Level of Cd in leaf (ppm) | % Cd reduction in mut vs ctrl | p value | Control: Level of Zn in leaf (ppm) | Mutant: Level of Zn in leaf (ppm) | % Zn reduction in mut vs ctrl | p value |
|---|---|---|---|---|---|---|---|---|
| HMA4.1 W265* | 0.91 ± 0.1 | 0.92 ± 0.13 | 0% | 0.9731 | 19.2 ± 7.4 | 23.8 ± 6.3 | 0% | 0.9906 |
| HMA4.1 Q561* | 0.87 ± 0.11 | 1 ± 0.09 | 0% | 1.0000 | 18.6 ± 6.9 | 16.6 ± 4.7 | 11% | 0.9983 |
| HMA4.2 Q293* | 0.85 ± 0.13 | 0.89 ± 0.12 | 0% | 0.9997 | 18.9 ± 4.6 | 17.7 ± 3.7 | 6% | 0.9115 |
| HMA4.2 E296K | 0.89 ± 0.07 | 0.92 ± 0.1 | 0% | 0.9946 | 24.5 ± 15.8 | 13.4 ± 3.6 | 45% | 0.1779 |
| HMA4.2 T402I | 0.87 ± 0.09 | 0.93 ± 0.15 | 0% | 0.9984 | 21.9 ± 5.8 | 14.4 ± 1.6 | 34% | 0.0557 |
| HMA4.2 G251D | 0.88 ± 0.15 | 0.93 ± 0.07 | 0% | 0.9984 | 16 ± 3.9 | 15.1 ± 2.8 | 6% | 0.9700 |
| HMA4.2 G382R | 0.93 ± 0.06 | 0.93 ± 0.09 | 0% | 0.9995 | 14.8 ± 2.6 | 17.3 ± 5.7 | 0% | 0.9840 |
| HMA4.2 V351M | 0.83 ± 0.11 | 0.95 ± 0.12 | 0% | 0.9957 | 17.8 ± 5.4 | 14.2 ± 2 | 20% | 0.6459 |

Cd/Zn values (mean ± standard deviation) of pooled samples of plots of homozygous single mutants and their null-segregant controls grown in a large scale field experiment. % of Cd/Zn reduction is calculated compared to the control values. The p-value (paired T-test) is calculated for the probability that the mean (mutant line) is by chance <0.8 * mean (control line). For lines with significant >20% Cd/Zn reduction (p < 0.05), the p-values are highlighted in bold. In the field trial, for seven mutation combinations, the respective single mutants, double mutants and control plants were grown in six replicate plots (5 for Q293*/Q561*, 4 for E296/Q561* and 3 for Q293*/W265*). Each replicate unit contains 10 plants of the double mutant, the HMA4 WT control and the two simple mutants, respectively. As the mutations Q293* and Q561* occur in several combinations, the data for these single mutations are based on 8 and 33 plot values respectively. The single mutant plants do not show a biomass (leaf weight) reduction as compared to the control which can be seen in FIG. 6.

TABLE 4

Field trial 1 (moderate Cd region): Field data of double mutants

| Mutation combination (HMA4.1/HMA4.2) | Control: Level of Cd in leaf (ppm) | Mutant: Level of Cd in leaf (ppm) | % Cd reduction in mut vs ctrl | p value | Control: Level of Zn in leaf (ppm) | Mutant: Level of Zn in leaf (ppm) | % Zn reduction in mut vs ctrl | p value |
|---|---|---|---|---|---|---|---|---|
| Q293*/Q561* | 0.82 ± 0.15 | 0.058 ± 0.008 | 93% | 0 | 18.6 ± 3 | 12.9 ± 5.1 | 31% | 0.1204 |
| Q293*/W265* | 0.91 ± 0.1 | 0.069 ± 0.012 | 92% | 0.0013 | 19.2 ± 7.4 | 21.6 ± 20 | 0% | 0.6331 |
| E296K/Q561* | 0.89 ± 0.07 | 0.093 ± 0.104 | 90% | 0.0054 | 24.5 ± 15.8 | 12.1 ± 4.7 | 51% | 0.0377 |
| T402I/Q561* | 0.87 ± 0.09 | 0.042 ± 0.003 | 95% | 0 | 21.9 ± 5.8 | 10 ± 1.9 | 54% | 0.0043 |
| G251D/Q561* | 0.88 ± 0.15 | 0.59 ± 0.13 | 33% | 0.1029 | 16 ± 3.9 | 14 ± 2.6 | 13% | 0.9056 |
| G382R/Q561* | 0.93 ± 0.06 | 0.83 ± 0.07 | 11% | 0.9993 | 14.8 ± 2.6 | 15.6 ± 4.3 | 0% | 0.9990 |
| V351M/Q561* | 0.83 ± 0.11 | 0.91 ± 0.06 | 0% | 0.9994 | 17.8 ± 5.4 | 18.7 ± 5.1 | 0% | 0.9794 |

Figure 6:
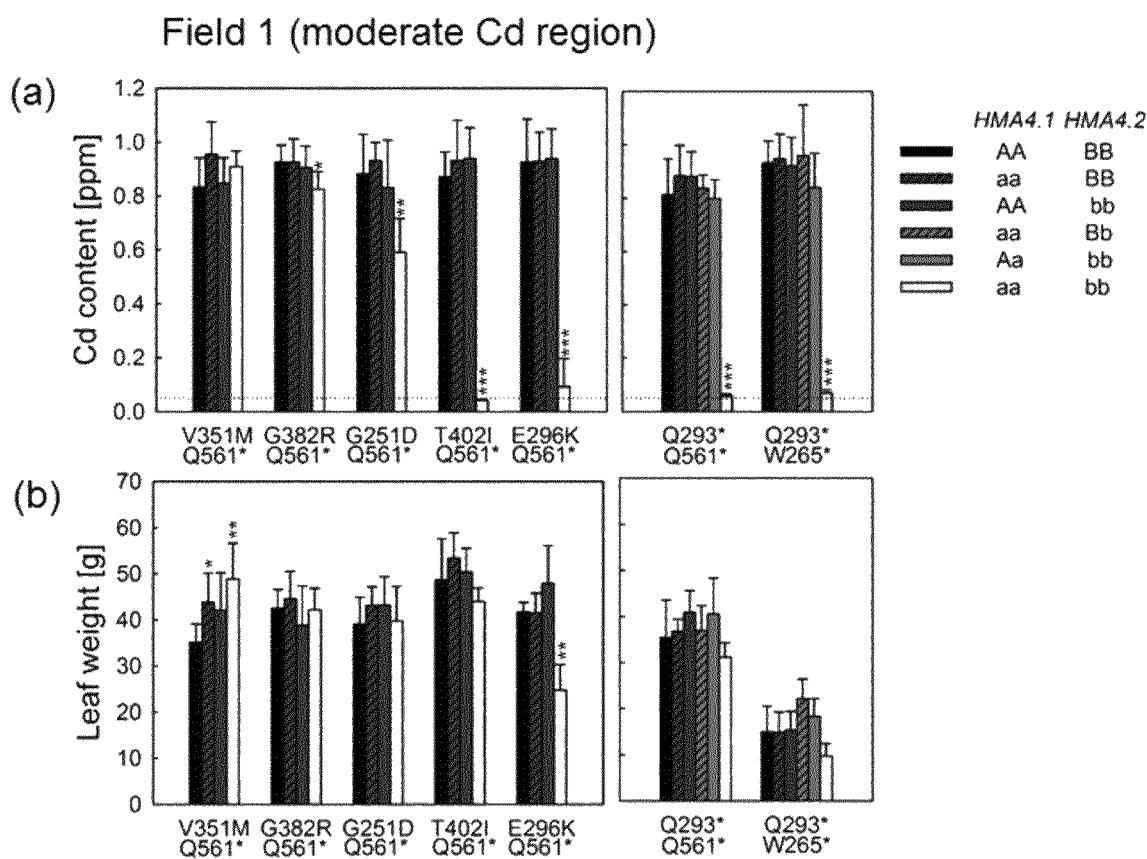
FIG. 6: (a) Leaf Cd and (b) leaf fresh weight data of the HMA4 mutants grown in the field in a region where a moderate Cd content is present. The genotype is indicated: A and a are the wild-type and mutant alleles for HMA4.1, B and b are wild-type and mutant alleles for HMA4.2. Leaf pooled samples were collected at lower stalk position in six (for some genotypes 3) replicated plots. Bars and error represent mean and standard deviation from 3-6 replicate plots measurements. *, , and * indicate levels of significance at P<0.05, P<0.01 and P<0.001, respectively, compared to the WT control plants. The dotted lines indicates LOQ=0.05 ppm for Cd measurement.

Cd/Zn values (mean ± standard deviation) of pooled samples of plots of homozygous double mutants and their null-segregant controls grown in a large scale field experiment. % of Cd/Zn reduction is calculated compared to the control values. The p-value (paired T-test) is calculated for the probability that the mean (mutant line) is by chance <0.8 * mean (control line). For lines with significant >20% Cd/Zn reduction (p < 0.05), the p-values are highlighted in bold. In the field trial, segregating seed lots of seven mutation combinations are sown and analysed for their genotype. For each mutation combination, four genotype groups are grown in six replicate plots (5 for Q293*/Q561*, 4 for E296/Q561* and 3 for Q293*/W265*). Each replicate unit contains 10 plants of the double mutant, the HMA4 WT control and the two simple mutants, respectively. Phenotypic data (leaf fresh weight) is shown in FIG. 6.

TABLE 5

Field trial 2 (moderate Cd region): Field data of double mutants

| Mutation combination (HMA4.1/HMA4.2) | Control: Level of Cd in leaf (ppm) | Mutant: Level of Cd in leaf (ppm) | % Cd reduction in mut vs ctrl | p value | Control: Level of Zn in leaf (ppm) | Mutant: Level of Zn in leaf (ppm) | % Zn reduction in mut vs ctrl | p value |
|---|---|---|---|---|---|---|---|---|
| Q293*/Q561* | 0.61 ± 0.07 | 0.064 ± 0.021 | 89% | 0 | 37.4 ± 5.5 | 13.7 ± 3.6 | 63% | 0.0007 |
| Q293*/W265* | 0.49 ± 0.12 | 0.058 ± 0.005 | 88% | 0.0007 | 33.5 ± 7.4 | 13.2 ± 1.7 | 61% | 0.0151 |
| Q464*/Q561* | 0.66 ± 0.07 | 0.043 ± 0.003 | 94% | 0 | 37.1 ± 7.5 | 9.4 ± 1.6 | 75% | 0 |
| Q293*/G235E | 0.64 ± 0.06 | 0.04 ± 0 | 94% | 0 | 33.7 ± 5.9 | 8.5 ± 1.8 | 75% | 0 |
| E296K/Q561* | 0.61 ± 0.12 | 0.047 ± 0.018 | 92% | 0 | 33.8 ± 6.9 | 10.7 ± 2.4 | 68% | 0.0002 |
| T402I/Q561* | 0.71 ± 0.14 | 0.041 ± 0.002 | 94% | 0 | 39.2 ± 5.3 | 9.3 ± 0.7 | 76% | 0 |
| G251D/Q561* | 0.74 ± 0.13 | 0.22 ± 0.06 | 70% | 0 | 34.5 ± 6.7 | 9.1 ± 1.1 | 74% | 0.0002 |
| Q293*/L223F | 0.61 ± 0.11 | 0.38 ± 0.09 | 37% | 0.0002 | 36.5 ± 5.6 | 25.4 ± 3.1 | 31% | 0.0118 |
| Q293*/D234N | 0.47 ± 0.03 | 0.34 ± 0.05 | 27% | 0.1494 | 30.5 ± 7.1 | 10.8 ± 0.8 | 65% | 0.0072 |
| A188V/Q561* | 0.58 ± 0.06 | 0.48 ± 0.1 | 17% | 0.5872 | 36.7 ± 6.5 | 34.9 ± 7.6 | 5% | 0.9866 |
| G382R/Q561* | 0.65 ± 0.12 | 0.56 ± 0.07 | 14% | 0.8572 | 36.8 ± 6.4 | 35.2 ± 5.8 | 4% | 0.9997 |
| Q293*/A369V | 0.46 ± 0.04 | 0.4 ± 0.05 | 14% | 0.9007 | 33.3 ± 4.3 | 32 ± 4.1 | 4% | 0.9929 |
| Q293*/A374V | 0.47 ± 0.07 | 0.43 ± 0.06 | 9% | 0.9645 | 36.5 ± 7.9 | 31.9 ± 4.8 | 12% | 0.958 |
| V351M/Q561* | 0.66 ± 0.05 | 0.63 ± 0.06 | 6% | 0.9823 | 34.1 ± 5.2 | 32.9 ± 4.7 | 4% | 0.9999 |
| T189I/Q561* | 0.69 ± 0.09 | 0.67 ± 0.11 | 3% | 0.9829 | 40.8 ± 4.4 | 45.3 ± 7.2 | 0% | 1 |
| Q293*/S27L | 0.58 ± 0.09 | 0.61 ± 0.06 | 0% | 0.9996 | 32.8 ± 5.2 | 34.8 ± 7.7 | 0% | 0.9977 |
| Q293*/A188V | 0.48 ± 0.07 | 0.51 ± 0.08 | 0% | 0.9999 | 30.6 ± 7.7 | 29.8 ± 3.4 | 3% | 0.9761 |
| G128E/Q561* | 0.71 ± 0.08 | 0.85 ± 0.15 | 0% | 0.9997 | 36.4 ± 7.4 | 31.1 ± 5.2 | 15% | 0.9737 |

Cd/Zn values (mean ± standard deviation) of pooled samples of plots of homozygous double mutants and their null-segregant controls grown in a large scale field experiment. % of Cd/Zn reduction is calculated compared to the control values. The p-value (paired T-test) is calculated for the probability that the mean (mutant line) is by chance <0.8 * mean (control line). For lines with significant >20% Cd/Zn reduction (p < 0.05), the p-values are highlighted in bold. In the field trial, for 18 mutation combinations, double mutants and their control plants were grown in six replicate plots (4 for Q293*/W265* and for Q293*/D234N). Each replicate unit contained 20 plants of the double mutant and the HMA4 WT control, respectively. Phenotypic data (leaf dry weight) is shown in FIG. 7.

TABLE 6

Field data of field trials 3 and 4: high Cd regions

| Mutation combination (HMA4.1/HMA4.2) | Control: Level of Cd in leaf (ppm) | Mutant: Level of Cd in leaf (ppm) | % Cd reduction in mut vs ctrl | p value | Control: Level of Zn in leaf (ppm) | Mutant: Level of Zn in leaf (ppm) | % Zn reduction in mut vs ctrl | p value |
|---|---|---|---|---|---|---|---|---|
| *Field 3: high Cd region 1* | | | | | | | | |
| Q293*/Q561* | 3.05 ± 0.71 | 0.61 ± 0.24 | 80% | 0.0003 | 94.8 ± 15.5 | 22.9 ± 5.7 | 76% | 0.0000 |
| Q293*/G235E | 3.49 ± 0.79 | 0.58 ± 0.26 | 84% | 0.0003 | 114.3 ± 19.1 | 21.8 ± 5.1 | 81% | 0.0000 |
| E296K/Q561* | 3.09 ± 0.82 | 0.4 ± 0.19 | 87% | 0.0001 | 112.7 ± 22.8 | 20.1 ± 4.5 | 82% | 0.0000 |
| T402I/Q561* | 2.38 ± 0.8 | 0.47 ± 0.16 | 80% | 0.0009 | 81.9 ± 9.7 | 20.8 ± 2.5 | 75% | 0.0001 |
| G251D/Q561* | 2.89 ± 0.75 | 1.56 ± 0.38 | 46% | 0.0014 | 107 ± 18.6 | 25.3 ± 4.6 | 76% | 0.0000 |
| *Field 4: high Cd region 2* | | | | | | | | |
| Q293*/Q561* | 2.65 ± 2.52 | 0.16 ± 0.08 | 94% | 0.0068 | 32.1 ± 10.7 | 11.4 ± 1.1 | 65% | 0.0303 |
| Q293*/G235E | 3.81 ± 2.88 | 0.18 ± 0.04 | 95% | 0.0006 | 38 ± 8.2 | 12.3 ± 1.6 | 68% | 0.0018 |
| E296K/Q561* | 2.9 ± 2.5 | 0.13 ± 0.02 | 96% | 0.0009 | 36.3 ± 8.6 | 14.5 ± 1.6 | 60% | 0.0052 |

TABLE 6-continued

Field data of field trials 3 and 4: high Cd regions

| Mutation combination (HMA4.1/ HMA4.2) | Control: Level of Cd in leaf (ppm) | Mutant: Level of Cd in leaf (ppm) | % Cd reduction in mut vs ctrl | p value | Control: Level of Zn in leaf (ppm) | Mutant: Level of Zn in leaf (ppm) | % Zn reduction in mut vs ctrl | p value |
|---|---|---|---|---|---|---|---|---|
| T402I/Q561* | 2.81 ± 1.98 | 0.27 ± 0.11 | 90% | 0.0001 | 30.7 ± 9.2 | 16.4 ± 2.7 | 47% | 0.0439 |
| G251D/Q561* | 4.01 ± 1.84 | 2.27 ± 0.97 | 43% | 0.0056 | 38.8 ± 10.6 | 14.2 ± 1.8 | 63% | 0.0107 |

Cd/Zn values (mean ± standard deviation) of pooled samples of plots of homozygous double mutants and their null-segregant controls grown in a two field experiments in high cadmium regions. % of Cd/Zn reduction is calculated compared to the control values. The p-value (paired T-test) is calculated for the probability that the mean (mutant line) is by chance <0.8 * mean (control line). For lines with significant >20% Cd/Zn reduction (p < 0.05), the p-values are highlighted in bold. In the field trial, for five mutation combinations, double mutants and their control plants were grown in five replicate plots. Each replicate unit contained 20 plants of the double mutant and the HMA4 WT control, respectively. Only plots with acceptable growth for both mutant and control were analysed (5 plots for most lines, except: in field 3: 4 plots for T402I/Q561*; in field 4: 4 plots for G251D/Q561* and 3 plots for Q293*/Q561*). Phenotypic data (cured leaf weight) is shown in FIG. 8.

TABLE 7

| Amino acid residues | Length (amino acids) | Description |
|---|---|---|
| 1-90 | 90 | Cytoplasmic N-terminal sequence (HMA domain) |
| 91-112 | 22 | Transmembrane domain 1 |
| 113-115 | 3 | Extracellular sequence |
| 116-135 | 20 | Transmembrane domain 2 |
| 136-142 | 7 | first cytoplasmic loop |
| 143-163 | 21 | Transmembrane domain 3 |
| 164-164 | 1 | Extracellular sequence |
| 165-183 | 21 | Transmembrane domain 4 |
| 186-311 | 126 | second cytoplasmic loop (A-domain) |
| 312-334 | 23 | Transmembrane domain 5 |
| 335-342 | 8 | Extracellular sequence |
| 343-360 | 18 | Transmembrane domain 6 |
| 361-653 | 293 | third cytoplasmic loop (P-domain and N-domain) |
| 654-673 | 20 | Transmembrane domain 7 |
| 674-677 | 4 | Extracellular sequence |
| 678-697 | 20 | Transmembrane domain 8 |
| 698-1403 (HMA4.1)/ 1444 (HMA4.2) | 706 (HMA4.1)/ 747(HMA4.2) | Cytoplasmic C-terminal sequence |

The domain structure of HMA4 was deduced from sequence alignments with the *Arabidopsis* HMA2 and HMA4 proteins and their respective domain annotation by UniProt (AtHMA2: Q9SZW4; AtHMA4: O64474).

TABLE 8

Greenhouse data of selected double mutants

| Mutation combination | Level of Cd in leaf (ppm) | % Cd reduction vs control | Level of Zn in leaf (ppm) | % Zn reduction vs control |
|---|---|---|---|---|
| Control | 0.66 ± 0.24 | — | 32.5 ± 12.1 | — |
| Q293*/Q561* | 0.059 ± 0.015 | 91% | 10.7 ± 3.43 | 67% |
| E296K/Q561* | 0.051 ± 0.003 | 92% | 8.18 ± 2.61 | 75% |
| T402I/Q561* | 0.077 ± 0.016 | 88% | 7.99 ± 1.20 | 75% |
| G251D/Q561* | 0.42 ± 0.12 | 37% | 15.3 ± 13.2 | 53% |
| G382R/Q561* | 0.55 ± 0.13 | (17%) | 22.5 ± 5.77 | 31% |
| V351M/Q56* | 0.53 ± 0.15 | (19%) | 19.8 ± 4.60 | 39% |

Cd/Zn values (mean ± standard deviation) of eight plants (six plants for Q293*/A374V) that are homozygous double mutants (mutations indicated as "homozygous mutation in HMA4.1/homozygous mutation in HMA4.2") and the null-segregant controls of all double mutants (54 plants total). % of Cd/Zn reduction are calculated compared to the control values. In order to make the table less complex, all 54 control plants are analysed together in the above table and the Cd/Zn values of the double mutant plots are compared with all controls. (T-tests are performed and values in brackets indicate no significant reduction at P < 0.05.) Plants in this experiment are grown in large pots in the greenhouse. Plant morphology and yield analysed after four and eleven weeks of growth in pots are indicated.

TABLE 9

Greenhouse data of further selected double mutants

| Mutation Combination | Level of Cd in leaf (ppm) | % Cd reduction vs control | Level of Zn in leaf (ppm) | % Zn reduction vs control |
|---|---|---|---|---|
| Control | 0.31 ± 0.09 | — | 33.9 ± 4.57 | — |
| H438Y/W265* | 0.13 ± 0.06 | 58% | 12.2 ± 2.4 | 64% |
| L36F/Q561* | 0.38 ± 0.16 | 0% | 28.8 ± 5.34 | 15% |

Leaf Cd/Zn values (mean ± standard deviation of 9 replicate plants for H438Y/W265* and of 6 replicate plants for L36F/Q561*) of two additional combinations of homozygous HMA4 mutants (mutations indicated as "homozygous mutation in HMA4.1/homozygous mutation in HMA4.2") and the same number of null-segregant controls for each double mutant. % of Cd/Zn reduction are calculated compared to the control values.

TABLE 10

| Exon | AA change | WT SIFT score | Mut. SIFT score | Mut. SIFT/ WT SIFT |
|---|---|---|---|---|
| HMA4.1- Ex 1 | S16R | 1 | 0.022 | 0.022 |
| HMA4.1- Ex 1 | V30I | 0.454 | 0.074 | 0.164 |
| HMA4.1- Ex 1 | L36F | 1 | 0.003 | 0.003 |
| HMA4.1- Ex 1 | E44K | 1 | 0.291 | 0.291 |
| HMA4.1- Ex 1 | T50I | 0.277 | 0.066 | 0.238 |
| HMA4.1- Ex 2 | E78K | 1 | 0.167 | 0.167 |
| HMA4.1- Ex 2 | A98V | 1 | 0.540 | 0.540 |
| HMA4.1- Ex 2 | G128E | 1 | 0.029 | 0.029 |
| HMA4.1- Ex 2 | P130L | 0.095 | 0.281 | 2.948 |
| HMA4.1- Ex 2 | A138V | 1 | 0.184 | 0.184 |
| HMA4.1- Ex 4/5 | A188V | 1 | 0.004 | 0.004 |
| HMA4.1- Ex 4/5 | T189I | 1 | 0.015 | 0.015 |
| HMA4.1- Ex 4/5 | A191T | 1 | 0.093 | 0.093 |
| HMA4.1- Ex 4/5 | V217I | 1 | 0.280 | 0.280 |
| HMA4.1- Ex 4/5 | G251D | 1 | 0 | 0 |
| HMA4.1- Ex 4/5 | A266T | 1 | 0.005 | 0.005 |
| HMA4.1- Ex 4/5 | A287V | 0.635 | 1 | 1.575 |
| HMA4.1- Ex 4/5 | Q293* | | | STOP |
| HMA4.1- Ex 4/5 | E296K | 1 | 0 | 0 |
| HMA4.1- Ex 4/5 | C312Y | 1 | 0.348 | 0.348 |
| HMA4.1- Ex 6 | T349I | 0.153 | 0.101 | 0.658 |
| HMA4.1- Ex 6 | V351M | 1 | 0.003 | 0.003 |
| HMA4.1- Ex 6 | S376F | 1 | 0.017 | 0.017 |
| HMA4.1- Ex 6 | G382R | 1 | 0.002 | 0.002 |
| HMA4.1- Ex 6 | T402I | 1 | 0 | 0 |
| HMA4.1- Ex 6 | E407K | 1 | 0.340 | 0.340 |
| HMA4.1- Ex 7/8 | S434N | 1 | 0.018 | 0.018 |
| HMA4.1- Ex 7/8 | G437S | 0.161 | 1 | 6.219 |
| HMA4.1- Ex 7/8 | H438Y | 1 | 0 | 0 |
| HMA4.1- Ex 7/8 | A448T | 1 | 0.003 | 0.003 |
| HMA4.1- Ex 7/8 | Q464* | | | STOP |
| HMA4.1- Ex 7/8 | R474K | 0.366 | 1 | 2.731 |
| HMA4.1- Ex 7/8 | M478I | 0.243 | 0.028 | 0.117 |
| HMA4.1- Ex 7/8 | T494I | 0.651 | 0.145 | 0.222 |
| HMA4.1- Ex 7/8 | V496I | 1 | 0.181 | 0.181 |
| HMA4.1- Ex 7/8 | H559Y | 1 | 0.429 | 0.429 |
| HMA4.2- Ex 1 | M7I | 0.377 | 0.359 | 0.954 |
| HMA4.2- Ex 1 | D19N | 1 | 0.008 | 0.008 |

TABLE 10-continued

| Exon | AA change | WT SIFT score | Mut. SIFT score | Mut. SIFT/ WT SIFT |
|---|---|---|---|---|
| HMA4.2- Ex 1 | S27L | 1 | 0.018 | 0.018 |
| HMA4.2- Ex 1 | L31F | 1 | 0.028 | 0.028 |
| HMA4.2- Ex 1 | L62F | 1 | 0.033 | 0.033 |
| HMA4.2- Ex 2 | G106E | 0.513 | 0.238 | 0.465 |
| HMA4.2- Ex 2 | L145F | 1 | 0.165 | 0.165 |
| HMA4.2- Ex 4/5 | A188V | 1 | 0.003 | 0.003 |
| HMA4.2- Ex 4/5 | P200L | 1 | 0.005 | 0.005 |
| HMA4.2- Ex 4/5 | S221N | 0.545 | 0.096 | 0.176 |
| HMA4.2- Ex 4/5 | L223F | 1 | 0.019 | 0.019 |
| HMA4.2- Ex 4/5 | A224V | 1 | 0.152 | 0.152 |
| HMA4.2- Ex 4/5 | D234N | 1 | 0 | 0 |
| HMA4.2- Ex 4/5 | G235E | 1 | 0.001 | 0.001 |
| HMA4.2- Ex 4/5 | G251D | 1 | 0 | 0 |
| HMA4.2- Ex 4/5 | W265\* | | | STOP |
| HMA4.2- Ex 6 | P331T | 0.120 | 0.038 | 0.318 |
| HMA4.2- Ex 6 | P331S | 0.120 | 0.019 | 0.154 |
| HMA4.2- Ex 6 | T349M | 0.286 | 0.021 | 0.075 |
| HMA4.2- Ex 6 | V364V | 1 | 0.089 | 0.089 |
| HMA4.2- Ex 6 | A369V | 1 | 0.001 | 0.001 |
| HMA4.2- Ex 6 | A374V | 1 | 0.008 | 0.008 |
| HMA4.2- Ex 6 | G419D | 0.583 | 1 | 1.715 |
| HMA4.2- Ex 7/8 | S452F | 1 | 0.005 | 0.005 |
| HMA4.2- Ex 7/8 | D476Y | 1 | 0.001 | 0.001 |
| HMA4.2- Ex 7/8 | G506R | 1 | 0.006 | 0.006 |
| HMA4.2- Ex 7/8 | V509F | 1 | 0.057 | 0.057 |
| HMA4.2- Ex 7/8 | G510E | 1 | 0.401 | 0.401 |
| HMA4.2- Ex 7/8 | P518S | 0.459 | 0.187 | 0.407 |
| HMA4.2- Ex 7/8 | A519V | 1 | 0.562 | 0.562 |
| HMA4.2- Ex 7/8 | G523S | 1 | 0.759 | 0.759 |
| HMA4.2- Ex 7/8 | T546I | 1 | 0.061 | 0.061 |
| HMA4.2- Ex 7/8 | Q561\* | | | STOP |

List of identified and validated mutations in HMA4.1 and HMA4.2. Amino acid changes are indicated and the corresponding SIFT scores. Interesting mutations are highlighted in bold (nonsense mutation or missense mutation with SIFT score of the substituted aa <0.05 of the original SIFT score.

TABLE 11

Examples of mutation combinations expected to reduce Cd content in leaf

| Other possible combinations | Mutation in HMA4.1 | Mutation in HMA4.2 |
|---|---|---|
| Combination 1 | Q464* | W265* |
| Combination 2 | Q464* | L223F |
| Combination 3 | Q464* | D234N |
| Combination 4 | Q464* | G235E |
| Combination 5 | E296K | W265* |
| Combination 6 | E296K | L223F |
| Combination 7 | E296K | D234N |
| Combination 8 | E296K | G235E |
| Combination 9 | T402I | W265* |
| Combination 10 | T402I | L223F |
| Combination 11 | T402I | D234N |
| Combination 12 | T402I | G235E |
| Combination 13 | G251D | W265* |
| Combination 14 | G251D | L223F |
| Combination 15 | G251D | D234N |
| Combination 16 | G251D | G235E |
| Combination 17 | H438Y | Q561* |
| Combination 18 | H438Y | L223F |
| Combination 19 | H438Y | D234N |
| Combination 20 | H438Y | G235E |

TABLE 12

Examples of mutation combinations expected to reduce Cd content in leaf

| Other possible combinations | Mutation in HMA4.2 | Mutation in HMA4.1 |
|---|---|---|
| Combination 1 | Q464* | W265* |
| Combination 2 | Q464* | L223F |
| Combination 3 | Q464* | D234N |
| Combination 4 | Q464* | G235E |
| Combination 5 | E296K | W265* |
| Combination 6 | E296K | L223F |
| Combination 7 | E296K | D234N |
| Combination 8 | E296K | G235E |
| Combination 9 | T402I | W265* |
| Combination 10 | T402I | L223F |
| Combination 11 | T402I | D234N |
| Combination 12 | T402I | G235E |
| Combination 13 | G251D | W265* |
| Combination 14 | G251D | L223F |
| Combination 15 | G251D | D234N |
| Combination 16 | G251D | G235E |
| Combination 17 | H438Y | Q561* |
| Combination 18 | H438Y | L223F |
| Combination 19 | H438Y | D234N |
| Combination 20 | H438Y | G235E |

The invention claimed is:

1. A non-naturally occurring and genetically modified plant or an artificially induced non-naturally occurring mutant plant or part thereof, having at least partially reduced expression or activity of at least two heavy metal ATPase (HMA) polypeptides encoded by at least two polynucleotide sequences, wherein said at least two polynucleotide sequences are selected from the group consisting of: (i) a polynucleotide sequences encoding a HMA polypeptides comprising an amino acid sequence having at least 95% amino acid sequence identity to the amino acid sequence as set forth in SEQ ID NO: 1, and a polynucleotide sequence encoding a HMA polypeptide comprising an amino acid sequence having at least 95% amino acid sequence identity to the amino acid sequence as set forth in SEQ ID NO: 2 and (ii) a polynucleotide sequences having at least 90% nucleotide sequence identity to the nucleotide sequence as set forth in SEQ ID NO: 3 and encoding a HMA polypeptide having at least 95% amino acid sequence identity to the amino acid sequence as set forth in SEQ ID NO: 1, and a polynucleotide sequence having at least 90% nucleotide sequence identity to the nucleotide sequence as set forth in SEQ ID NO: 4 and encoding a HMA polypeptide having at least 95% amino acid sequence identity to the amino acid sequence as set forth in SEQ ID NO: 2, and wherein said at least partially reduced expression or activity is by artificial mutagenesis or inhibitory RNAi construct mediated transformation of corresponding wild type plant or part thereof of the same species, wherein said non-naturally occurring and genetically modified plant or said artificially induced non-naturally occurring mutant plant or part thereof exhibits at least a 27% reduction in the accumulation of cadmium levels in leaf tissues of said non-naturally occurring and genetically modified plant or said artificially induced non-naturally occurring mutant plant or part thereof as compared to said corresponding wild type plant or part thereof of the same species and grown under identical growth conditions, wherein said non-naturally occurring and genetically modified plant or said artificially induced non-naturally occurring mutant plant or part thereof is grown under field conditions in the presence of cadmium, and wherein said non-naturally occurring and genetically modified plant or said artificially induced non-naturally occurring mutant plant or part thereof when grown under said field conditions in the presence of cadmium exhibits normal growth and development, and seed set which is identical and comparable to a wild type plant or part thereof of the same species grown under cadmium free conditions, and as compared to a hydroponically grown plant having said reduced expression or activity of said at least two heavy metal ATPase (HMA) polypeptides grown under said cadmium, and which shows stunted growth and does not produce seeds.

2. The non-naturally occurring genetically modified plant or said artificially induced non-naturally occurring mutant plant or part thereof according to claim 1, wherein the expression or activity of one of the ATPase (HMA) polypeptides set forth in (i) or (ii) is lost as compared to the corresponding wild type plant or part thereof.

3. The non-naturally occurring genetically modified plant or said artificially induced non-naturally occurring mutant plant or part thereof according to claim 1, wherein the phenotype of said non-naturally occurring genetically modified plant or said artificially induced non-naturally occurring mutant plant or part thereof at harvest time is the same as the corresponding wild type plant or part thereof at the same harvest time, wherein said non-naturally occurring genetically modified plant or said artificially induced non-naturally occurring mutant plant or part thereof does not show a biomass reduction at harvest time as compared to the corresponding wild type plant or part thereof at the same harvest time.

4. The non-naturally occurring genetically modified plant or said artificially induced non-naturally occurring mutant plant or part thereof according to claim 1, comprising at least one mutation in coding sequences of polynucleotide sequences as set forth in (i) or (ii).

5. The non-naturally occurring genetically modified plant or said artificially induced non-naturally occurring mutant plant or part thereof according to claim 1, comprising one or more of the following groups of mutations:

at least one mutation at a position corresponding to an amino acid position in the A-domain of the second cytoplasmic loop of the HMA polypeptide encoded by the non-mutated sequence set forth in SEQ ID NO: 3 and at least one mutation at a position corresponding to an amino acid position in the P/N-domain of the third cytoplasmic loop of the HMA polypeptide encoded by the non-mutated sequence set forth in SEQ ID NO: 4;

at least one mutation at a position corresponding to an amino acid position in the A-domain of the second cytoplasmic loop of the HMA polypeptide encoded by the non-mutated sequence set forth in SEQ ID NO: 3 and at least one mutation at a position corresponding to an amino acid position in the A-domain of the second cytoplasmic loop of the HMA polypeptide encoded by the non-mutated sequence set forth in SEQ ID NO: 4;

at least one mutation at a position corresponding to an amino acid position in the P/N-domain of the third cytoplasmic loop of the HMA polypeptide encoded by the non-mutated sequence set forth in SEQ ID NO: 3 and at least one mutation at a position corresponding to an amino acid position in the P/N-domain of the third cytoplasmic loop of the HMA polypeptide encoded by the non-mutated sequence set forth in SEQ ID NO: 4; and at least one mutation at a position corresponding to an amino acid position in the P/N-domain of the third cytoplasmic loop of the HMA polypeptide encoded by the non-mutated sequence set forth in SEQ ID NO: 3 and at least one mutation at a position corresponding to an amino acid position in the A-domain of the second cytoplasmic loop of the HMA polypeptide encoded by the non-mutated sequence set forth in SEQ ID NO: 4.

6. The non-naturally occurring genetically modified plant or said artificially induced non-naturally occurring mutant plant or part thereof according to claim 1 comprising one or more of the following groups of mutations:

a nonsense mutation at a position corresponding to amino acid position 293 of SEQ ID NO: 1 and a nonsense mutation at a position corresponding to amino acid position 561 of the non-mutated sequence set forth in SEQ ID NO: 2;

a nonsense mutation at a position corresponding to amino acid position 293 of SEQ ID NO: 1 and a nonsense mutation at a position corresponding to amino acid position 265 of the non-mutated sequence set forth in SEQ ID NO: 2;

a missense mutation at a position corresponding to amino acid position 296 of SEQ ID NO: 1 and a nonsense mutation at a position corresponding to amino acid position 561 of the non-mutated sequence set forth in SEQ ID NO: 2;

a missense mutation at a position corresponding to amino acid position 402 of SEQ ID NO: 1 and a nonsense mutation at a position corresponding to amino acid position 561 of the non-mutated sequence set forth in SEQ ID NO: 2;

a missense mutation at a position corresponding to amino acid position 251 of SEQ ID NO: 1 and a nonsense mutation at a position corresponding to amino acid position 561 of the non-mutated sequence set forth in SEQ ID NO: 2;

a nonsense mutation at a position corresponding to amino acid position 464 of SEQ ID NO: 1 and a nonsense mutation at a position corresponding to amino acid position 561 of the non-mutated sequence set forth in SEQ ID NO: 2;

a nonsense mutation at a position corresponding to amino acid position 293 of SEQ ID NO: 1 and a missense mutation at a position corresponding to amino acid position 223 of the non-mutated sequence set forth in SEQ ID NO: 2;

a nonsense mutation at a position corresponding to amino acid position 293 of SEQ ID NO: 1 and a missense mutation at a position corresponding to amino acid position 234 of the non-mutated sequence set forth in SEQ ID NO: 2;

a nonsense mutation at a position corresponding to amino acid position 293 of SEQ ID NO: 1 and a missense mutation at a position corresponding to amino acid position 235 of the non-mutated sequence set forth in SEQ ID NO: 2;

a missense mutation at a position corresponding to amino acid position 438 of SEQ ID NO: 1 and a nonsense mutation at a position corresponding to amino acid position 265 of the non-mutated sequence set forth in SEQ ID NO: 2;

a nonsense mutation at a position corresponding to amino acid position 464 of SEQ ID NO: 1 and a nonsense mutation at a position corresponding to amino acid position 265 of SEQ ID NO: 2;

a nonsense mutation at a position corresponding to amino acid position 464 of SEQ ID NO: 1 and a missense mutation at a position corresponding to amino acid position 223 of SEQ ID NO: 2;

a nonsense mutation at a position corresponding to amino acid position 464 of SEQ ID NO: 1 and a missense mutation at a position corresponding to amino acid position 234 of SEQ ID NO: 2;

a nonsense mutation at a position corresponding to amino acid position 464 of SEQ ID NO: 1 and a missense mutation at a position corresponding to amino acid position 235 of SEQ ID NO: 2;

a missense mutation at a position corresponding to amino acid position 296 of SEQ ID NO: 1 and a nonsense mutation at a position corresponding to amino acid position 265 of SEQ ID NO: 2;

a missense mutation at a position corresponding to amino acid position 296 of SEQ ID NO: 1 and a missense mutation at a position corresponding to amino acid position 223 of SEQ ID NO: 2;

a missense mutation at a position corresponding to amino acid position 296 of SEQ ID NO: 1 and a missense mutation at a position corresponding to amino acid position 234 of SEQ ID NO: 2;

a missense mutation at a position corresponding to amino acid position 296 of SEQ ID NO: 1 and a missense mutation at a position corresponding to amino acid position 235 of SEQ ID NO: 2;

a missense mutation at a position corresponding to amino acid position 402 of SEQ ID NO: 1 and a nonsense mutation at a position corresponding to amino acid position 265 of SEQ ID NO: 2;

a missense mutation at a position corresponding to amino acid position 402 of SEQ ID NO: 1 and a missense mutation at a position corresponding to amino acid position 223 of SEQ ID NO: 2;

a missense mutation at a position corresponding to amino acid position 402 of SEQ ID NO: 1 and a missense mutation at a position corresponding to amino acid position 234 of SEQ ID NO: 2;

a missense mutation at a position corresponding to amino acid position 402 of SEQ ID NO: 1 and a missense mutation at a position corresponding to amino acid position 235 of SEQ ID NO: 2;

a missense mutation at a position corresponding to amino acid position 251 of SEQ ID NO: 1 and a nonsense mutation at a position corresponding to amino acid position 265 of SEQ ID NO: 2;

a missense mutation at a position corresponding to amino acid position 251 of SEQ ID NO: 1 and a missense mutation at a position corresponding to amino acid position 223 of SEQ ID NO: 2;

a missense mutation at a position corresponding to amino acid position 251 of SEQ ID NO: 1 and a missense mutation at a position corresponding to amino acid position 234 of SEQ ID NO: 2;

a missense mutation at a position corresponding to amino acid position 251 of SEQ ID NO: 1 and a missense mutation at a position corresponding to amino acid position 235 of SEQ ID NO: 2;

a missense mutation at a position corresponding to amino acid position 438 of SEQ ID NO: 1 and a nonsense mutation at a position corresponding to amino acid position 561 of SEQ ID NO: 2;

a missense mutation at a position corresponding to amino acid position 438 of SEQ ID NO: 1 and a missense mutation at a position corresponding to amino acid position 223 of SEQ ID NO: 2;

a missense mutation at a position corresponding to amino acid position 438 of SEQ ID NO: 1 and a missense mutation at a position corresponding to amino acid position 234 of SEQ ID NO: 2;

a missense mutation at a position corresponding to amino acid position 438 of SEQ ID NO: 1 and a missense mutation at a position corresponding to amino acid position 235 of SEQ ID NO: 2;

a nonsense mutation at a position corresponding to amino acid position 293 of SEQ ID NO: 2 and a nonsense mutation at a position corresponding to amino acid position 561 of the non-mutated sequence set forth in SEQ ID NO: 1;

a nonsense mutation at a position corresponding to amino acid position 293 of SEQ ID NO: 2 and a nonsense mutation at a position corresponding to amino acid position 265 of the non-mutated sequence set forth in SEQ ID NO: 1;

a missense mutation at a position corresponding to amino acid position 296 of SEQ ID NO: 2 and a nonsense mutation at a position corresponding to amino acid position 561 of the non-mutated sequence set forth in SEQ ID NO: 1;

a missense mutation at a position corresponding to amino acid position 402 of SEQ ID NO: 2 and a nonsense mutation at a position corresponding to amino acid position 561 of the non-mutated sequence set forth in SEQ ID NO: 1;

a missense mutation at a position corresponding to amino acid position 251 of SEQ ID NO: 2 and a nonsense mutation at a position corresponding to amino acid position 561 of the non-mutated sequence set forth in SEQ ID NO: 1;

a nonsense mutation at a position corresponding to amino acid position 464 of SEQ ID NO: 2 and a nonsense mutation at a position corresponding to amino acid position 561 of the non-mutated sequence set forth in SEQ ID NO: 1;

a nonsense mutation at a position corresponding to amino acid position 293 of SEQ ID NO: 2 and a missense mutation at a position corresponding to amino acid position 223 of the non-mutated sequence set forth in SEQ ID NO: 1;

a nonsense mutation at a position corresponding to amino acid position 293 of SEQ ID NO: 2 and a missense mutation at a position corresponding to amino acid position 234 of the non-mutated sequence set forth in SEQ ID NO: 1;

a nonsense mutation at a position corresponding to amino acid position 293 of SEQ ID NO: 2 and a missense mutation at a position corresponding to amino acid position 235 of the non-mutated sequence set forth in SEQ ID NO: 1;

a missense mutation at a position corresponding to amino acid position 438 of SEQ ID NO: 2 and a nonsense mutation at a position corresponding to amino acid position 265 of the non-mutated sequence set forth in SEQ ID NO: 1;

a nonsense mutation at a position corresponding to amino acid position 464 of SEQ ID NO: 2 and a nonsense mutation at a position corresponding to amino acid position 265 of SEQ ID NO: 1;

a nonsense mutation at a position corresponding to amino acid position 464 of SEQ ID NO: 2 and a missense mutation at a position corresponding to amino acid position 223 of SEQ ID NO: 1;

a nonsense mutation at a position corresponding to amino acid position 464 of SEQ ID NO: 2 and a missense mutation at a position corresponding to amino acid position 234 of SEQ ID NO: 1;

a nonsense mutation at a position corresponding to amino acid position 464 of SEQ ID NO: 2 and a missense mutation at a position corresponding to amino acid position 235 of SEQ ID NO: 1;

a missense mutation at a position corresponding to amino acid position 296 of SEQ ID NO: 2 and a nonsense mutation at a position corresponding to amino acid position 265 of SEQ ID NO: 1;

a missense mutation at a position corresponding to amino acid position 296 of SEQ ID NO: 2 and a missense mutation at a position corresponding to amino acid position 223 of SEQ ID NO: 1;

a missense mutation at a position corresponding to amino acid position 296 of SEQ ID NO: 2 and a missense mutation at a position corresponding to amino acid position 234 of SEQ ID NO: 1;

a missense mutation at a position corresponding to amino acid position 296 of SEQ ID NO: 2 and a missense mutation at a position corresponding to amino acid position 235 of SEQ ID NO: 1;

a missense mutation at a position corresponding to amino acid position 402 of SEQ ID NO: 2 and a nonsense mutation at a position corresponding to amino acid position 265 of SEQ ID NO: 1;

a missense mutation at a position corresponding to amino acid position 402 of SEQ ID NO:2 and a missense mutation at a position corresponding to amino acid position 223 of SEQ ID NO: 1;

a missense mutation at a position corresponding to amino acid position 402 of SEQ ID NO: 2 and a missense mutation at a position corresponding to amino acid position 234 of SEQ ID NO: 1;

a missense mutation at a position corresponding to amino acid position 402 of SEQ ID NO: 2 and a missense mutation at a position corresponding to amino acid position 235 of SEQ ID NO: 1;

a missense mutation at a position corresponding to amino acid position 251 of SEQ ID NO: 2 and a nonsense mutation at a position corresponding to amino acid position 265 of SEQ ID NO: 1;

a missense mutation at a position corresponding to amino acid position 251 of SEQ ID NO: 2 and a missense mutation at a position corresponding to amino acid position 223 of SEQ ID NO: 1;

a missense mutation at a position corresponding to amino acid position 251 of SEQ ID NO: 2 and a missense mutation at a position corresponding to amino acid position 234 of SEQ ID NO: 1;

a missense mutation at a position corresponding to amino acid position 251 of SEQ ID NO: 2 and a missense mutation at a position corresponding to amino acid position 235 of SEQ ID NO: 1;

a missense mutation at a position corresponding to amino acid position 438 of SEQ ID NO: 2 and a nonsense mutation at a position corresponding to amino acid position 561 of SEQ ID NO: 1;
a missense mutation at a position corresponding to amino acid position 438 of SEQ ID NO: 2 and a missense mutation at a position corresponding to amino acid position 223 of SEQ ID NO: 1;
a missense mutation at a position corresponding to amino acid position 438 of SEQ ID NO: 2 and a missense mutation at a position corresponding to amino acid position 234 of SEQ ID NO: 1; and
a missense mutation at a position corresponding to amino acid position 438 of SEQ ID NO: 2 and a missense mutation at a position corresponding to amino acid position 235 of SEQ ID NO: 1.

7. A non-naturally occurring plant material obtained from the non-naturally occurring genetically modified plant or said artificially induced non-naturally occurring mutant plant or part thereof of claim 1, and wherein said non-naturally occurring plant material comprises said at least partially reduced expression or activity of said at least two heavy metal ATPase (HMA) polypeptides encoded by at least said two polynucleotide sequences.

8. A method for producing a non-naturally occurring and genetically modified plant or an artificially induced non-naturally occurring mutant plant or part thereof with reduced accumulation of cadmium when grown in the field, said method comprising the steps of:
(a) providing a non-naturally occurring and genetically modified plant or an artificially induced non-naturally occurring mutant plant or part thereof according to claim 1;
(b) growing the non-naturally occurring and genetically modified plant or the artificially induced non-naturally occurring mutant plant or part thereof of step (a) under field conditions;
(c) harvesting a leaf material from the non-naturally occurring and genetically modified plant or the artificially induced non-naturally occurring mutant plant or part thereof of step (b); and
(d) measuring cadmium content of the harvested leaf material of said non-naturally occurring and genetically modified plant or the artificially induced non-naturally occurring mutant plant or part thereof of step (c);
wherein the harvested leaf material of said non-naturally occurring and genetically modified plant or the artificially induced non-naturally occurring mutant plant or part thereof of step (d) exhibits at least 27% decrease in leaf cadmium content as compared to a leaf material from a corresponding wild type plant or part thereof the same species and grown under identical field conditions.

9. The non-naturally occurring genetically modified plant or said artificially induced non-naturally occurring mutant plant or part thereof according to claim 4, wherein said mutation is a missense or a nonsense mutation.

10. The non-naturally occurring genetically modified plant or said artificially induced non-naturally occurring mutant plant or part thereof according to claim 5,
wherein the at least one mutation at a position corresponding to an amino acid position in the A-domain of the second cytoplasmic loop of the HMA polypeptide encoded by the non-mutated sequence set forth in SEQ ID NO: 3 and at least one mutation at a position corresponding to an amino acid position in the P/N-domain of the third cytoplasmic loop of the HMA polypeptide encoded by the non-mutated sequence set forth in SEQ ID NO: 4 comprises (i) at least one mutation at a position corresponding to amino acid positions 251 to 296 of the A-domain of the second cytoplasmic loop of the HMA polypeptide encoded by the non-mutated sequence set forth in SEQ ID NO: 3 and at least one mutation at a position corresponding to amino acid position 561 of the P/N-domain of the third cytoplasmic loop of the HMA polypeptide encoded by the non-mutated sequence set forth in SEQ ID NO: 4, or (ii) at least one mutation at a position corresponding to amino acid position 251, 293 or 296 of the A-domain of the second cytoplasmic loop of the HMA polypeptide encoded by the non-mutated sequence set forth in SEQ ID NO: 3 and at least one mutation at a position corresponding to amino acid position 561 of the P/N-domain of the third cytoplasmic loop of the HMA polypeptide encoded by the non-mutated sequence set forth in SEQ ID NO: 4;
wherein the at least one mutation at a position corresponding to an amino acid position in the A-domain of the second cytoplasmic loop of the HMA polypeptide encoded by the non-mutated sequence set forth in SEQ ID NO: 3 and at least one mutation at a position corresponding to an amino acid position in the A-domain of the second cytoplasmic loop of the HMA polypeptide encoded by the non-mutated sequence set forth in SEQ ID NO: 4 comprises (i) at least one mutation at a position corresponding to amino acid position 293 of the A-domain of the second cytoplasmic loop of the HMA polypeptide encoded by the non-mutated sequence set forth in SEQ ID NO: 3 and at least one mutation at a position corresponding to amino acid positions 223 to 265 of the A-domain of the second cytoplasmic loop of the HMA polypeptide encoded by the non-mutated sequence set forth in SEQ ID NO: 4, or (ii) at least one mutation at a position corresponding to amino acid position 293 of the A-domain of the second cytoplasmic loop of the HMA polypeptide encoded by the non-mutated sequence set forth in SEQ ID NO: 3 and at least one mutation at a position corresponding to amino acid position 223, 234, 235 or 265 of the A-domain of the second cytoplasmic loop of the HMA polypeptide encoded by the non-mutated sequence set forth in SEQ ID NO: 4;
wherein the at least one mutation at a position corresponding to an amino acid position in the P/N-domain of the third cytoplasmic loop of the HMA polypeptide encoded by the non-mutated sequence set forth in SEQ ID NO: 3 and at least one mutation at a position corresponding to an amino acid position in the P/N-domain of the third cytoplasmic loop of the HMA polypeptide encoded by the non-mutated sequence set forth in SEQ ID NO: 4 comprises at least one mutation at a position corresponding to amino acid positions 402 to 464 of the P/N-domain of the third cytoplasmic loop of the HMA polypeptide encoded by the non-mutated sequence set forth in SEQ ID NO: 3 and at least one mutation at a position corresponding to amino acid position 561 of the P/N-domain of the third cytoplasmic loop of the HMA polypeptide encoded by the non-mutated sequence set forth in SEQ ID NO: 4 comprising at least one mutation at a position corresponding to amino acid position 402 or 464 of the P/N-domain of the third cytoplasmic loop of the HMA polypeptide encoded by the non-mutated sequence set forth in SEQ ID NO: 3 and at least one mutation at a position corresponding to amino acid position 561 of the P/N-domain of the third cytoplasmic loop of the HMA polypeptide encoded by the non-mutated sequence set forth in SEQ ID NO: 4;
wherein the at least one mutation at a position corresponding to an amino acid position in the P/N-domain of the third cytoplasmic loop of the HMA polypeptide encoded by the non-mutated sequence set forth in SEQ ID NO: 3 and at least one mutation at a position corresponding to an amino acid position in the A-domain of the second cytoplasmic loop of the HMA polypeptide encoded by the non-mutated sequence set forth in SEQ ID NO: 4 comprises at least one mutation at a position corresponding to amino acid position 438 of the P/N-domain of the third cytoplasmic loop of the HMA polypeptide encoded by the non-mutated sequence set forth in SEQ ID NO: 3 and at least one mutation at a position corresponding to amino acid position 265 in the A-domain of the second cytoplasmic loop of the HMA polypeptide encoded by the non-mutated sequence set forth in SEQ ID NO: 4;
  wherein the at least one mutation at a position corresponding to an amino acid position in the P/N domain of the third cytoplasmic loop of the HMA polypeptide encoded by the non-mutated sequence set forth in SEQ ID NO: 3 and at least one mutation at a position corresponding to an amino acid position in the A domain of the second cytoplasmic loop of the HMA polypeptide encoded by the non-mutated sequence set forth in SEQ ID NO: 4 comprises at least one mutation at a position corresponding to amino acid positions 464 of the P/N domain of the third cytoplasmic loop of the HMA polypeptide encoded by the non-mutated sequence set forth in SEQ ID NO: 3 and at least one mutation at a position corresponding to amino acid position 265, 223, 234 or 235 of the A domain of the second cytoplasmic loop of the HMA polypeptide encoded by the non-mutated sequence set forth in SEQ ID NO: 4;
  wherein the at least one mutation at a position corresponding to an amino acid position in the A domain of the second cytoplasmic loop of the HMA polypeptide encoded by the non-mutated sequence set forth in SEQ ID NO: 3 and at least one mutation at a position corresponding to an amino acid position in the A domain of the second cytoplasmic loop of the HMA polypeptide encoded by the non-mutated sequence set forth in SEQ ID NO: 4 comprises at least one mutation at a position corresponding to amino acid position 296 of the A domain of the second cytoplasmic loop of the HMA polypeptide encoded by of the non-mutated sequence set forth in SEQ ID NO: 3 and at least one mutation at a position corresponding to amino acid position 265, 223, 234 or 235 of the A domain of the second cytoplasmic loop of the HMA polypeptide encoded by the non-mutated sequence set forth in SEQ ID NO: 4;
  wherein the at least one mutation at a position corresponding to an amino acid position in the P/N domain of the third cytoplasmic loop of the HMA polypeptide encoded by the non-mutated sequence set forth in SEQ ID NO: 3 and at least one mutation at a position corresponding to an amino acid position in the A domain of the second cytoplasmic loop of the HMA polypeptide encoded by the non-mutated sequence set forth in SEQ ID NO: 4 comprises at least one mutation at a position corresponding to amino acid position 402 of the P/N domain of the third cytoplasmic loop of the HMA polypeptide encoded by the non-mutated sequence set forth in SEQ ID NO: 3 and at least one mutation at a position corresponding to amino acid position 265, 223, 234 or 235 of the A domain of the second cytoplasmic loop of the HMA polypeptide encoded by the non-mutated sequence set forth in SEQ ID NO: 4;
wherein the at least one mutation at a position corresponding to an amino acid position in the A domain of the second cytoplasmic loop of the HMA polypeptide encoded by the non-mutated sequence set forth in SEQ ID NO: 3 and at least one mutation at a position corresponding to an amino acid position in the A domain of the second cytoplasmic loop of the HMA polypeptide encoded by the non-mutated sequence set forth in SEQ ID NO: 4 comprises at least one mutation at a position corresponding to amino acid position 251 of the A domain of the second cytoplasmic loop of the HMA polypeptide encoded by the non-mutated sequence set forth in SEQ ID NO: 3 and at least one mutation at a position corresponding to amino acid position 265, 223, 234 or 235 of the A domain of the second cytoplasmic loop of the HMA polypeptide encoded by the non-mutated sequence set forth in SEQ ID NO: 4;
wherein the at least one mutation at a position corresponding to an amino acid position in the P/N domain of the third cytoplasmic loop of the HMA polypeptide encoded by the non-mutated sequence set forth in SEQ ID NO: 3 and at least one mutation at a position corresponding to an amino acid position in the P/N domain of the third cytoplasmic loop of the HMA polypeptide encoded by the non-mutated sequence set forth in SEQ ID NO: 4 comprises at least one mutation at a position corresponding to amino acid position 438 of the P/N domain of the third cytoplasmic loop of the HMA polypeptide encoded by the non-mutated sequence set forth in SEQ ID NO: 3 and at least one mutation at a position corresponding to amino acid position 265, 223, 234 or 235 of the A domain of the second cytoplasmic loop of the HMA polypeptide encoded by the non-mutated sequence set forth in SEQ ID NO: 4;
wherein the at least one mutation at a position corresponding to an amino acid position in the A-domain of the second cytoplasmic loop of the HMA polypeptide encoded by the non-mutated sequence set forth in SEQ ID NO: 4 and at least one mutation at a position corresponding to an amino acid position in an P/N-domain of the third cytoplasmic loop of the HMA polypeptide encoded by the non-mutated sequence set forth in SEQ ID NO: 3 comprises (i) at least one mutation at a position corresponding to amino acid positions 251 to 296 of the A-domain of the second cytoplasmic loop of the HMA polypeptide encoded by the non-mutated sequence set forth in SEQ ID NO: 4 and at least one mutation at a position corresponding to amino acid position 561 of the P/N-domain of the third cytoplasmic loop of the HMA polypeptide encoded by the non-mutated sequence set forth in SEQ ID NO: 3, or (ii) at least one mutation at a position corresponding to amino acid position 251, 293 or 296 of the A-domain of the second cytoplasmic loop of the HMA polypeptide encoded by the non-mutated sequence set forth in SEQ ID NO: 4 and at least one mutation at a position corresponding to amino acid position 561 of the P/N- domain of the third cytoplasmic loop of the HMA polypeptide encoded by the non-mutated sequence set forth in SEQ ID NO: 3;

wherein the at least one mutation at a position corresponding to an amino acid position in the A-domain of the second cytoplasmic loop of the HMA polypeptide encoded by the non-mutated sequence set forth in SEQ ID NO: 4 and at least one mutation at a position corresponding to an amino acid position in the A-domain of the second cytoplasmic loop of the HMA polypeptide encoded by the non-mutated sequence set forth in SEQ ID NO: 3 comprises (i) at least one mutation at a position corresponding to amino acid position 293 of the A-domain of the second cytoplasmic loop of the HMA polypeptide encoded by the non-mutated sequence set forth in SEQ ID NO: 4 and at least one mutation at a position corresponding to amino acid positions 223 to 265 of the A-domain of the second cytoplasmic loop of the HMA polypeptide encoded by the non-mutated sequence set forth in SEQ ID NO: 3, or (ii) at least one mutation at a position corresponding to amino acid position 293 of the A-domain of the second cytoplasmic loop of the HMA polypeptide encoded by the non-mutated sequence set forth in SEQ ID NO: 4 and at least one mutation at a position corresponding to amino acid position 223, 234, 235 or 265 of the A-domain of the second cytoplasmic loop of the HMA polypeptide encoded by the non-mutated sequence set forth in SEQ ID NO: 3;

wherein the at least one mutation at a position corresponding to an amino acid position in the P/N-domain of the third cytoplasmic loop of the HMA polypeptide encoded by the non-mutated sequence set forth in SEQ ID NO: 4 and at least one mutation at a position corresponding to an amino acid position in the P/N-domain of the third cytoplasmic loop of the HMA polypeptide encoded by the non-mutated sequence set forth in SEQ ID NO: 3 comprises (i) at least one mutation at a position corresponding to amino acid positions 402 to 464 of the P/N-domain of the third cytoplasmic loop of the HMA polypeptide encoded by the non-mutated sequence set forth in SEQ ID NO: 4 and at least one mutation at a position corresponding to amino acid position 561 of the P/N-domain of the third cytoplasmic loop of the HMA polypeptide encoded by the non-mutated sequence set forth in SEQ ID NO: 3, or (ii) at least one mutation at a position corresponding to amino acid position 402 or 464 of the P/N-domain of the third cytoplasmic loop of the HMA polypeptide encoded by the non-mutated sequence set forth in SEQ ID NO: 4 and at least one mutation at a position corresponding to amino acid position 561 of the P/N-domain of the third cytoplasmic loop of the HMA polypeptide encoded by the non-mutated sequence set forth in SEQ ID NO: 3;

wherein the at least one mutation at a position corresponding to an amino acid position in the P/N-domain of the third cytoplasmic loop of the HMA polypeptide encoded by the non-mutated sequence set forth in SEQ ID NO: 4 and at least one mutation at a position corresponding to an amino acid position in the A-domain of the second cytoplasmic loop of the HMA polypeptide encoded by the non-mutated sequence set forth in SEQ ID NO: 3 comprises at least one mutation at a position corresponding to amino acid position 438 of the P/N-domain of the third cytoplasmic loop of the HMA polypeptide encoded by the non-mutated sequence set forth in SEQ ID NO: 4 and at least one mutation at a position corresponding to amino acid position 265 in the A-domain of the second cytoplasmic loop of the HMA polypeptide encoded by the non-mutated sequence set forth in SEQ ID NO: 3;

wherein the at least one mutation at a position corresponding to an amino acid position in the P/N domain of the third cytoplasmic loop of the HMA polypeptide encoded by the non-mutated sequence set forth in SEQ ID NO: 4 and at least one mutation at a position corresponding to an amino acid position in the A domain of the second cytoplasmic loop of the HMA polypeptide encoded by the non-mutated sequence set forth in SEQ ID NO: 3 comprises at least one mutation at a position corresponding to amino acid positions 464 of the P/N domain of the third cytoplasmic loop of the HMA polypeptide encoded by the non-mutated sequence set forth in SEQ ID NO: 4 and at least one mutation at a position corresponding to amino acid position 265, 223, 234 or 235 of the A domain of the second cytoplasmic loop of the HMA polypeptide encoded by the non-mutated sequence set forth in SEQ ID NO: 3;

wherein the at least one mutation at a position corresponding to an amino acid position in the A domain of the second cytoplasmic loop of the HMA polypeptide encoded by the non-mutated sequence set forth in SEQ ID NO: 4 and at least one mutation at a position corresponding to an amino acid position in the A domain of the second cytoplasmic loop of the HMA polypeptide encoded by the non-mutated sequence set forth in SEQ ID NO: 3 comprises at least one mutation at a position corresponding to amino acid position 296 of the A domain of the second cytoplasmic loop of the HMA polypeptide encoded by the non-mutated sequence set forth in SEQ ID NO: 4 and at least one mutation at a position corresponding to amino acid position 265, 223, 234 or 235 of the A domain of the second cytoplasmic loop of the HMA polypeptide encoded by the non-mutated sequence set forth in SEQ ID NO: 3;

wherein the at least one mutation at a position corresponding to an amino acid position in the P/N domain of the third cytoplasmic loop of the HMA polypeptide encoded by the non-mutated sequence set forth in SEQ ID NO: 4 and at least one mutation at a position corresponding to an amino acid position in the A domain of the second cytoplasmic loop of the HMA polypeptide encoded by the non-mutated sequence set forth in SEQ ID NO: 3 comprises at least one mutation at a position corresponding to amino acid position 402 of the P/N domain of the third cytoplasmic loop of the HMA polypeptide encoded by the non-mutated sequence set forth in SEQ ID NO: 4 and at least one mutation at a position corresponding to amino acid position 265, 223, 234 or 235 of the A domain of the second cytoplasmic loop of the HMA polypeptide encoded by the non-mutated sequence set forth in SEQ ID NO: 3;

wherein the at least one mutation at a position corresponding to an amino acid position in the A domain of the second cytoplasmic loop of the HMA polypeptide encoded by the non-mutated sequence set forth in SEQ ID NO: 4 and at least one mutation at a position corresponding to an amino acid position in the A domain of the second cytoplasmic loop of the HMA polypeptide encoded by the non-mutated sequence set forth in SEQ ID NO: 3 comprises at least one mutation at a position corresponding to amino acid position 251 of the A domain of the second cytoplasmic loop of the HMA polypeptide encoded by the non-mutated sequence set forth in SEQ ID NO: 4 and at least one mutation at a position corresponding to amino acid position 265, 223, 234 or 235 of the A domain of the second cytoplasmic loop of the HMA polypeptide encoded by the non-mutated sequence set forth in SEQ ID NO: 3; and wherein the at least one mutation at a position corresponding to an amino acid position in the P/N domain of the third cytoplasmic loop of the HMA polypeptide encoded by the non-mutated sequence set forth in SEQ ID NO: 4 and at least one mutation at a position corresponding to an amino acid position in the A domain of the second cytoplasmic loop of the HMA polypeptide encoded by the non-mutated sequence set forth in SEQ ID NO: 3 comprises at least one mutation at a position corresponding to amino acid position 438 of the P/N domain of the third cytoplasmic loop of the HMA polypeptide encoded by the non-mutated sequence set forth in SEQ ID NO: 4 and at least one mutation at a position corresponding to amino acid position 265, 223, 234 or 235 of the A domain of the second cytoplasmic loop of the HMA polypeptide encoded by the non-mutated sequence set forth in SEQ ID NO: 3.

11. The non-naturally occurring genetically modified plant or said artificially induced non-naturally occurring mutant plant or part thereof according to claim 6, wherein the nonsense mutation at a position corresponding to amino acid position 293 of SEQ ID NO: 1 and the nonsense mutation at a position corresponding to amino acid position 561 of the non-mutated sequence set forth in SEQ ID NO:2 comprise a Q293* mutation and a Q561* mutation, and wherein * denotes a stop codon;

wherein the nonsense mutation at a position corresponding to amino acid position 293 of SEQ ID NO: 1 and the nonsense mutation at a position corresponding to amino acid position 265 of the non-mutated sequence set forth in SEQ ID NO:2 comprise a Q293* mutation and a W265* mutation, wherein * denotes a stop codon;

wherein the missense mutation at a position corresponding to amino acid position 296 of SEQ ID NO: 1 and the nonsense mutation at a position corresponding to amino acid position 561 of the non-mutated sequence set forth in SEQ ID NO:2 comprise the E296K mutation and a Q561* mutation, wherein * denotes a stop codon;

wherein the missense mutation at a position corresponding to amino acid position 402 of SEQ ID NO: 1 and the nonsense mutation at a position corresponding to amino acid position 561 of the non-mutated sequence set forth in SEQ ID NO:2 comprise the T402I mutation and a Q561* mutation, wherein * denotes a stop codon;

wherein the missense mutation at a position corresponding to amino acid position 251 of SEQ ID NO: 1 and the nonsense mutation at a position corresponding to amino acid position 561 of the non-mutated sequence set forth in SEQ ID NO: 2 comprise the G251D mutation and a Q561* mutation, wherein * denotes a stop codon;

wherein the nonsense mutation at a position corresponding to amino acid position 293 of SEQ ID NO: 1 and the missense mutation at a position corresponding to amino acid position 223 of the non-mutated sequence set forth in SEQ ID NO:2 comprise a Q293* mutation and the L223F mutation, wherein * denotes a stop codon;

wherein the nonsense mutation at a position corresponding to amino acid position 293 of SEQ ID NO: 1 and the missense mutation at a position corresponding to amino acid position 234 of the non-mutated sequence set forth in SEQ ID NO:2 comprise a Q293* mutation and the D234N mutation, wherein * denotes a stop codon;

wherein the nonsense mutation at a position corresponding to amino acid position 293 of SEQ ID NO: 1 and the missense mutation at a position corresponding to amino acid position 235 of the non-mutated sequence set forth in SEQ ID NO:2 comprise a Q293* mutation and the G235E mutation, wherein * denotes a stop codon;

wherein the nonsense mutation at a position corresponding to amino acid position 464 of SEQ ID NO: 1 and the nonsense mutation at a position corresponding to amino acid position 561 of the non-mutated sequence set forth in SEQ ID NO: 2 comprise a 0464* mutation and a 0561* mutation, wherein * denotes a stop codon;

wherein the missense mutation at a position corresponding to amino acid position 438 of SEQ ID NO: 1 and the nonsense mutation at a position corresponding to amino acid position 265 of the non-mutated sequence set forth in SEQ ID NO:2 comprise the H438Y mutation and a W265* mutation, wherein * denotes a stop codon;

wherein the nonsense mutation at a position corresponding to amino acid position 464 of SEQ ID NO: 1 and the nonsense mutation at a position corresponding to amino acid position 265 of SEQ ID NO:2 comprise a Q464* mutation and a W265* mutation, wherein * denotes a stop codon;

wherein the nonsense mutation at a position corresponding to amino acid position 464 of SEQ ID NO: 1 and the missense mutation at a position corresponding to amino acid position 223 of SEQ ID NO: 2 comprise a Q464* mutation and the L223F mutation, wherein * denotes a stop codon;

wherein the nonsense mutation at a position corresponding to amino acid position 464 of SEQ ID NO: 1 and the missense mutation at a position corresponding to amino acid position 234 of SEQ ID NO: 2 comprise a Q464* mutation and the D234N mutation, wherein * denotes a stop codon;

wherein the nonsense mutation at a position corresponding to amino acid position 464 of SEQ ID NO: 1 and the missense mutation at a position corresponding to amino acid position 235 of SEQ ID NO: 2 comprise a Q464* mutation and the G235E mutation, wherein * denotes a stop codon;

wherein the missense mutation at a position corresponding to amino acid position 296 of SEQ ID NO: 1 and the nonsense mutation at a position corresponding to amino acid position 265 of SEQ ID NO: 2 comprise the E296K mutation and a W265* mutation, wherein * denotes a stop codon;

wherein the missense mutation at a position corresponding to amino acid position 296 of SEQ ID NO: 1 and the missense mutation at a position corresponding to amino acid position 223 of SEQ ID NO: 2 comprise the E296K mutation and the L223F mutation;

wherein the missense mutation at a position corresponding to amino acid position 296 of SEQ ID NO: 1 and the missense mutation at a position corresponding to amino acid position 234 of SEQ ID NO: 2 comprise the E296K mutation and the D234N mutation;

wherein the missense mutation at a position corresponding to amino acid position 296 of SEQ ID NO: 1 and the missense mutation at a position corresponding to amino acid position 235 of SEQ ID NO:2 comprise the E296K mutation and the G235E mutation;

wherein the missense mutation at a position corresponding to amino acid position 402 of SEQ ID NO: 1 and the nonsense mutation at a position corresponding to amino acid position 265 of SEQ ID NO:2 comprise the T402I mutation and a W265* mutation, wherein * denotes a stop codon;

wherein the missense mutation at a position corresponding to amino acid position 402 of SEQ ID NO: 1 and the missense mutation at a position corresponding to amino acid position 223 of SEQ ID NO:2 comprise the T402I mutation and the L223F mutation;

wherein the missense mutation at a position corresponding to amino acid position 402 of SEQ ID NO: 1 and the missense mutation at a position corresponding to amino acid position 234 of SEQ ID NO: 2 comprise the T402I mutation and the D234N mutation;

wherein the missense mutation at a position corresponding to amino acid position 402 of SEQ ID NO: 1 and the missense mutation at a position corresponding to amino acid position 235 of SEQ ID NO: 2 comprise the T402I mutation and the G235E mutation;

wherein the missense mutation at a position corresponding to amino acid position 251 of SEQ ID NO: 1 and the nonsense mutation at a position corresponding to amino acid position 265 of SEQ ID NO: 2 comprise the G251D mutation and a W265* mutation, wherein * denotes a stop codon;

wherein the missense mutation at a position corresponding to amino acid position 251 of SEQ ID NO: 1 and the missense mutation at a position corresponding to amino acid position 223 of SEQ ID NO: 2 comprise the G251D mutation and the L223F mutation;

wherein the missense mutation at a position corresponding to amino acid position 251 of SEQ ID NO: 1 and the missense mutation at a position corresponding to amino acid position 234 of SEQ ID NO: 2 comprise the G251D mutation and the D234N mutation;

wherein the missense mutation at a position corresponding to amino acid position 251 of SEQ ID NO: 1 and the missense mutation at a position corresponding to amino acid position 235 of SEQ ID NO: 2 comprise the G251D mutation and the G235E mutation;

wherein the missense mutation at a position corresponding to amino acid position 438 of SEQ ID NO: 1 and the nonsense mutation at a position corresponding to amino acid position 561 of SEQ ID NO: 2 comprise the H438Y mutation and a Q561* mutation, wherein * denotes a stop codon;

wherein the missense mutation at a position corresponding to amino acid position 438 of SEQ ID NO: 1 and the missense mutation at a position corresponding to amino acid position 223 of SEQ ID NO: 2 comprise the H438Y mutation and the L223F mutation;

wherein the missense mutation at a position corresponding to amino acid position 438 of SEQ ID NO: 1 and the missense mutation at a position corresponding to amino acid position 234 of SEQ ID NO: 2 comprise the H438Y mutation and the D234N mutation;

wherein the missense mutation at a position corresponding to amino acid position 438 of SEQ ID NO: 1 and the missense mutation at a position corresponding to amino acid position 235 of SEQ ID NO: 2 comprise the H438Y mutation and the G235E mutation;

wherein the nonsense mutation at a position corresponding to amino acid position 293 of SEQ ID NO: 2 and the nonsense mutation at a position corresponding to amino acid position 561 of the non-mutated sequence set forth in SEQ ID NO: 1 comprise a Q293* mutation and a Q561* mutation, and wherein * denotes a stop codon;

wherein the nonsense mutation at a position corresponding to amino acid position 293 of SEQ ID NO: 2 and the nonsense mutation at a position corresponding to amino acid position 265 of the non-mutated sequence set forth in SEQ ID NO: 1 comprise a Q293* mutation and a W265* mutation, wherein * denotes a stop codon;

wherein the missense mutation at a position corresponding to amino acid position 296 of SEQ ID NO: 2 and the nonsense mutation at a position corresponding to amino acid position 561 of the non-mutated sequence set forth in SEQ ID NO: 1 comprise the E296K mutation and a Q561* mutation, wherein * denotes a stop codon;

wherein the missense mutation at a position corresponding to amino acid position 402 of SEQ ID NO: 2 and the nonsense mutation at a position corresponding to amino acid position 561 of the non-mutated sequence set forth in SEQ ID NO: 1 comprise the T402I mutation and a Q561* mutation, wherein * denotes a stop codon;

wherein the missense mutation at a position corresponding to amino acid position 251 of SEQ ID NO: 2 and the nonsense mutation at a position corresponding to amino acid position 561 of the non-mutated sequence set forth in SEQ ID NO: 1 comprise the G251D mutation and a Q561* mutation, wherein * denotes a stop codon;

wherein the nonsense mutation at a position corresponding to amino acid position 464 of SEQ ID NO:2 and the nonsense mutation at a position corresponding to amino acid position 561 of the non-mutated sequence set forth in SEQ ID NO: 1 comprise the G251D mutation and a Q561* mutation, wherein * denotes a stop codon;

wherein a nonsense mutation at a position corresponding to amino acid position 293 of SEQ ID NO: 2 and a missense mutation at a position corresponding to amino acid position 223 of the non-mutated sequence set forth in SEQ ID NO: 1 comprise a Q293* mutation and the L223F mutation, wherein * denotes a stop codon;

wherein the nonsense mutation at a position corresponding to amino acid position 293 of SEQ ID NO: 2 and the missense mutation at a position corresponding to amino acid position 234 of the non-mutated sequence set forth in SEQ ID NO: 1 comprise a Q293* mutation and the D234N mutation, wherein * denotes a stop codon;

wherein the nonsense mutation at a position corresponding to amino acid position 293 of SEQ ID NO: 2 and the missense mutation at a position corresponding to amino acid position 235 of the non-mutated sequence set forth in SEQ ID NO: 1 comprise a Q293* mutation and the G235E mutation, wherein * denotes a stop codon;
wherein the missense mutation at a position corresponding to amino acid position 438 of SEQ ID NO: 2 and the nonsense mutation at a position corresponding to amino acid position 265 of the non-mutated sequence set forth in SEQ ID NO: 1 comprise the H438Y mutation and a W265* mutation, wherein * denotes a stop codon;
wherein the nonsense mutation at a position corresponding to amino acid position 464 of SEQ ID NO: 2 and the nonsense mutation at a position corresponding to amino acid position 265 of SEQ ID NO: 1 comprise a Q464* mutation and a W265* mutation, wherein * denotes a stop codon;
wherein the nonsense mutation at a position corresponding to amino acid position 464 of SEQ ID NO: 2 and the missense mutation at a position corresponding to amino acid position 223 of SEQ ID NO: 1 comprise a Q464* mutation and the L223F mutation, wherein * denotes a stop codon;
wherein the nonsense mutation at a position corresponding to amino acid position 464 of SEQ ID NO: 2 and the missense mutation at a position corresponding to amino acid position 234 of SEQ ID NO: 1 comprise a Q464* mutation and the D234N mutation, wherein * denotes a stop codon;
wherein the nonsense mutation at a position corresponding to amino acid position 464 of SEQ ID NO: 2 and the missense mutation at a position corresponding to amino acid position 235 of SEQ ID NO: 1 comprise a Q464* mutation and the G235E mutation, wherein * denotes a stop codon;
wherein the missense mutation at a position corresponding to amino acid position 296 of SEQ ID NO: 2 and the nonsense mutation at a position corresponding to amino acid position 265 of SEQ ID NO: 1 comprise the E296K mutation and a W265* mutation, wherein * denotes a stop codon;
wherein the missense mutation at a position corresponding to amino acid position 296 of SEQ ID NO:2 and the missense mutation at a position corresponding to amino acid position 223 of SEQ ID NO: 1 comprise the E296K mutation and the L223F mutation;
wherein the missense mutation at a position corresponding to amino acid position 296 of SEQ ID NO: 2 and the missense mutation at a position corresponding to amino acid position 234 of SEQ ID NO: 1 comprise the E296K mutation and the D234N mutation;
wherein the missense mutation at a position corresponding to amino acid position 296 of SEQ ID NO: 2 and the missense mutation at a position corresponding to amino acid position 235 of SEQ ID NO: 1 comprise the E296K mutation and the G235E mutation;
wherein the missense mutation at a position corresponding to amino acid position 402 of SEQ ID NO: 2 and the nonsense mutation at a position corresponding to amino acid position 265 of SEQ ID NO: 1 comprise the T402I mutation and a W265* mutation, wherein * denotes a stop codon;
wherein the missense mutation at a position corresponding to amino acid position 402 of SEQ ID NO: 2 and the missense mutation at a position corresponding to amino acid position 223 of SEQ ID NO: 1 comprise the T402I mutation and the L223F mutation;
wherein the missense mutation at a position corresponding to amino acid position 402 of SEQ ID NO: 2 and the missense mutation at a position corresponding to amino acid position 234 of SEQ ID NO: 1 comprise the T402I mutation and the D234N mutation;
wherein the missense mutation at a position corresponding to amino acid position 402 of SEQ ID NO: 2 and the missense mutation at a position corresponding to amino acid position 235 of SEQ ID NO: 1 comprise the T402I mutation and the G235E mutation;
wherein the missense mutation at a position corresponding to amino acid position 251 of SEQ ID NO: 2 and the nonsense mutation at a position corresponding to amino acid position 265 of SEQ ID NO: 1 comprise the G251D mutation and a W265* mutation, wherein * denotes a stop codon;
wherein the missense mutation at a position corresponding to amino acid position 251 of SEQ ID NO: 2 and the missense mutation at a position corresponding to amino acid position 223 of SEQ ID NO: 1 comprise the G251D mutation and the L223F mutation;
wherein the missense mutation at a position corresponding to amino acid position 251 of SEQ ID NO: 2 and the missense mutation at a position corresponding to amino acid position 234 of SEQ ID NO: 1 comprise the G251D mutation and the D234N mutation;
wherein the missense mutation at a position corresponding to amino acid position 251 of SEQ ID NO: 2 and the missense mutation at a position corresponding to amino acid position 235 of SEQ ID NO: 1 comprise the G251D mutation and the G235E mutation;
wherein the missense mutation at a position corresponding to amino acid position 438 of SEQ ID NO: 2 and the nonsense mutation at a position corresponding to amino acid position 561 of SEQ ID NO: 1 comprise the H438Y mutation and a Q561* mutation, wherein * denotes a stop codon;
wherein the missense mutation at a position corresponding to amino acid position 438 of SEQ ID NO: 2 and the missense mutation at a position corresponding to amino acid position 223 of SEQ ID NO: 1 comprise the H438Y mutation and the L223F mutation;
wherein the missense mutation at a position corresponding to amino acid position 438 of SEQ ID NO: 2 and the missense mutation at a position corresponding to amino acid position 234 of SEQ ID NO: 1 comprise the H438Y mutation and the D234N mutation; and
wherein the missense mutation at a position corresponding to amino acid position 438 of SEQ ID NO:2 and the missense mutation at a position corresponding to amino acid position 235 of SEQ ID NO: 1 comprise the H438Y mutation and the G235E mutation.

12. The non-naturally occurring plant material from the non-naturally occurring genetically modified plant or said artificially induced non-naturally occurring mutant plant or part thereof of claim 7, wherein the plant material is cured or dried plant material, wherein the phenotype of said non-naturally occurring genetically modified plant or said artificially induced non-naturally occurring mutant plant or part thereof at harvest time is the same as the corresponding wild type plant at the same harvest time, or wherein the non-naturally occurring genetically modified plant or said artificially induced non-naturally occurring mutant plant or part thereof does not show a biomass reduction at harvest time as compared to the corresponding wild type plant at the same harvest time.

13. The non-naturally occurring and genetically modified plant or said artificially induced non-naturally occurring mutant plant or part thereof according to claim 1, wherein said polypeptides having at least 95% amino acid sequence identity to the amino acid sequence set forth in SEQ ID NO: 1 and SEQ ID NO: 2 comprise a mutation in a phosphorylation domain, a mutation in a nucleotide binding domain, or a mutation in an actuator domain relative to the non-mutated amino acid sequence as set forth in SEQ ID NO: 1 and SEQ ID NO:2.

* * * * *